(12) United States Patent
Brodsky

(10) Patent No.: US 8,318,490 B2
(45) Date of Patent: *Nov. 27, 2012

(54) PRELAMIN A PRE PEPTIDE AS A UNIVERSAL STEM CELL DIFFERENTIATION SIGNAL

(75) Inventor: Gary Brodsky, Denver, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 70 days.

This patent is subject to a terminal disclaimer.

(21) Appl. No.: 12/302,563

(22) PCT Filed: May 25, 2007

(86) PCT No.: PCT/US2007/069790
§ 371 (c)(1),
(2), (4) Date: Jan. 23, 2009

(87) PCT Pub. No.: WO2008/008569
PCT Pub. Date: Jan. 17, 2008

(65) Prior Publication Data
US 2009/0175836 A1 Jul. 9, 2009

Related U.S. Application Data

(60) Provisional application No. 60/808,722, filed on May 26, 2006.

(51) Int. Cl.
*C12N 5/00* (2006.01)
*C12N 5/02* (2006.01)
(52) U.S. Cl. .................. 435/377; 435/384; 435/375
(58) Field of Classification Search ............... 435/377
See application file for complete search history.

(56) References Cited

U.S. PATENT DOCUMENTS

| | | | |
|---|---|---|---|
| 4,957,735 A | 9/1990 | Huang | |
| 5,705,151 A | 1/1998 | Dow et al. | |
| 7,291,699 B2 | 11/2007 | Brodsky | |
| 7,297,492 B2 | 11/2007 | Eriksson et al. | |
| 2008/0085323 A1 | 4/2008 | Brodsky | |

OTHER PUBLICATIONS

Park, H-W. et al. Science 275: 1800-1804 (1997).*
Cleland et al, 2001, Current Opinion in Biotechnology, 12:212-219.*
Kobsa, 2008, Pediatric Research, 63:513-519.*
Yuan, 2011, PLoS Once, 6:e17540, 1-16.*
International Preliminary Report on Patentability for International (PCT) Patent Application No. PCT/US2007/069790, issued Nov. 28, 2008.
Altschul, et al., "Gapped BLAST and PSI-BLAST: A new generation of protein database search programs", Nucleic Acids Research, Sep. 1, 1997, pp. 3389-3402, vol. 25, No. 17.
Aoki, et al., "Efficient in vivo gene transfer into the heart in the rat myocardial infarction model using the HVJ (Hemagglutinating Virus of Japan)—liposome method", Journal of Molecular and Cellular Cardiology, Mar. 1997, vol. 29, No. 3, pp. 949-959.
Ardati, et al., "Statin-associated rhabdomyolysis", Pharmacoepidemiology and Drug Safety, Apr. 2005, vol. 14, No. 4, p. 287.
Barton, et al. "Prenylated prelamin A interacts with Narf, a novel nuclear protein", Journal of Biological Chemistry 274(42): 30008-30018 (1999).
Bergo, et al., "Zmpste24 deficiency in mice causes spontaneous bone fractures, muscle weakness, and a prelamin A Processing Defect", Proceedings of the National Academy of Sciences of the United States of America, Oct. 1, 2002, pp. 13049-13054, vol. 99, No. 20.
Biben, et al., "Developmental and tissue-specific regulation of the murine cardiac actin gene in vivo depends on distinct skeletal and cardiac muscle-specific enhancer elements in addition to the proximal promoter", Developmental Biology, Jan. 10, 1996, pp. 200-212, vol. 173, No. 1.
Blaese, et al., "T lymphocyte-directed gene therapy for ADA- SCID: initial trial results after 4 years", Science, Oct. 20, 1995, pp. 475-480, vol. 270, No. 5235.
Bonne, et al., "Mutations in the gene encoding lamin A/C cause autosomal dominant Emery-Dreifuss muscular dystrophy", Nature Genetics, Mar. 1999, vol. 21, No. 3, pp. 285-288.
Bordignon, et al., "Gene therapy in peripheral blood lymphocytes and bone marrow for ADA—immunodeficient patients", Science, Oct. 20, 1995, pp. 470-475, vol. 270, No. 5825.
Boyartchuk, et al., "Roles of Prenyl Protein Proteases in Maturation of *Saccharaomyces cerevisiae* a-Factor", Genetics, Sep. 1998, pp. 95-101, vol. 150.
Brodsky, et al., "Lamin A/C Gene Mutation Associated with Dilated Cardiomyopathy with Variable Skeletal Muscle Involvement", Circulation, 2000, pp. 473-476, vol. 101.
Brodsky, et al., "The prelamin A pre-peptide induces cardiac and skeletal myoblast differentiation", Biochemical and Biophysical Research Communications, May 18, 2007, pp. 872-879 vol. 356, No. 4.
Broers, et al., Journal of Cell Science, 1999, vol. 147, pp. 913-920.
Cadinanos, et al., "Identification, functional expression and enzymatic analysis of two distinct CaaX proteases from *Caenorhabditis elegans*", The Biochemical Journal, Mar. 15, 2003, pp. 1047-1054, vol. 370, Part 3.
Capetanaki, et al., "Desmin in muscle formation and maintenance: knockouts and consequences", Cell Structure and Function, Feb. 1997, pp. 103-116 vol. 22, No. 1.
Chaly, et al., "Remodelling of the Nuclear Periphery During Muscle Cell Differentiation in Vitro", Journal of Cellular Biochemisty, 1996, pp. 76-89, vol. 62.
Chen, et al., "Control of myoblast fusion by a guanine nucleotide exchange factor, loner, and its effector ARF6", Cell, Sep. 19, 2003, pp. 751-762, vol. 114, No. 6.

(Continued)

*Primary Examiner* — Valarie Bertoglio
(74) *Attorney, Agent, or Firm* — Sheridan Ross P.C.

(57) ABSTRACT

Disclosed is the use of prelamin A pre peptide and homologues or analogs thereof for the induction of cell differentiation and tissue or organ growth and repair processes. The invention extends to virtually any cell, including both embryonic and non-embryonic stem cells, such as stem cells that are progenitors for a wide variety of cell and tissue types. Also disclosed is the use of prelamin A pre peptide and prelamin A to determine and establish cell morphology and tissue architecture. Treatment of a variety of diseases and conditions, as well as cosmetic, general health, and anti-aging applications are described.

4 Claims, 23 Drawing Sheets

OTHER PUBLICATIONS

Constantinescu, et al., "Lamin A/C Expression is a marker of mouse and human embryonic stem cell differentiation", Stem Cells, Jan. 2006, vol. 24, pp. 177-185.

Corrigan, et al., "Prelamin A endoproteolytic processing in vitro by recominant Zmpste24", The Biochemical Journal, Apr. 1, 2005, pp. 129-138, vol. 387, Part 1.

Dalton, et al., "The Farnesyl Protein Transferase Inhibitor BZA-5B Blocks Farnesylation of Nuclear Lamins and p21$^{ras}$ but Does Not Affect Their Function or Localization", Cancer Research, Aug. 1, 1995, pp. 3295-3304, vol. 55.

De Sandre-Giovannoli, et al., "Homozygous defects in LMNA, encoding lamin A/C nuclear-envelope proteins, cause autosomal recessive axonal neuropathy in human (Charcot-Marie-Tooth disorder type 2) and mouse", American Journal of Human Genetics, Mar. 2002, pp. 726-736, vol. 70, No. 3.

Elion, "Pheromone response, mating and cell biology", Current Opin. Microbiol, Dec. 2000, pp. 573-581, vol. 3, No. 6.

Eriksson, et al., "Recurrent de novo point mutations in lamin A cause Hutchinson-Gilford progeria syndrome", Nature, May 15, 2003, pp. 293-298 vol. 423, No. 6937.

Fatkin, et al., "Missense Mutations in the Rod Domain of the Lamin A/C Gene as Causes of Dilated Cardiomyopathy and Conduction-System Disease", New Journal of Medicine, Dec. 2, 1999, pp. 1715-1724, vol. 341, No. 23.

Favreau et al., "Expression of Lamin A mutated in the carboxy-terminal tail generates an aberrant nuclear phenotype similar to that observed in cells from patients with Dunnigan-type partial lipodystrophy and Emery-Dreifuss muscular dystrophy", Experimental Cell Research 282: 14-23 (2003; Published online Nov. 11, 2002).

Fiser, et al., "cDNA sequencing of nuclear lamins A and C reveals primary and secondary structural homology to intermediate filamnet proteins", Proceedings of the National Academy of Sciences of the United States of America, Sep. 1986, pp. 6450-6454 vol. 83, No. 17.

Fong, et al., "A protein farnesyltransferase inhibitor ameliorates disease in a mouse model of progeria", Science, Mar. 17, 2006, pp. 1621-1623, vol. 311, No. 5767.

Fong, et al. "Prelamin A and lamin A appear to be dispensable in the nuclear lamina", The Journal of Clinical Investigation, Mar. 2006, pp. 743-752, vol. 116.

Frock, et al., "Lamin A/C and emerin are critical for skeletal muscle satellite cell differentiation", Genes & Development, Feb. 15, 2006, pp. 486-500 vol. 20, No. 4.

Fuchs, et al., "Intermediate filaments: structure, dynamics, function and disease", Annual Review of Biochemistry, 1994, pp. 345-382 vol. 63.

Gotzmann, et al., "Lamins and lamin-binding proteins in functional chromatin organization", 1999, Critical Reviews in Eukaryotic Gene Expression, pp. 257-265, vol. 9, No. 3-4 (Abstract Only).

Haas, et al., "Functional analysis of phosphorylation sites in human lamin A controlling lamin disassembly, nuclear transport and assembly", European Journal of Cell Biology, Dec. 1993, pp. 237-247, vol. 62, No. 2.

Haque, et al., "SUN1 interacts with nuclear Lamin A and Cytoplasmic Nesprins to provide a Physical Connection between the Nuclear Lamin and the Cystoskeleton", Molecular and Cellular Biology, May 2006, pp. 3738-3751, vol. 26, No. 10.

Hennekes, et al., "The role of isoprenylation in membrane attachment of nuclear lamins. A sinlge point mutation prevents proteolytic cleavage of the lamin A precursor and confers membrane binding properties", Journal of Cell Science, Apr. 1994, pp. 1019-1029 vol. 107, part 4.

Ho, et al., "Target-sensitive immunoliposomes as an efficient drug carrier for antiviral activity", The Journal of Biological Chemistry, Oct. 15, 1987, pp. 13973-13978, vol. 262, No. 29.

Ho, et al., "Interactions of target-sensitive immunoliposomes with herpes simplex virus. The foundation of a sensitive immunoliposome assay for the virus", The Journal of Biological Chemistry, Oct. 15, 1987, pp. 13979-13984, vol. 262, No. 29.

Izumi, et al., "Head and/or CaaX domain deletions of lamin proteins disrupt preformed lamin A and C but not lamin B structure in mammalian cells", Molecular Biology of the Cell, Dec. 2000, pp. 4323-4337, vol. 11, No. 12.

Kaneda, et al., "Prevention of Restenosis by Gene Therapy", Annals of the New York Academy of Sciences, Apr. 15, 1997, pp. 299-308 vol. 811.

Kilic, et al., "Regulation of prerlamin A endoprotease activity by prelamin A", FEBS Letters, 1997, pp. 65-68.

Kilic, et al. Journal of Biological Chemistry 272(8): 5298-5304 (1997).

Kitten, et al., "The CaaX motif is required for isoprenylation, carboxyl methylation and nuclear membrane association of lamin B2", The Journal of Cell Biology, Apr. 1991, pp. 13-23, vol. 113, No. 1.

Knapp, et al., "Loss of myogenin in postnatal life leads to normal skeletal 15 muscle but reduced body size", Development, Feb. 2006, pp. 601-610, vol. 133, No. 4.

Koeberl, et al., "Persistent expression of human clotting factor IX from mouse liver after intravenous injection of adeno-associated virus vectors", Proceedings of the National Academy of Sciences of the United States of America, Feb. 18, 1997, pp. 1426-1431, vol. 94, No. 4.

Kumaran, et al., "Lamin A/C speckles mediate spatial organization of splicing factor compartments and RNA polymerase II transcription", The Journal of Cell Biology, Dec. 9, 2002, pp. 783-793, vol. 159, No. 5.

Labarge, et al., "Biological progression from adult bone marrow to mononucleate muscle stem cell to multinucleate muscle fiber in response to injury", Cell, Nov. 15, 2002, pp. 589-601, vol. 111, No. 4.

Libotte, et al., "Lamin A/C -dependent localization of Nesprin-2, a giant scaffolder at the nuclear envelope", Molecular Biology of the Cell, Jul. 2005, pp. 3411-3424, vol. 16, No. 7.

Liu, et al., "Factors influencing the efficiency of cationic liposome-mediated intravenous gene delivery", Nature Biotechnology, Feb. 1997, p. 167-173, vol. 15, No. 2.

Lloyd, et al., "A novel interaction between lamin A and SREBP1: implications for partial lipodystrophy and other laminopathies", Human Molecular Genetics, 2002, pp. 769-777, vol. 11, No. 7.

Lockard, et al., Trans-cellular desmin-lamin B intermediate filament network in cardiac myocytes, Journal of Molecular and Cellular Cardiology, Mar. 1993, pp. 303-309, vol. 25, No. 3.

Lutz, et al., "Nucleoplasmic localization of prelamin A: Implications for prenylation-dependent lamin A assembly in the nuclear lamina", Proceedings of the National Academy of Sciences of the United States of America, Apr. 1 1992, pp. 3000-3004, vol. 89, No. 7.

Mallampalli, et al., "Inhibiting farnesylation reverses the nuclear morphology defect in a HeLa cell model for Hutchinson-Gilford progeria syndrome" Proceedings of the National Academy of Sciences of the United States of America, Oct. 4, 2005, vol. 102, No. 40, pp. 14416-14421.

Marcus, et al., "Total In Vitro Maturation of the *Saccharomyces cerevisiae* a-Factor Lipopeptide Mating Pheromone", Biochemical and Biophysical Research Communications, Nov. 15, 1990, pp. 1310-1316, vol. 172, No. 3.

Markiewicz, et al., "Lamin A/C binding protein LAP2alpha is required for nuclear anchorage of retinoblastoma protein", Molecular Biology of the Cell, Dec. 2002, pp. 4401-4413 vol. 13, No. 12.

Mattout, et al., "Nuclear lamins, diseases and aging", Current Opinion in Cell Biology, Jun. 2006, pp. 335-341, vol. 18, No. 3.

Maurice, et al., "Enhancement of cardiac function after adenoviral-mediated in vivo intracoronary beta2-adrenergic receptor gene delivery", The Journal of Clinical Investigation, Jul. 1999, pp. 21-29, vol. 104, No. 1.

Menard, et al., "Modulation of L-Type calcium channel expression during retinoic acid-induced differentiation of H9C2 cardiac cells", The Journal of Biological Chemistry, Oct. 8, 1999, pp. 29063-29070, vol. 274, No. 41.

Moulson, et al, "Honozygous and compound heterozygous mutations in ZMPSTE24 cause the laminopathy restrictive dermopathy", The Journal of Investigative Dermatology, Nov. 2005, pp. 913-919, vol. 125, No. 5.

Mounkes, et al., "Expression of an LMNA-N195K Variant of A-type lamins results in cardiac conduction defects and death in mice", Human Molecular Genetics, Aug. 1, 2005, pp. 2167-2180, vol. 14, No. 15.

Muchir, et al., "Identification of mutations in the gene encoding lamins A/C in autosomal dominant limb girdle muscular dystrophy with atrioventricular conduction disturbances (LGMD1B)", Human Molecular Genetics, May 22, 2000, pp. 1453-1459, vol. 9, No. 9.

Muralikrishna, et al., "Distinct changes in intranuclear lamin A/C organization during myoblast differentiation", Journal of Cell Science, 2001, pp. 4001-4011, vol. 114.

Newport, et al., "A lamin-independent pathway for nuclear envelope assembly", The Journal of Cell Biology, Dec. 1990, pp. 2247-2259, vol. 111, No. 6, Part I.

Novelli, et al., "Mandibuloacral dysplasia is caused by a mutation in LMNA-encoding lamin A/C", American journal of human genetics, pp. 426-431, Aug. 2002, vol. 71, No. 2.

Östlund, et al., "Properties of lamin A mutants found in Emery-Dreifuss musclular dystrophy, cardiomyopthy and Dunnigan-type partial lipodystrophy", Journal of Cell Science, 2001, pp. 4435-4445, vol. 114.

Ozaki, et al., "Complex formation between lamin A and the retinoblastoma gene product: identification of the domain on lamin A required for its interaction", Oncogene, Sep. 1994, pp. 2649-2653, vol. 9, No. 9.

Pagano, et al., "Differentiation of H9c2 cardiomyoblasts: The role of adenylate cyclase system", Journal of Cellular Physiology, Mar. 2004, pp. 408-416, vol. 198, No. 3.

Pavlath, et al., "Localization of muscle gene products in nuclear domains", Nature, Feb. 9, 1989, pp. 570-573, vol. 337, No. 6207.

Pendás, et al., "Defective prelamin A processing and muscular and adipocyte alterations in Zmpste24 metalloproteinase-deficient mice", Nature Genetics, May 2002, pp. 94-99, vol. 31.

Reharjo, et al., "Nuclear envelope defects associated with LMNA mutations cause dilated cardiomyopathy and Emery-Dreifuss muscular dystrophy", Journal of Cell Science, 2001, pp. 4447-4457, vol. 114.

Rober, et al., "Differential timing of nuclear lamin A/C expression in the various organs of the mouse embryo and the young animal: a developmental study", Development, Feb. 1989, pp. 365-378, vol. 105, No. 2.

Scaffidi, et al., "Lamin A-Dependent Nuclear Defects in Human Aging", Science, May 19, 2006, pp. 1059-1063, vol. 312, No. 5776.

Schuster, et al., "Assembly and function of a quaternary signal transduction complex monitored by surface plasmon resonance", Nature, Sep. 23, 1993, pp. 343-347, vol. 365, No. 6444.

Shackleton, et al., "LMNA, encoding lamin A/C, is mutated in partial lipodystrophy", Nature Genetics, Feb. 2000, pp. 153-156, vol. 24, No. 2.

Sherrill, et al., "Synthesis and Biological Activity of Fluorescent Yeast Pheromones", Biochemistry, 1995, vol. 34, pp. 3553-3560.

Sinesky, et al., "Expression of prelamin A but not mature lamin A confers sensitivity of DNA biosynthesis to lovastatin on F9 teratocarcinoma cells", Journal of Cell Science, 1994, pp. 2215-2218, vol. 107.

Slee, et al., "Executioner caspase-3, -6, and -7 perform distinct, non-redundant roles during the demolition phase of apoptosis", The Journal of Biological Chemistry, Mar. 9, 2001, pp. 7320-7326, vol. 276, No. 10.

Spann, et al., "Disruption of nuclear lamin organization alters the distribution of replication factors and inhibits DNA synthesis", The Journal of Cell Biology, Mar. 24, 1997, pp. 1201-1212, vol. 136, No. 6.

Spann, et al., "Alteration of nuclear lamin organization inhibits RNA polymerase II-dependent transcription", The Journal of Cell Biology, Feb. 18, 2002, pp. 603-608 vol. 156, No. 4.

Stribling, et al., "Aerosol gene delivery in vivo", Proceedings of the National Academy of Sciences of the United States of America, Dec. 1, 1992, pp. 11277-11281 vol. 89, No. 23.

Sullivan, et al., "Loss of A-type Lamin Expression Compromises Nuclear Envelope Integrity Leading to Muscular Dystrophy", The Journal of Cell Biology, Nov. 29, 1999, pp. 913-919, vol. 147, No. 5.

Taylor, et al., "Natural History of Dilated Cardiomyopathy Due to Lamin A/C Gene Mutations", Journal of the American College of Cardiology, 2003, pp. 771-780, vol. 41, No. 5.

Toth, et al., "Blocking protein farnesyltransferase improves nuclear shape in fibroblasts from humans with progeroid syndromes", Proceedings of the National Academy of Sciences of the United States of America, Sep. 6, 2005, pp. 12873-12878 vol. 102, No. 36.

Trueblood, et al., "The CaaX Proteases, Afc1p and Rce1p, Have Overlapping but Distinct Substrate Specificities", Molecular and Cellular Biology, Jun. 2000, pp. 4381-4392, vol. 20, No. 12.

Von Der Leyen, et al., "Gene therapy inhibiting neointimal vascular lesion: in vivo transfer of endothelial cell nitric oxide synthase gene", Proceedings of the National Academy of Sciences of the United States of America, Feb. 14, 1995, pp. 1137-1141, vol. 92, No. 4.

Wakelam, "The Fusion of myoblasts", The Biochemical Journal, May 15, 1985, pp. 1-12, vol. 228, No. 1.

Xie, et al., "Synthesis and Biological Evaluation of the Geometric Farnesylated Analogues of the a-Factor Mating Peptide of *Saccharomyces cerevisiae*", J. Org. Chem., 2000, vol. 65, pp. 8552-8563.

Yang, et al., "Blocking protein farnesyltransferase improves nuclear blebbing in mouse fibroblasts with a targeted Hutchinson-Gildord progeria syndrome mutation", Proceedings of the National Academy of Sciences of the United States of America, Jul. 19, 2005, pp. 10291-10296, vol. 102, No. 29.

Zammit, et al.,"Kinetics of myoblast proliferation show that resident satellite cells are competent to fully regenerate skeletal muscle fibers", Experimental Cell Research, Nov. 15, 2002, pp. 39-49, vol. 281, No. 1.

Baron, et al., "RhoB prenylation is driven by the three carboxyl-terminal amino acids of the protein: evidenced in vivo by an anti-farnesyl cysteine antibody", Proceedings of the National Academy of Sciences of the United States of America, Oct. 10, 2000, pp. 11626-11631, vol. 97, No. 21.

International Search Report for International (PCT) Patent Application No. PCT/US07/69790, mailed Jul. 25, 2008.

Written Opinion for International (PCT) Patent Application No. PCT/US07/69790, mailed Jul. 25, 2008.

\* cited by examiner

Fig. 3

Alignment of pre sequences

|  | 1 | 2 | 3 | 4 | 5 | 6 | 7 | 8 | 9 | 10 | 11 | 12 | 13 | 14 | 15 | 16 | 17 | 18 | |
|---|---|---|---|---|---|---|---|---|---|---|---|---|---|---|---|---|---|---|---|
| Human | L | L | G | N | S | S | P | R | T | Q | S | P | Q | N | C | S | H | M | (SEQ ID NO:20) |
| Mouse | L | L | G | N | S | S | P | R | S | Q | S | S | Q | N | C | S | H | M | (SEQ ID NO:21) |
| Chicken | V | L | G | G | A | G | P | R | R | Q | A | PAP | Q | G | C | S | H | M | (SEQ ID NO:22) |
| Xenopus | I | V | G | N | G | Q | R | A | Q | V | A | P | Q | N | C | S | H | M | (SEQ ID NO:23) |
| Zebrafish | I | V | S | N | D | K | P | R | Q | A | G | P | KVDN | C | S | I | M | | (SEQ ID NO:24) |

Yeast  YIIKGVFWDPAC

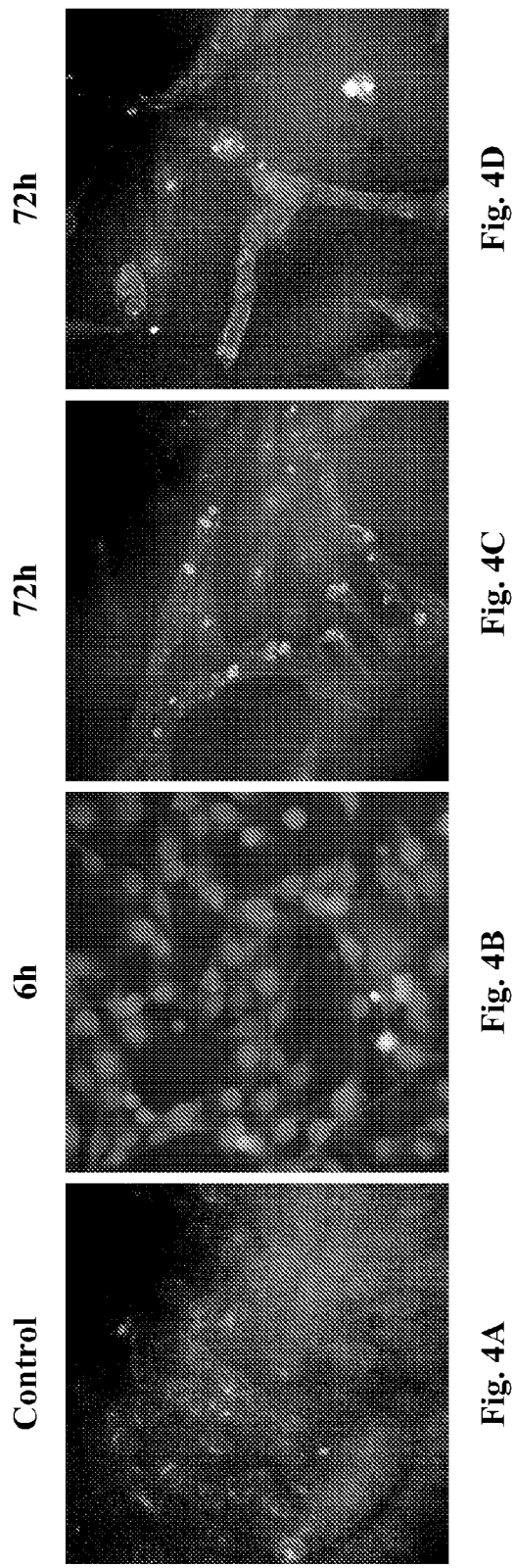

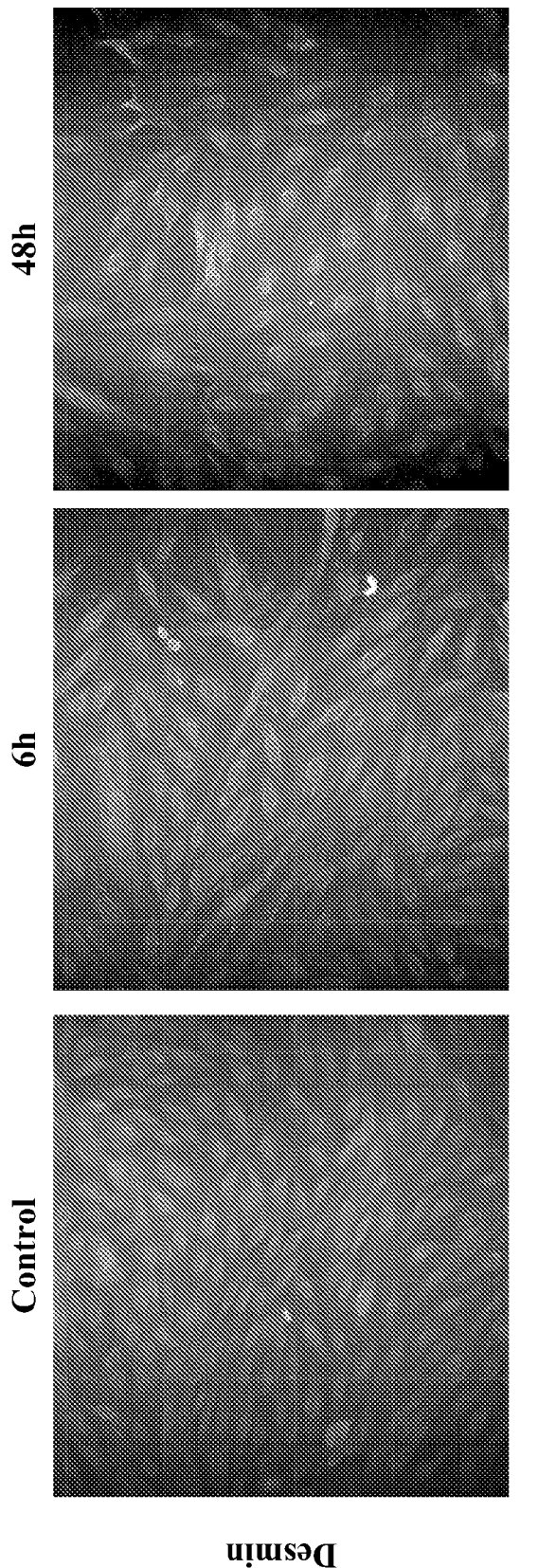

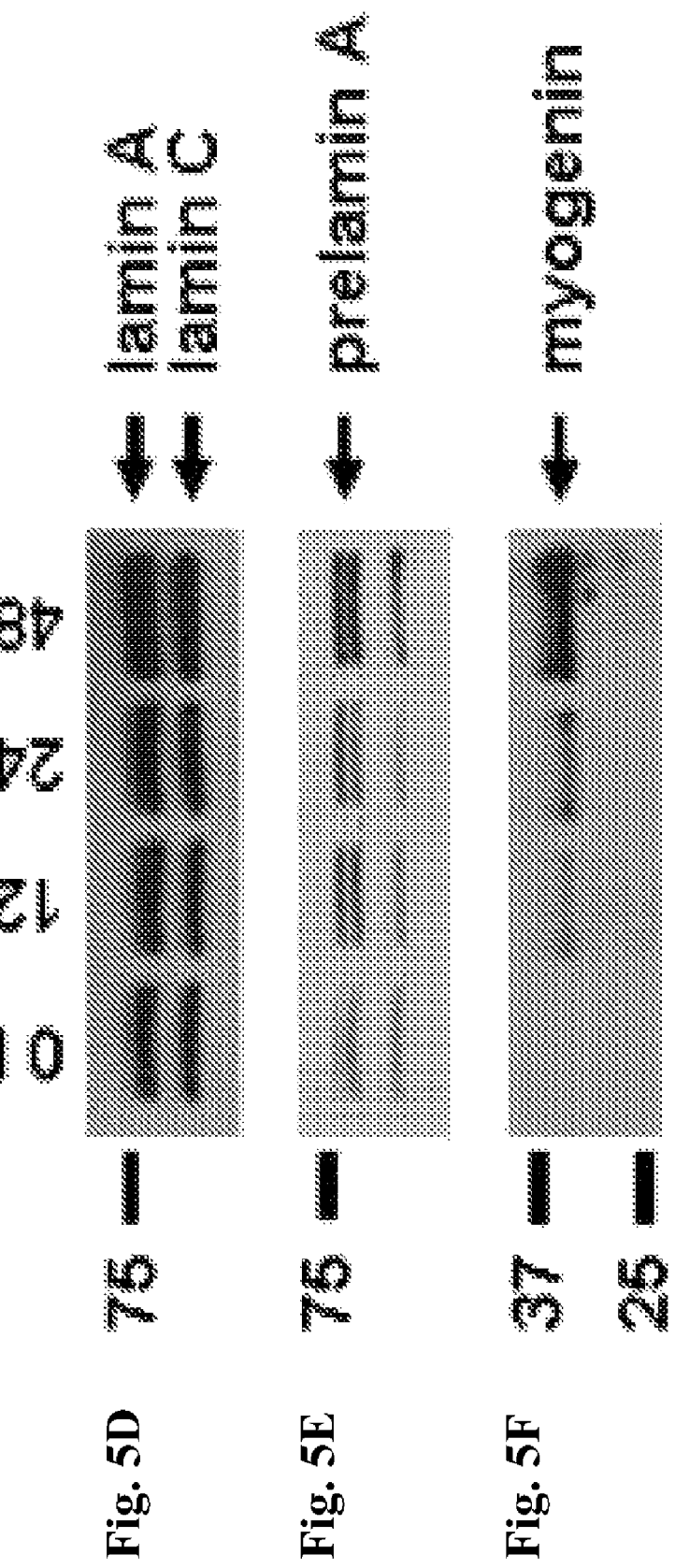

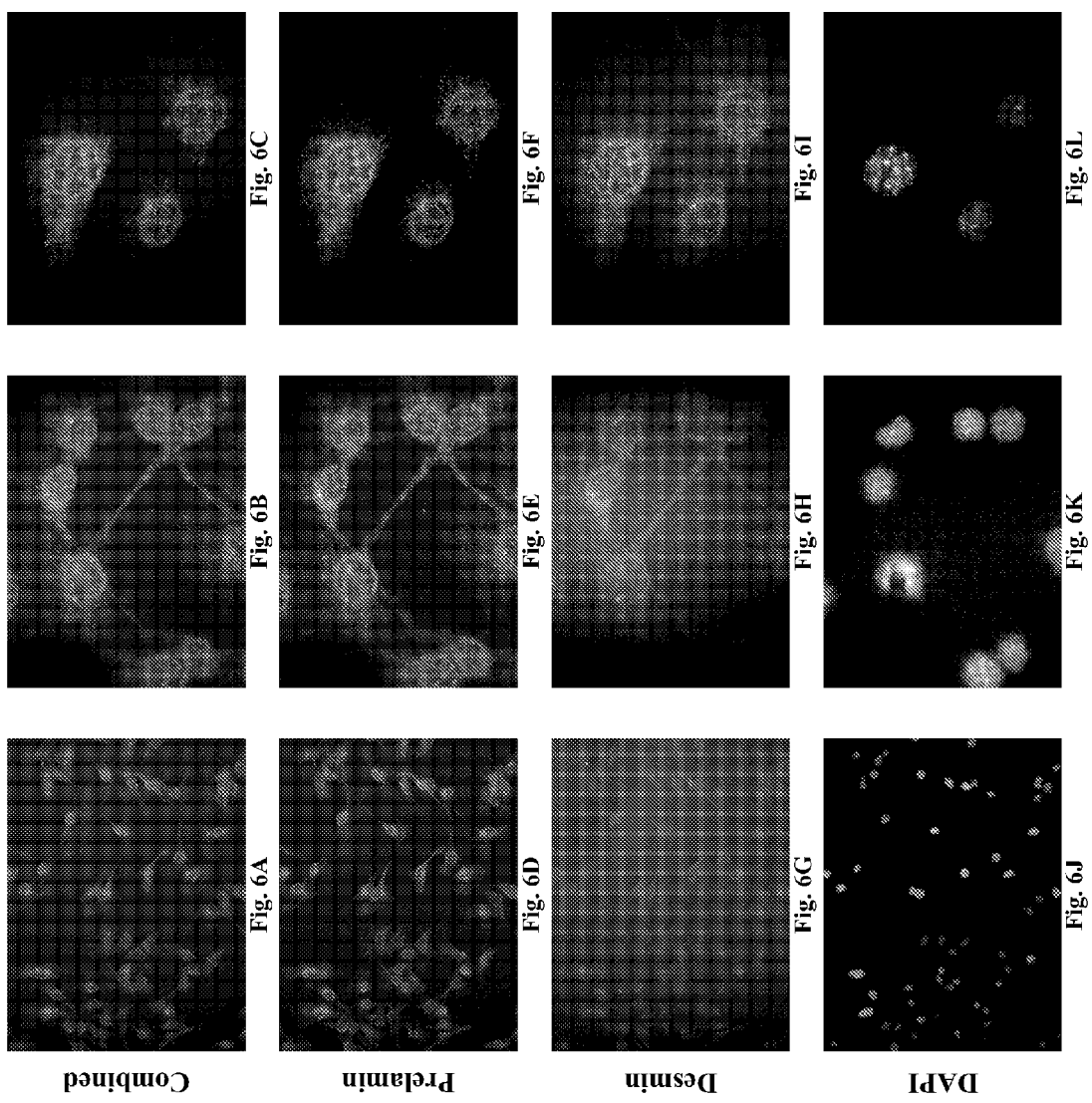

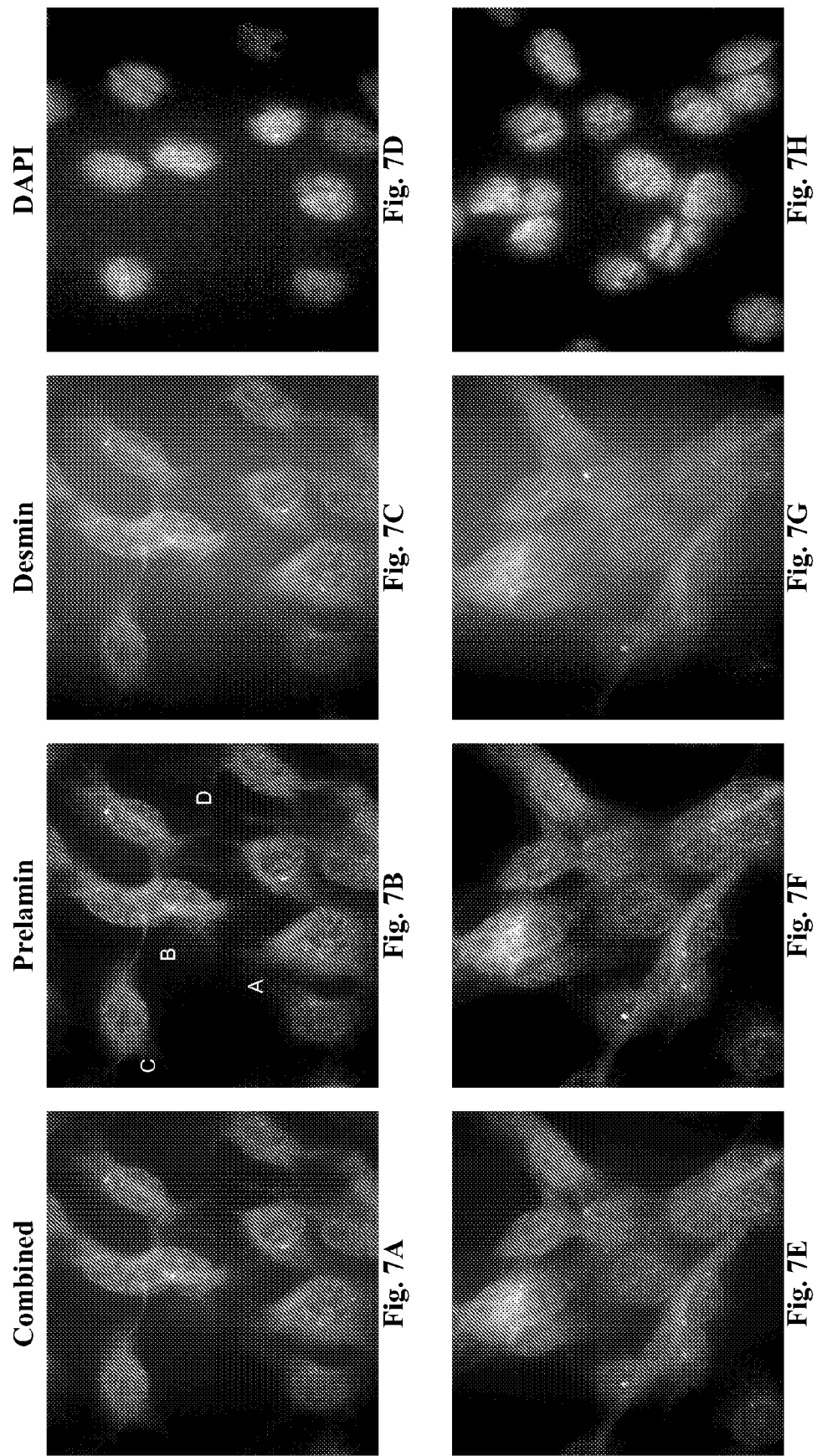

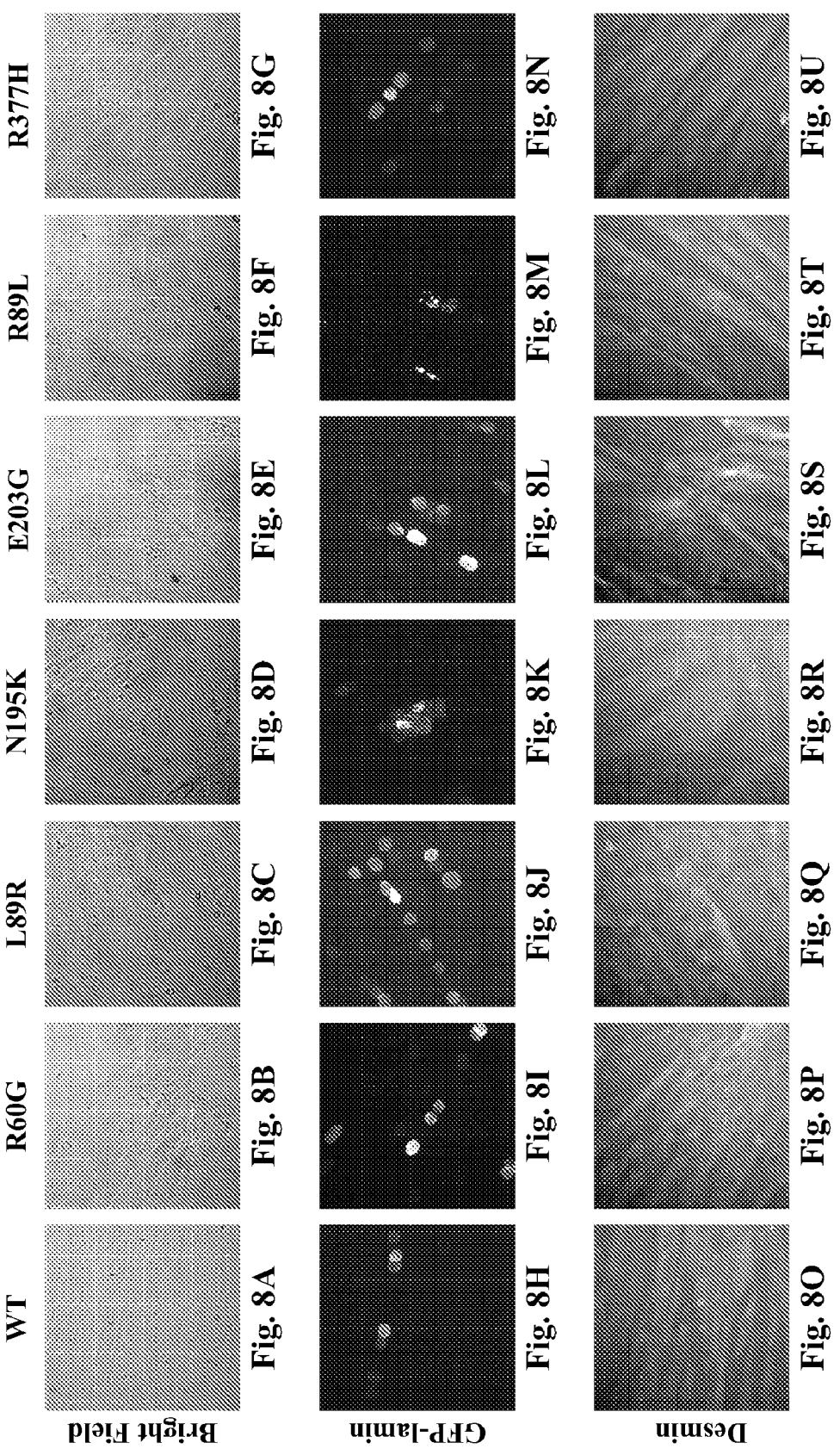

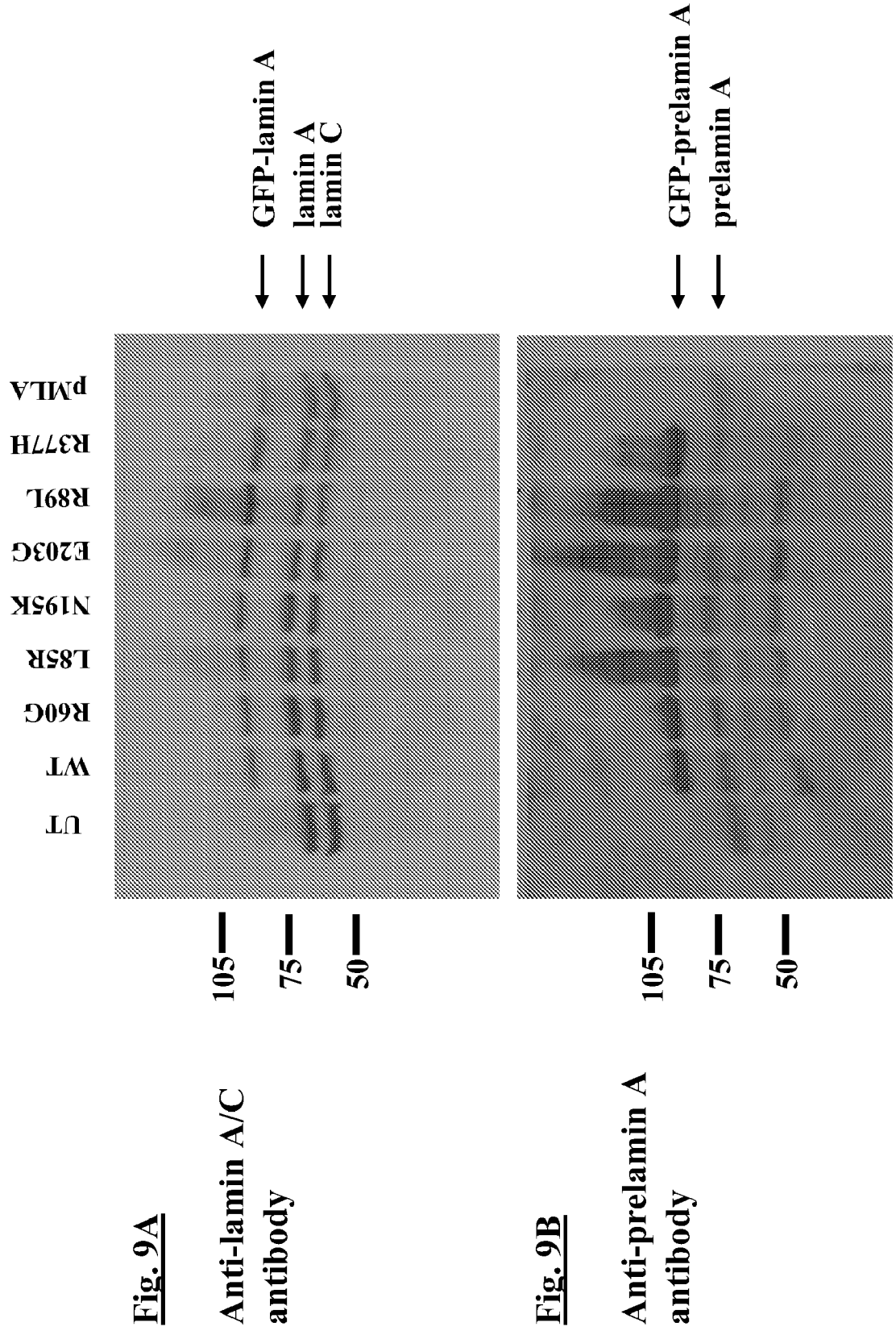

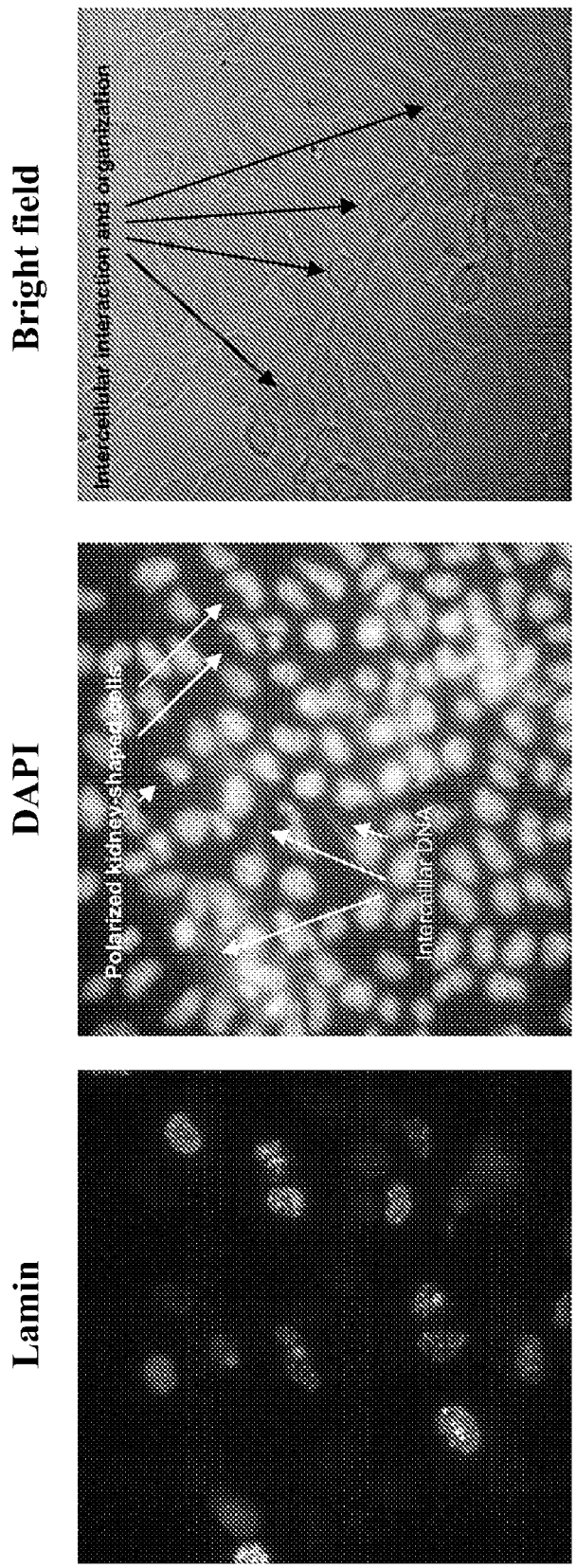

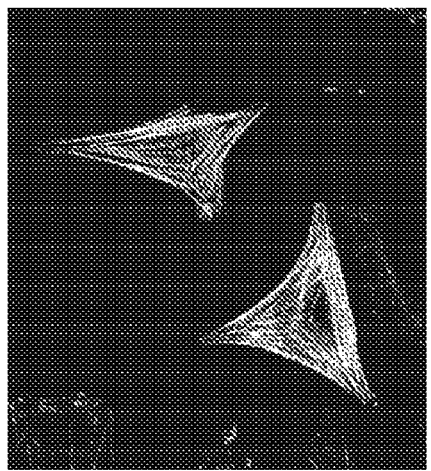
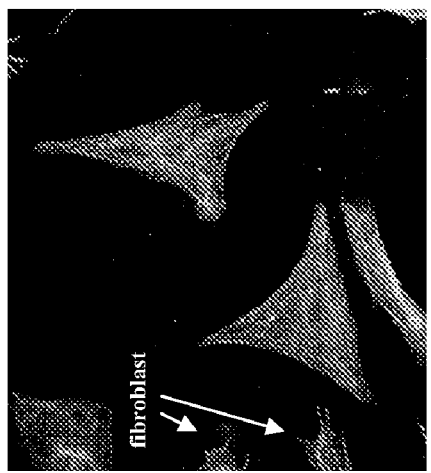
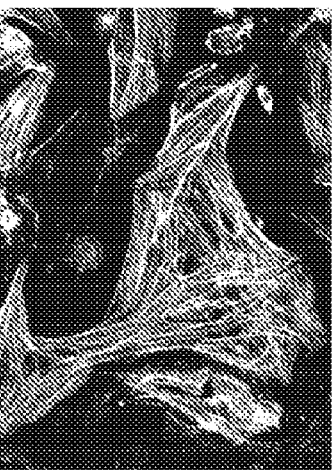
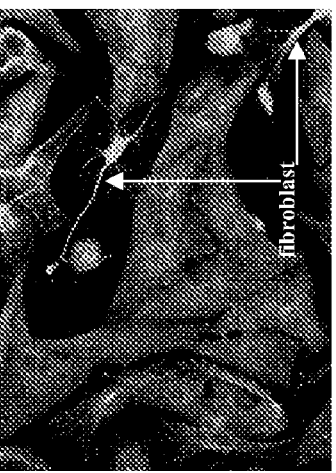

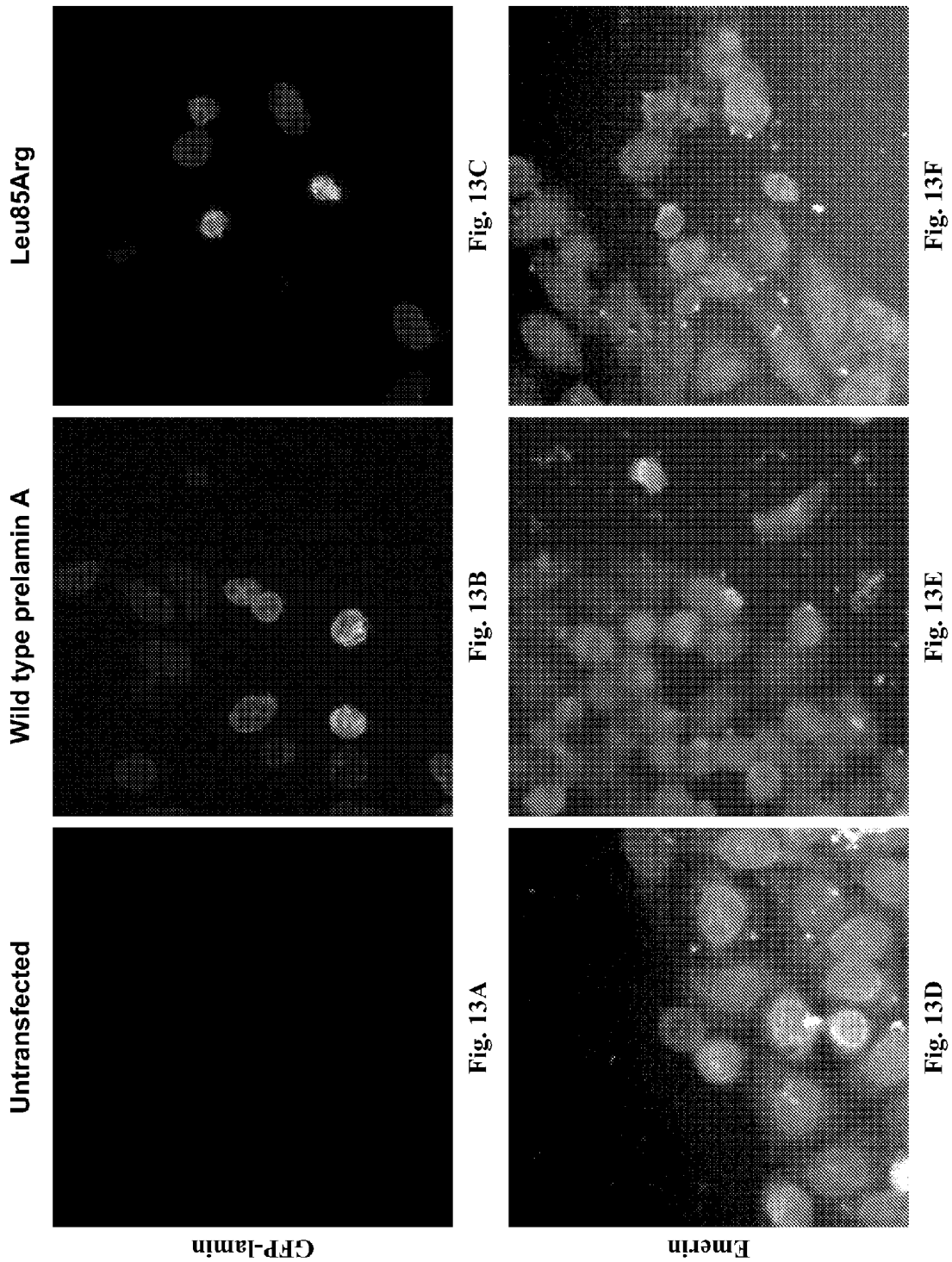

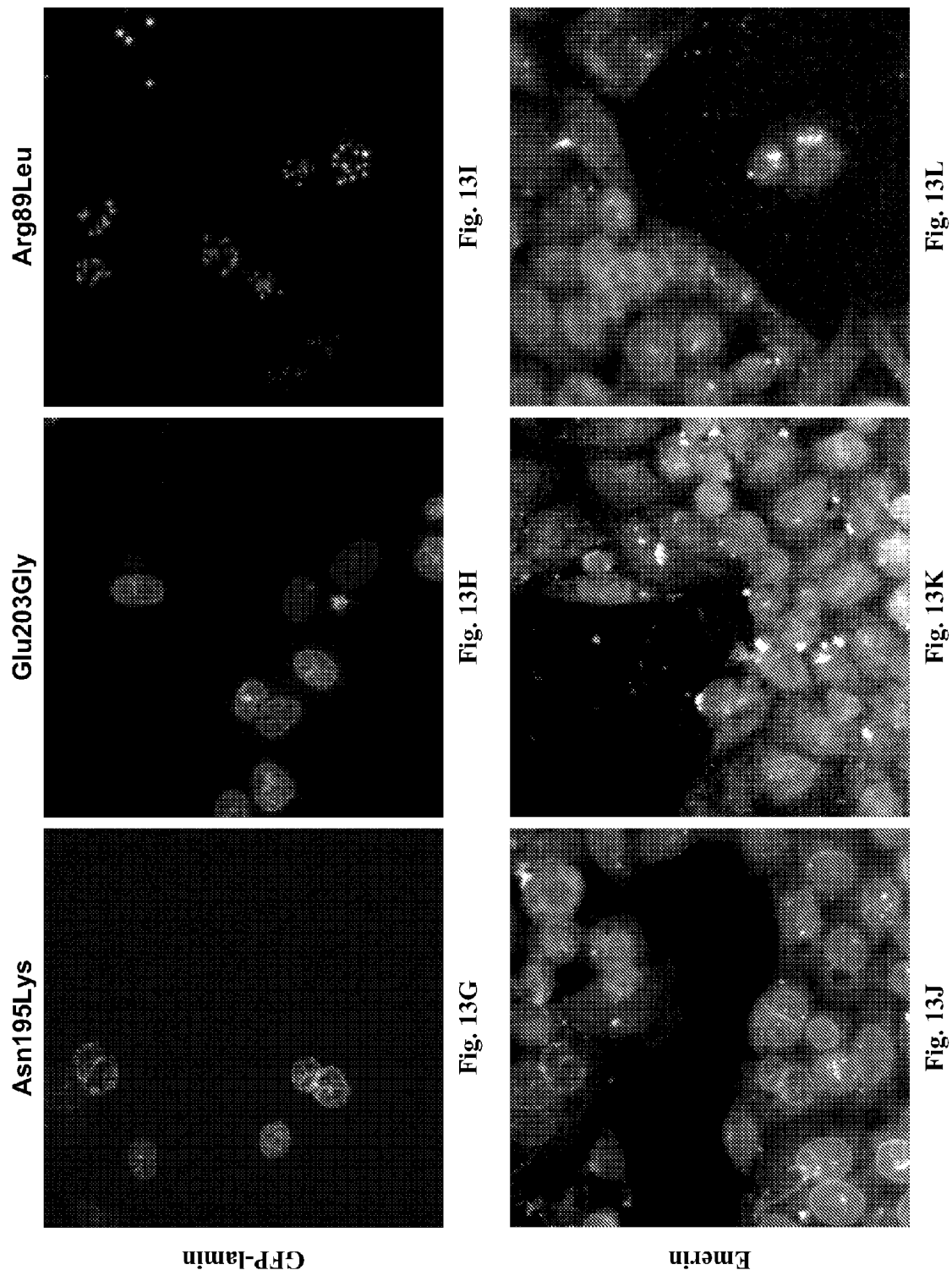

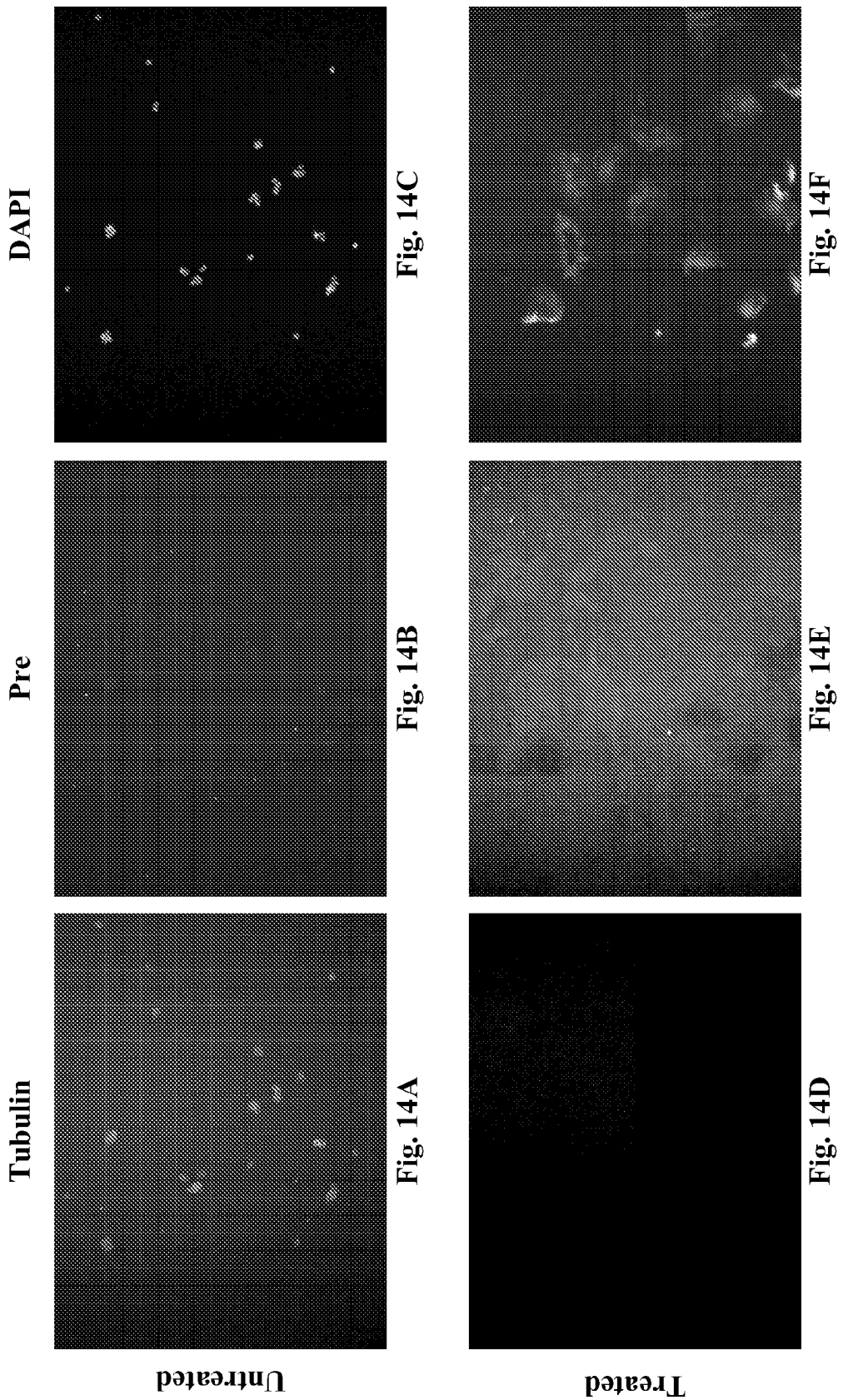

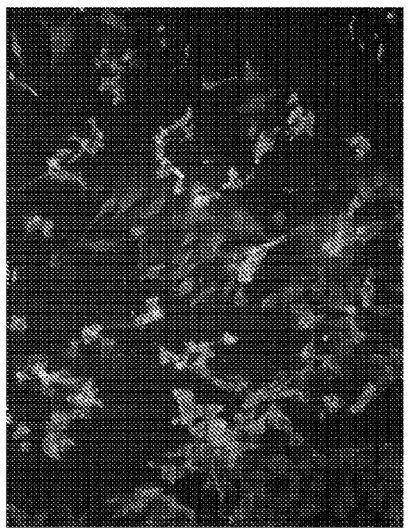
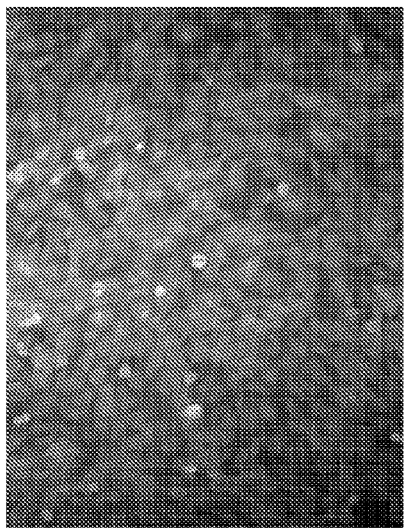
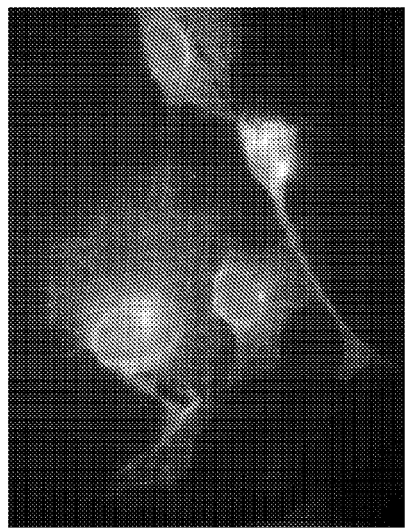
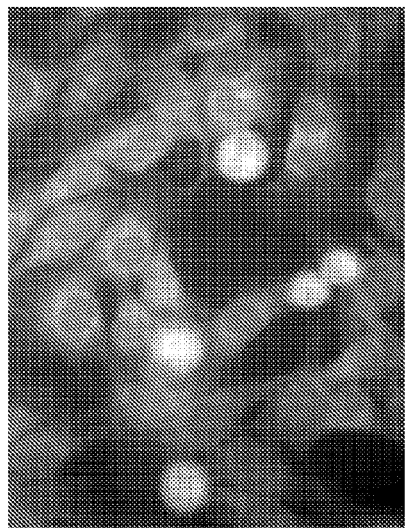
Fig. 15A Control 10X
Fig. 15B Chicken peptide treated 10X
Fig. 15C 40X
Fig. 15D 40X

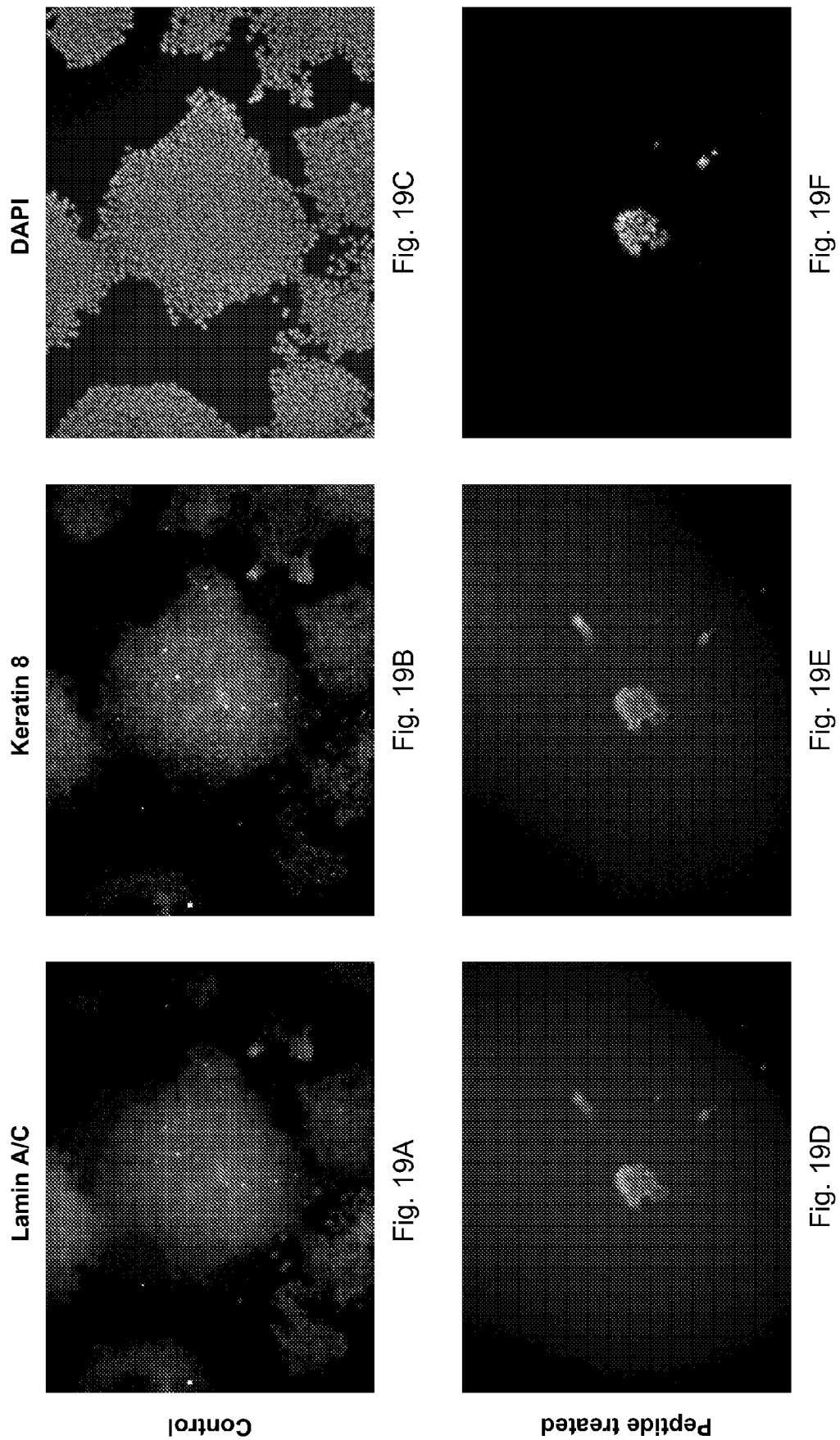

PRELAMIN A PRE PEPTIDE AS A UNIVERSAL STEM CELL DIFFERENTIATION SIGNAL

CROSS REFERENCE TO RELATED APPLICATION

This application is a national stage application under 35 U.S.C. 371 of PCT Application No. PCT/US2007/069790 having an international filing date of May 25, 2007, which designated the United States, which PCT application claimed the benefit of U.S. Application Ser. No. 60/808,722, filed May 26, 2006, the entire disclosure of each of which is incorporated herein by reference.

REFERENCE TO SEQUENCE LISTING

This application contains a Sequence Listing submitted as an electronic text file entitled "2848-53-1-PUS Sequence_Listing_ST25" having a size in bytes of 58 kb, and created Oct. 19, 2011. The information contained in this electronic file is hereby incorporated by reference in its entirety pursuant to 37 CFR §1.52(e)(5).

FIELD OF THE INVENTION

This invention generally relates to products and methods for promoting cell differentiation and the activation of a variety of cellular processes using a prelamin A pre peptide and variants thereof.

BACKGROUND OF THE INVENTION

The nuclear lamina is a meshwork of protein filaments that underlies the nucleoplasmic face of the inner nuclear membrane. This contiguous filamentous scaffolding forms at the nuclear periphery and provides structural support for the nucleus (Newport, 1990). The lamina plays a role in the regulation of gene expression through direct and indirect interactions with transcription factors (Ozaki, 1994). The lamina interacts directly with DNA and is also involved in chromatin organization via direct interactions with histones and other chromatin binding proteins (Gotzmann, 1999). Site-specific phosphorylation of lamina proteins results in the reversible disassembly of the lamina during mitosis (Haas, 1993), and these proteins are also targets of caspase cleavage during apoptosis (Slee, 2001).

The nuclear lamina is composed of intermediate filament proteins called lamins, which are subdivided into two families based on their expression profile and post-translational processing. Expression of the type-A lamins is timed to coincide with cellular differentiation, and expression of these proteins is considered a marker for embryonic stem cell differentiation (Constantinescu, 2006). Furthermore, while one of the A-type lamins, prelamin A, is post-translationally processed by the addition of a fifteen carbon farnesyl group, the covalent modification is later removed and mature A-type lamins lack this covalent modification. The B-type lamins are constitutively expressed in most cell types and are permanently post-translationally modified by the covalent addition of a hydrophobic fifteen carbon chain at the C-terminus, which results in their association with the nuclear membrane (Kitten, 1991). The A- and B-type lamins form heteropolymers and are the major constituents of the nuclear lamina.

Lamins are the oldest members of the intermediate filament family of proteins and, like other intermediate filament proteins, lamins contain a central alpha helical rod domain flanked by non-helical N-terminal and C-terminal domains (FIG. 1). Intercalation of the central alpha helical region is responsible for lamin dimerization, while the domains flanking the central region are involved in higher order lamin filament assembly. Phosphorylation of residues on either side of the alpha helical domain results in the reversible disassembly of the lamina during mitosis. The C-terminal domain of lamins contains a nuclear localization signal as well as a post-translational processing sequence. The two predominant type-A lamins, lamins A and C, are differentially transcribed from the same gene and lamin C differs from the other lamins in that it is essentially a truncated lamin lacking the post-translational processing sequence and containing a small unique C-terminus.

According to accepted theory, lamin C is not post-translationally processed, although other lamin proteins are post-translationally processed via a sequential series of covalent modifications (FIG. 2). Lamin proteins terminate in a CAAX motif (Cysteine, Aliphatic, Aliphatic, X-any), which is the target for post-translational farnesylation, the covalent addition of a fifteen carbon chain to the C-terminal cysteine residue. The farnesylated lamin protein becomes the substrate for an endoprotease which cleaves the protein on the C-terminal side of the modified cysteine residue, releasing the last three amino acids. The now C-terminal farnesylated cysteine residue is then further modified by a carboxymethyltransferase, which adds a methyl group to the end of the protein.

The carboxymethylation of the C-terminal cysteine residue is the final step in the processing of the B-type lamins, and the addition of the aliphatic carbon chain results in the association of the B-type lamins with the nuclear membrane, and the continued association of these proteins with membrane vesicles upon lamina breakdown and reassembly during mitosis. There are approximately twenty other human proteins which are known to also undergo farnesylation, and which are post-translationally processed by these same enzymes. The most noticeable of these proteins is the Ras gene product, the farnesylation of which also results in membrane association and protein activation.

While the post-translational processing of prelamin A proceeds through the same intermediates as the B-type lamins and other farnesylated proteins, prelamin A processing is unique among mammalian proteins as the final step in the maturation of lamin A is the endoproteolytic release of the remaining 15 C-terminal amino acid farnesylated and carboxymethylated peptide (FIG. 2). The function of prelamin A processing has been an enigma since it was first identified, as it seems to run against evolutionary conservation of energy in that extensive energy is used to post-translationally process the C-terminal portion of the peptide, which is subsequently thrown away. Early studies demonstrated that the prelamin A protein remains nucleoplasmic in mitotically arrested cells, and that mature lamin A can only incorporate into the nuclear lamina if the pre sequence is removed (Lutz, 1992; Izumi, 2000). However, if cells are allowed to cycle, the unprocessed prelamin A does incorporate into the lamina by hybridizing with already processed mature lamin A monomers, dimers or tetramers during lamina reassembly. As the previously incorporated phosphorylated mature lamin A protein monomers contain all the information necessary to properly localize and reform the nuclear lamina upon dephosphorylation, the post-translational processing of prelamin A as a method of protein targeting or assembly appeared redundant and no biological effect of replacing prelamin A with mature lamin A was observed in the mammalian cell lines studied.

The lamin A/C cDNA was first cloned and sequenced by Gunther Blobel in 1986 (Fisher, 1986), and early studies demonstrated these proteins were components of the nuclear lamina as well as the nucleoskeleton, the nuclear equivalent of the cellular cytoskeleton. Researchers interested in cholesterol metabolism studied prelamin A processing because the farnesyl group is generated in the cholesterol metabolic pathway. Cancer researchers testing farnesyltransferase inhibitors in Ras-related cancers used prelamin processing as a marker for drug inhibition of the farnesylation pathway.

In 1999, non-X-linked Emery Dreifuss muscular dystrophy (EDMD) was the first human disease identified as being associated with lamin A/C gene mutations (Bonne, 1999). As the X-linked form of EDMD is caused by mutations in emerin, a nuclear membrane protein that directly interacts with lamin A, it was not surprising that lamin A/C mutations could also cause this disease. While EDMD patients suffer from skeletal muscle and connective tissue abnormalities, their greatest heath risk is cardiovascular disease characterized by conduction defects, often necessitating pacemaker implantation.

Later the same year, lamin A/C mutations were also shown to be responsible for inherited forms of dilated cardiomyopathy characterized by conduction defects (Fatkin, 1999). In 2000, the present inventor and colleagues identified lamin A/C mutations as being responsible for dilated cardiomyopathy (DCM) and conduction defects in a family with variable skeletal muscle involvement (Brodsky, 2000). Some of the affected individuals had symptoms of EDMD, while others had indications of limb girdle muscular dystrophy, or no skeletal muscle involvement. Lamin A/C mutations were also shown to cause limb girdle muscular dystrophy, another disease characterized by DCM and conduction defects.

While all of these diseases affect skeletal and/or cardiac muscle, additional diseases were identified as being associated with lamin A/C mutations which did not share this phenotype. Lamin A/C mutations were shown to cause familial partial lipodystrophy, a fat storage disease in which patients typically develop insulin resistance and diabetes (Shackleton, 2000). Lamin A/C gene mutations were then shown to cause neurological and developmental disorders, including mandibuloacryl dysplasia (Novelli, 2002) and Charcot-Marie Tooth Syndrome (De Sandre-Giovannoli, 2002).

The distribution of lamin A/C mutations associated with the same disease as well as different diseases occur throughout the lamin A protein, suggesting that disruption of a particular structural or functional domain is not responsible for the different disease phenotypes. However, in the case of partial lipodystrophy, the mutations do cluster, and evidence has been presented suggesting some of the mutations may interfere with the binding of an adipocyte-specific transcription factor to lamin A (Lloyd, 2002).

Molecular studies of the mutant lamin proteins associated with diseases revealed that some cause obvious alterations in the nuclear lamina structure, with some mutations resulting in the formation of nuclear lamin aggregates (Raharjo, 2001) and/or changes in the cellular distribution of lamina-binding proteins (Mounkes, 2005). An increase in the percent of cells displaying nuclear herniations or "blebs" was also observed in cells expressing the mutant lamin constructs as compared to controls (Raharjo, 2001). While expression of some of the lamin A/C mutations were also shown to result in increased nuclear fragility and altered patterns of gene expression, an explanation for why different mutations affect different tissues and even different subgroups of the same tissue has not been identified. The finding that a lamin A/C knockout mouse shared many of the human disease pathologies (Sullivan, 1999) did not help to delineate why lamin A/C mutations have different tissue-specific effects.

Interest in lamin A/C increased tremendously when mutations in the gene were next found to be the sole cause of the premature aging syndrome Hutchinson-Gilford Progeria Syndrome (HGPS) (Eriksson, 2003). Patients with HGPS display postnatal growth retardation, midface hypoplasia, micrognathia, premature atherosclerosis and coronary artery disease, absence of subcutaneous fat, alopecia, generalized osteodysplasia with osteolysis and pathologic fractures, and the median age of death is 13 years of age. Unlike the other major progeroid syndrome, Werner's syndrome, HGPS is not associated with an increase in age-related cancers or cataracts, indicating that increased DNA mutability or decreased DNA repair is not responsible for the disease pathology as in Werner's syndrome. Instead, an apparent failure of post-natal tissue growth and repair mechanisms results in the striking appearance of premature aging and death.

A common silent mutation in lamin A/C gene resulting in the formation of a cryptic mRNA splice site and internal deletion at the C-terminal end of the prelamin A protein was found in the majority of HGPS patients (Eriksson, 2003). This mutation deletes the cleavage site necessary for the final prelamin A proteolytic processing step, and results in the partially processed prelamin A protein forming nuclear aggregates which result in increase in nuclear herniations, or "blebbing".

Based on these findings, a commonly accepted model has been proposed in which prelamin A farnesylation targets the partially processed protein to the nuclear membrane where further processing releases the mature lamin A protein to incorporate into the nuclear lamina. In HGPS, the partially processed farnesylated prelamin A in the nuclear membrane causes nuclear blebbing, which is then proposed to cause all of the associated disease pathologies. However, nuclear blebbing has never been shown to be associated with any pathology seen in HGPS patients, or as interfering with any physiological process. Furthermore, an increase in nuclear blebbing results from expression of lamin A mutations which cause DCM and not HGPS. Nonetheless, drug trials have recently been reported in which farnesyltransferase inhibitors (FTIs) were used to inhibit prelamin aggregation and nuclear blebbing in vitro (Mallampalli, 2005; Toth, 2005; Yang, 2005), and in a mouse model of HGPS (Fong, 2006). However, while some improvement was observed when animals were treated with FTIs, a percentage of animals still displayed all of the disease phenotypes examined, and the authors conclude that blocking prelamin A processing would not cure the disease (Fong, 2006).

Therefore, there remains a need in the art to identify the molecular mechanisms responsible for the disease pathologies associated with lamin A/C mutations and/or dysfunction and to use the knowledge of the mechanisms to design therapeutic strategies for preventing and treating such diseases.

SUMMARY OF THE INVENTION

One embodiment of the invention relates to a method to induce differentiation of a cell, comprising contacting the cell with prelamin A pre peptide, or a functional homologue or analog thereof, wherein contact of the cell with the prelamin A prepeptide induces differentiation of the cell. The method can be performed in vitro, in vivo, and/or ex vivo.

The cell to be contacted can include virtually any cell, including differentiated and non-differentiated cell types, and including an adult stem cell or an embryonic stem cell. In one aspect, the cell is a mesodermal stem cell, an endodermal stem cell, or an ectodermal stem cell. In one aspect, the cell can include, but is not limited to, a neural stem cell, a hematopoietic stem cell, a mesenchymal stem cell, an epithelial stem cell, an intestinal stem cell, a skin stem cell, an osteoblast stem cell, a liver stem cell, a lung stem cell, a cardiac muscle stem cell, a skeletal muscle stem cell, a pancreatic stem cell, or an adipocyte stem cell. In one embodiment, the cell is a differentiated or a differentiating cell, including a differentiated or differentiating cell of any of the above-described stem cells. In one embodiment, the cell is a cancer cell (tumor cell).

In one aspect of this embodiment, the method further includes adding growth and/or differentiation factors to the cell to direct the terminal differentiation of the cell.

Yet another embodiment of the invention relates to a method to generate a population of cells, a tissue or an organ in vitro or ex vivo, comprising contacting a stem cell that is a precursor for a cell in the population of cells or of the tissue or organ, with a prelamin A pre peptide, or a functional homologue or analog thereof, under effective culture conditions, to induce differentiation of the cell and the formation of the population of cells, the tissue or the organ. In one aspect, the method further includes introducing the population of cells, the tissue or the organ into an individual in need of the cells, tissue or organ. In one aspect, such an individual has a disease or condition selected from: dilated cardiomyopathy, Emery-Dreifuss muscular dystrophy, limb-girdle muscular dystrophy, partial lipodystrophy, axonal neuropathy, mandibuloacral dysplasia, Charcot-Marie Tooth Syndrome, Hutchinson-Gilford Progeria Syndrome (HGPS), lipodystophy, diabetes, and primary and metastatic cancers. In one aspect, the individual is in need of the cells, tissue or organs to improve a cosmetic appearance.

Yet another embodiment of the invention relates to a method to induce regeneration or repair of a damaged or degenerated tissue or organ, comprising administering to the tissue or organ a prelamin A pre peptide, or a functional homologue or analog thereof.

Another embodiment of the invention relates to a method to stimulate tissue growth, comprising administering to the tissue or cells in the tissue a prelamin A pre peptide, or a functional homologue or analog thereof.

Another embodiment of the invention relates to a method to treat a disorder associated with tissue or organ damage or degeneration, comprising administering to the subject with the disorder a prelamin A pre peptide, or a functional homologue or analog thereof.

Yet another embodiment of the invention relates to a method to protect a subject from a condition or disorder associated with (although not necessarily caused by) lamin A/C mutations, comprising administering to a subject with a lamin A/C mutation a prelamin A pre peptide, or a functional homologue or analog thereof.

Another embodiment of the invention relates to a method to promote fertility in a mammal, comprising administering to a mammal a prelamin A pre peptide, or a functional homologue or analog thereof.

Another embodiment of the invention relates to a method to promote the fertilization of a gamete, comprising contacting the gamete with a prelamin A pre peptide, or a functional homologue or analog thereof, under conditions where fertilization of the gamete can occur.

Yet another embodiment of the invention relates to a method to slow the aging process and improve normal organ and tissue morphology and/or physiology in a mammal, comprising administering to the mammal, or to a cell, tissue or organ of the mammal, a prelamin A pre peptide, or a functional homologue or analog thereof.

Another embodiment of the invention relates to a method to repair or enhance the repair of a bone fracture and/or improve bone physiology, comprising administering to osteoblast stem cells, or to the site of a bone fracture, a prelamin A pre peptide, or a functional homologue or analog thereof.

Another embodiment of the invention relates to a method to improve joint physiology, comprising administering to a joint or the synovial fluid of a joint, a prelamin A pre peptide, or a functional homologue or analog thereof.

Yet another embodiment of the invention relates to a method to treat cancer, comprising administering to tumor cells a prelamin A pre peptide, or a functional homologue or analog thereof, under conditions effective to cause fusion and apoptosis of the tumor cells.

Another embodiment of the invention relates to a method to treat cancer, comprising administering to tumor cells a prelamin A pre peptide, or a functional homologue or analog thereof, under conditions effective to cause differentiation of the tumor cell and subsequent arrest of growth and division of the tumor cell.

Another embodiment of the invention relates to a method to treat a neurological condition, comprising administering to neural stem cells or damaged nerve cells a prelamin A pre peptide, or a functional homologue or analog thereof, under conditions effective to cause differentiation of the neural stem cells into nerve cells.

In any of the above embodiments, in one aspect, the prelamin A pre peptide is selected from: (a) a peptide consisting essentially of SEQ ID NO:2, SEQ ID NO:16, SEQ ID NO:17, SEQ ID NO:18 or SEQ ID NO:19; (b) a biologically active fragment of SEQ ID NO:2, SEQ ID NO:16, SEQ ID NO:17, SEQ ID NO:18 or SEQ ID NO:19; (c) a peptide consisting essentially of an amino acid sequence that is at least about 70% identical to SEQ ID NO:2, SEQ ID NO:16, SEQ ID NO:17, SEQ ID NO:18 or SEQ ID NO:19, wherein the peptide has the biological activity of SEQ ID NO:2, SEQ ID NO:16, SEQ ID NO: 17, SEQ ID NO:18 or SEQ ID NO:19; and/or (d) a peptide consisting essentially of an amino acid sequence that differs from SEQ ID NO:2 by at least one substitution, deletion or insertion of an amino acid residue at a position of SEQ ID NO:2 selected from the group consisting of: 1, 2, 5, 6, 9, 10, 11, 12, 13 and 14, wherein the peptide has the biological activity of SEQ ID NO:2. In one aspect, the prelamin A pre peptide consists essentially of an amino acid sequence that is at least about 80% identical to SEQ ID NO:2, SEQ ID NO:16, SEQ ID NO:17, SEQ ID NO:18 or SEQ ID NO:19. In one aspect, the prelamin A pre peptide consists essentially of an amino acid sequence that is at least about 90% identical to SEQ ID NO:2, SEQ ID NO:16, SEQ ID NO:17, SEQ ID NO:18 or SEQ ID NO:19. In one aspect, the prelamin A pre peptide consists essentially of an amino acid sequence that differs from SEQ ID NO:2 by at least one substitution, deletion or insertion of an amino acid residue at a position of SEQ ID NO:2 selected from the group consisting of: 1, 2, 5, 6, 9, 10 and 11. In one aspect, the prelamin A pre peptide consists essentially of SEQ ID NO:2, SEQ ID NO:16, SEQ ID NO:17, SEQ ID NO:18 or SEQ ID NO:19. In one aspect, the prelamin A pre peptide consists essentially of SEQ ID NO:2.

In one aspect of any of the above embodiments, the prelamin A pre peptide comprises a modification selected from farnesylation, carboxymethylation, geranyl-geranylation, and complexing with a lipid carrier.

In one aspect of any of the above embodiments, the prelamin A pre peptide or functional homologue or analog thereof is provided in a composition comprising at least one pharmaceutically acceptable carrier.

In one aspect of any of the above embodiments, the prelamin A pre peptide is provided as a nucleic acid molecule comprising a nucleic acid sequence encoding the peptide.

In another aspect, of any of the above embodiments, the prelamin A pre peptide is administered ex vivo.

Yet another embodiment of the invention relates to a method to tag or identify stem cells from a tissue, comprising: (a) contacting a tissue with a labeled prelamin A pre peptide; and (b) identifying cells that incorporate the labeled prelamin A pre peptide. In one aspect, the method further includes a step of isolating the stem cells identified in (b).

Another embodiment of the invention relates to a method to identify and isolate stem cells from a tissue, comprising: (a) contacting a tissue with a prelamin A pre peptide or a functional homologue or analog thereof; (b) identifying cell types that differentiate when contacted with the peptide or functional homologue or analog thereof; and (c) isolating the type of cells identified in (b) from an undifferentiated cell population or tissue.

Yet another embodiment of the invention relates to a to identify genes that are expressed during cell differentiation, comprising: (a) contacting stem cells with prelamin A pre peptide or functional homologue or analog thereof; and (b) identifying genes that are differentially regulated in the stem cells after contact with the peptide or functional homologue or analog thereof as compared to in the absence of contact with the peptide or functional homologue or analog thereof.

Another embodiment of the invention relates to a method to identify compounds that regulate prelamin A pre peptide-induced cell differentiation, comprising: (a) contacting stem cells with prelamin A pre peptide or functional homologue or analog thereof in the presence and absence of a putative regulatory compound, wherein in the absence of the putative regulatory compound, the stem cells will differentiate when contacted with the prelamin A pre peptide or functional homologue or analog thereof; and (b) detecting a change in the differentiation of the stem cells in the presence of the putative regulatory compound as compared to in the absence of the putative regulatory compound, wherein detection of a change in the differentiation of the stem cells indicates that the compounds regulate prelamin A pre peptide-induced cell differentiation.

Yet another embodiment of the invention relates to a method to identify compounds that regulate cell differentiation, comprising: (a) contacting an isolated prelamin A processing-deficient cell with a test compound for regulation of cell activation and differentiation; and (b) detecting whether the test compound regulates an activity in the cell selected from the group consisting of: prelamin A processing, prelamin A pre peptide transport, and cell differentiation, as compared to in the absence of the test compound.

In either of the above embodiments of a method to identify compounds, in one aspect, the test compound is selected from: a homologue of prelamin A pre peptide with putative prelamin A pre peptide biological activity; a pharmaceutical compound with putative prelamin A pre peptide biological activity; a homologue of prelamin A with putative prelamin A biological activity; a candidate protein for a prelamin A processing enzyme, or a gene encoding the candidate protein; a candidate protein for a downstream prelamin A pre peptide signal transduction protein, or a gene encoding the candidate protein; and a putative pharmaceutical compound for use in the treatment of a disorder.

Another embodiment of the invention relates to the use of a prelamin A pre peptide, or a functional homologue or analog thereof, in the preparation of a composition or formulation for use in a method of any preceding claim.

Yet another embodiment of the invention relates to the use of a prelamin A pre peptide, or a functional homologue or analog thereof, in a method of any preceding claim.

Another embodiment of the invention relates to the use of a prelamin A pre peptide, or a functional homologue or analog thereof, in the preparation of a composition or formulation for use in inducing differentiation of a cell.

Another embodiment of the invention relates to a method to selectively deliver a compound to multiple cells of a tissue, comprising: (a) linking a compound to a prelamin A protein or a biologically active fragment thereof; (b) delivering the compound-prelamin A protein conjugate to a stem cell for a tissue of interest; and (c) activating the stem cell by contacting the cell with prelamin A peptide, or a biologically active homologue or analog thereof. In one aspect, steps (a)-(c) are performed ex vivo, and wherein the method further comprises implanting the cell into a recipient animal. In another aspect, the compound-prelamin A protein conjugate, or a nucleic acid molecule encoding the conjugate, is delivered to the cell by in vivo administration. Such a nucleic acid molecule can include, but is not limited to, a viral vector. In one aspect, the compound is linked to prelamin A in a recombinant fusion protein. In one aspect, the stem cell is a muscle stem cell and the tissue is muscle tissue.

Yet another embodiment of the invention relates to a method to enhance stem cell differentiation, comprising contacting a cell with prelamin A or a homologue or biologically active fragment thereof. In one aspect, the cell is additionally contacted with prelamin A pre peptide.

Another embodiment of the invention relates to a method to enhance stem cell differentiation, comprising contacting a cell with Zmpste24 or a biologically active homologue or analog thereof.

BRIEF DESCRIPTION OF THE DRAWINGS OF THE INVENTION

FIG. 1 is a schematic drawing showing lamin structural organization.

FIG. 2 is a schematic drawing showing lamin processing. The sequence indicated in FIG. 2 corresponds to positions 646 (Y) to 664 (M) of SEQ ID NO:4. The CAAX motif is shown corresponding to the CSIM motif in FIG. 2, corresponding to positions 661-664 of SEQ ID NO:4. A carbon chain comprising 15 carbons is indicated by the chain of Cs.

FIG. 3 is an alignment of the amino acid sequence of the pre peptide portion of prelamin A from 5 different animal species, and further shows the sequence of the yeast a-factor sequence.

FIGS. 4A-4D are digitized images showing that prelamin A pre peptide induces differentiation of C2C12 myoblasts (FIG. 4A=untreated control; FIG. 4B=peptide treated at 6 hours; FIG. 4C=peptide treated, formation of sheets at 72 hours; FIG. 4D=peptide treated, formation of myotubes at 72 hours).

FIGS. 5A-5C are digitized images showing that prelamin A pre peptide treatment of H9c2 cells induces differentiation of cardiac myoblasts (FIG. 5A=untreated control; FIG. 5B=peptide treated excreting extracellular matrix at 6 hours; FIG. 5C=peptide treated forming tissue sheets at 48 hours).

FIGS. 5D-5F are digitized images of a Western blot showing that peptide-treated H9c2 cells show modest increases in lamin A/C (FIG. 5D) and prelamin A (FIG. 5E) expression and an increase in the myogenic transcription factor myogenin (FIG. 5F).

FIGS. 6A-6L are digitized images showing that prelamin A is involved in organizing chromatin, and forms a cytoskeleton and extracellular matrix during myoblast differentiation (FIGS. 6D-6F illustrate prelamin staining; FIGS. 6G-6I illustrate desmin staining; FIGS. 6J-6L illustrate DAPI staining; FIGS. 6A-6C illustrate combined staining).

FIGS. 7A-7H are digital images showing that prelamin A processing appears timed to coincide with cell polarization and the formation of a prelamin A-desmin cytoskeleton and extracellular matrix (FIGS. 7B and 7F illustrate prelamin staining; FIGS. 7C and 7G illustrate desmin staining; FIGS. 7D and 7H illustrate DAPI staining; FIGS. 7A and 7E illustrate combined staining).

FIGS. 8A-8U are digitized images showing nuclear disorganization, aberrant myotube morphology and intercellular disorganization of mouse C2C12 skeletal myoblasts transfected with wild type (WT) and mutant GFP-prelamin A fusion protein constructs and differentiated for two days by serum starvation (Bright field microscopy (FIGS. 8A-8G), direct fluorescence microscopy (FIGS. 8H-8N), and indirect immunofluorescence microscopy with an anti-desmin antibody (Sigma) (FIGS. 8O-8U) are shown).

FIGS. 9A and 9B are digitized images of Western blots of lamin A and lamin C (FIG. 9A), and prelamin A (FIG. 9B) expression in C2C12 cells expressing wild type prelamin A and prelamin A proteins containing disease mutations.

Figure 1:
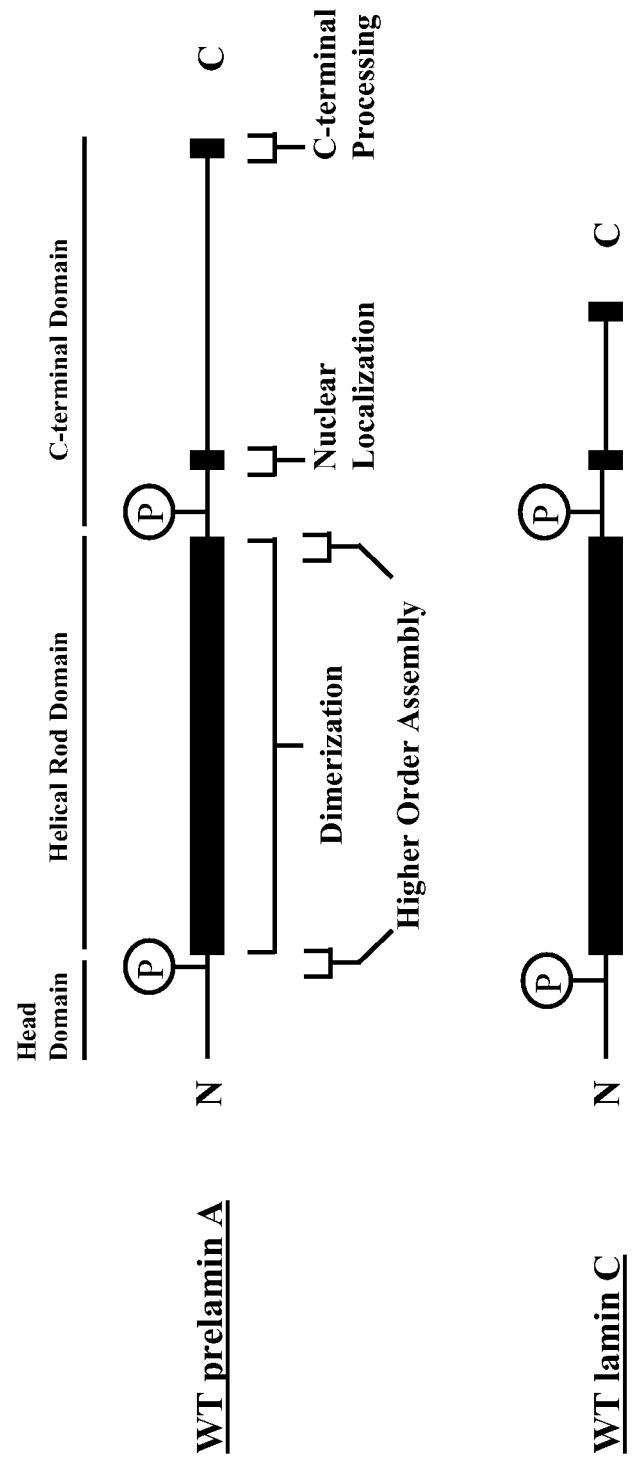
Figure 2:
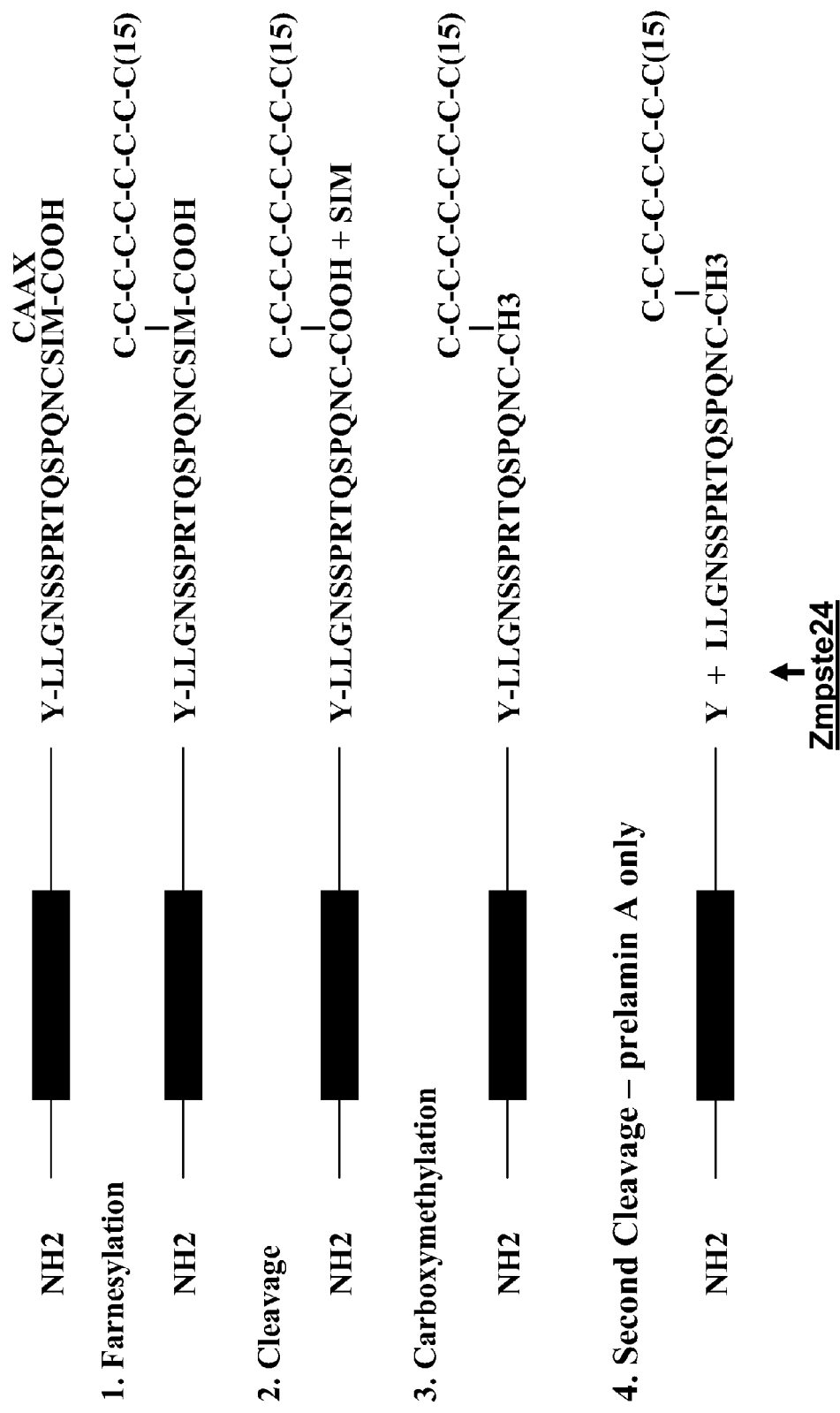
Figure 10A:
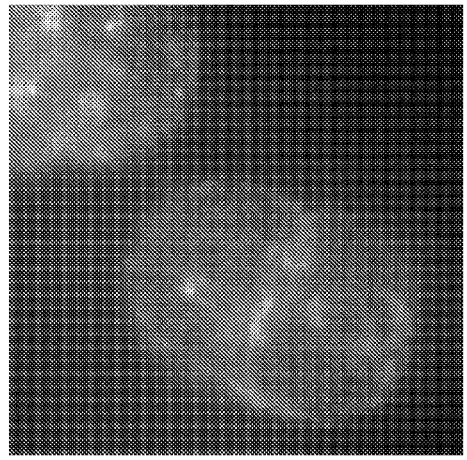
FIGS. 10A-10D are digitized images showing (FIGS. 10A-10D) mouse F9 teratocarcinoma cells transfected with the GFP-prelamin A fusion protein containing the Arg60Gly mutation (FIGS. 10A-10B) and the Arg89Leu prelamin A processing mutation (FIGS. 10C-10D).

FIGS. 10E-10G are digitized images showing that expression of GFP-prelamin A containing the Asn195Lys mutation results in interaction of cells expressing the mutant GFP construct, as well as the untransfected cells around them (FIG. 10E=lamin staining; FIG. 10F DAPI staining; FIG. 10G=bright field microscopy).

Figure 10B:
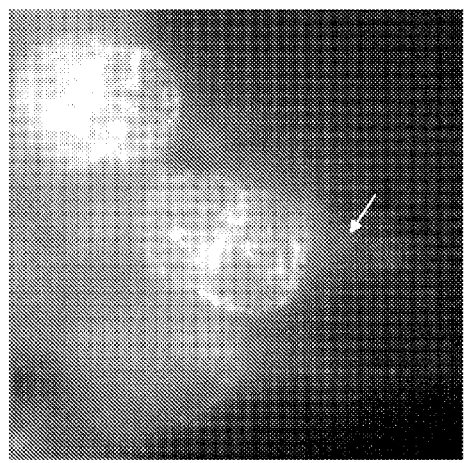
Figure 10C:
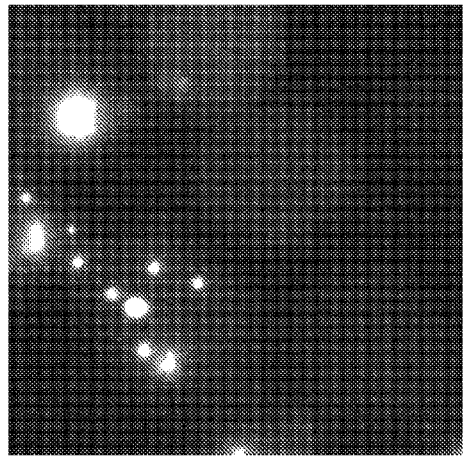
Figure 10D:
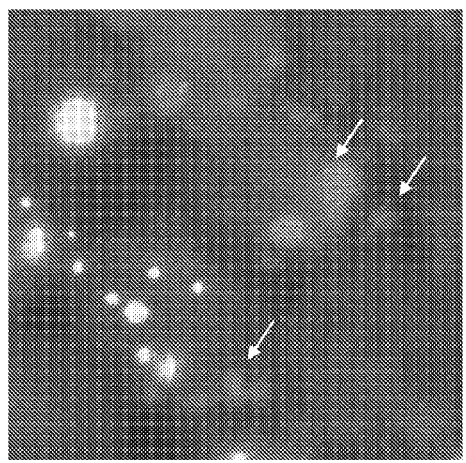
Figure 10H:
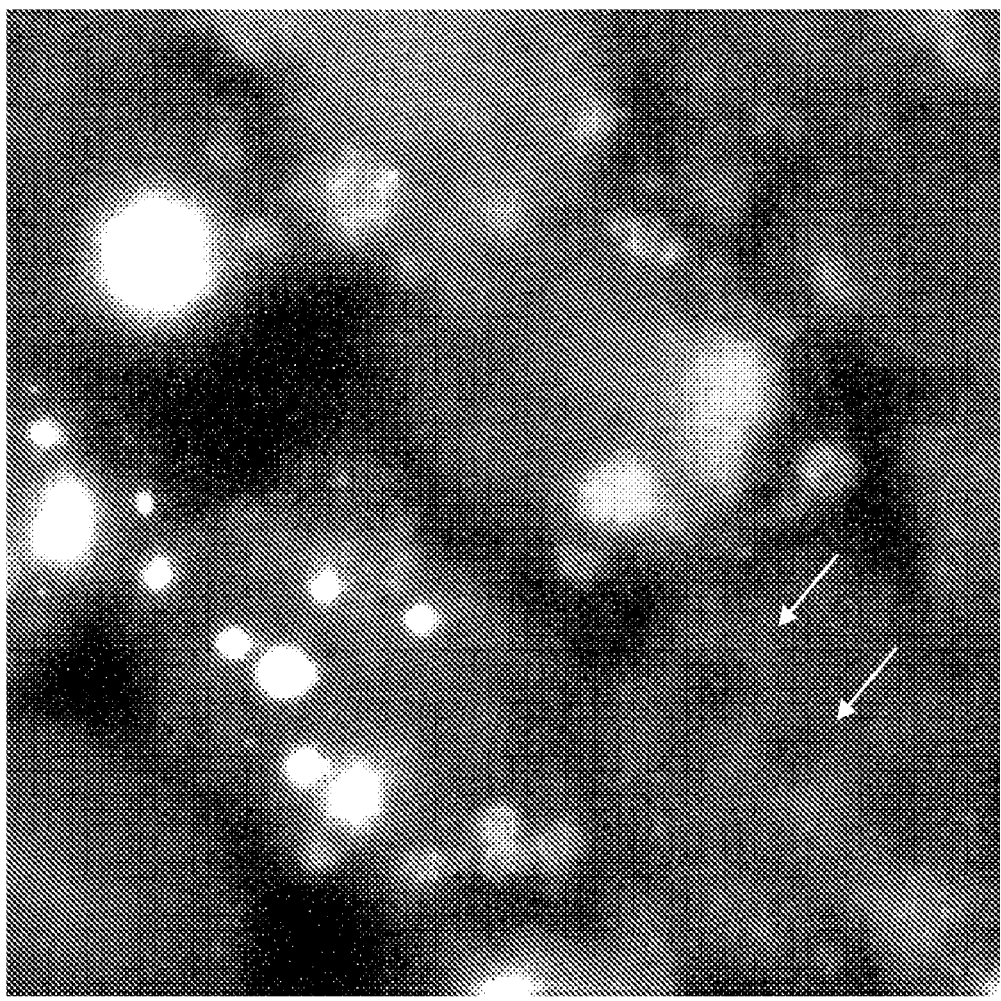

FIG. 10H is a digitized image showing the keratin staining and GFP-lamin expression pattern in differentiating cells expressing the Asn195Lys mutation.

Figure 11B:
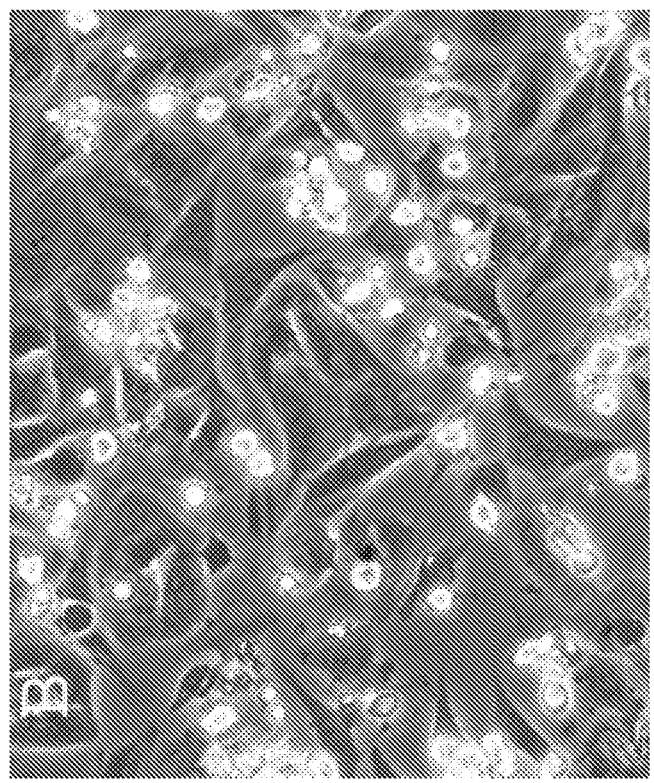
Figure 11A:
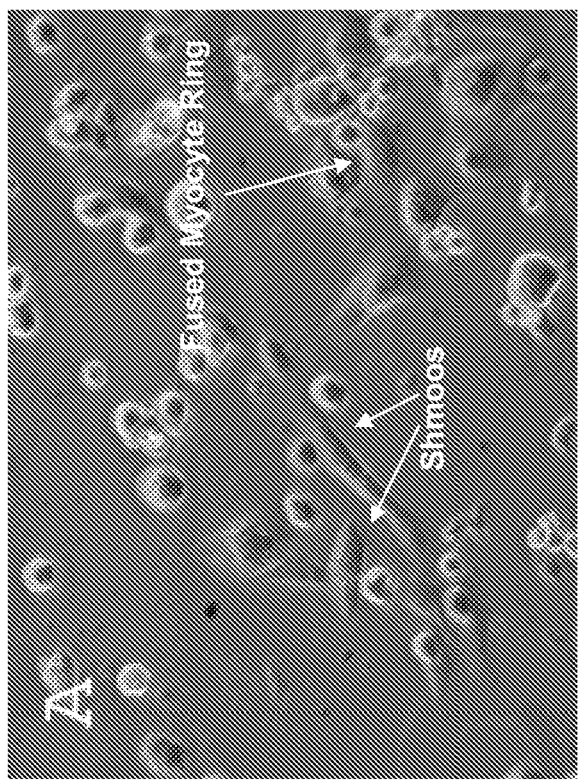

FIGS. 11A and 11B are digitized images showing that prelamin A pre peptide induces morphogenesis and interaction of neonatal rat cardiac myocytes (NRMCs) at 6 hours (FIG. 11A) and 18 hours (FIG. 11B).

FIGS. 12A-12F are digitized images showing that at 72 hours after exposure to prelamin A pre peptide, NRMCs have fused into beating myosheets and reorganized their cytoskeletons (as illustrated by staining for tubulin cytoskeleton (FIGS. 12A and 12D), actin cytoskeleton (FIGS. 12B and 12E) and the combined staining (FIGS. 12C and 12F).

FIGS. 13A-13F are digitized images showing human HeLa cervical carcinoma cells transfected with GFP-prelamin A fusion protein constructs (FIGS. 13B, 13C, 13E and 13F) and stained for emerin (FIGS. 13D-13F).

FIGS. 13G-13L are digitized images showing human HeLa cervical carcinoma cells transfected with additional GFP-prelamin A fusion protein constructs (FIGS. 13G-13L) and stained for emerin (FIGS. 13J-13L).

FIGS. 14A-14F are digitized images showing that prelamin A pre peptide induces differentiation of embryonic stem cells (FIGS. 14A-14C show a 10× control; FIGS. 14D-14F show peptide treated cells after 6 hours), staining for tubulin (FIGS. 14A and 14D), pre peptide (FIGS. 14B and 14E) and DAPI (FIGS. 14C and 14F)).

FIGS. 15A-15D are digitized images showing that chicken prelamin A pre peptide induces differentiation of murine C2C12 myoblast cells (control=FIGS. 15A and 15C; peptide treated=FIGS. 15B and 15D).

Figures 16A, 16B:
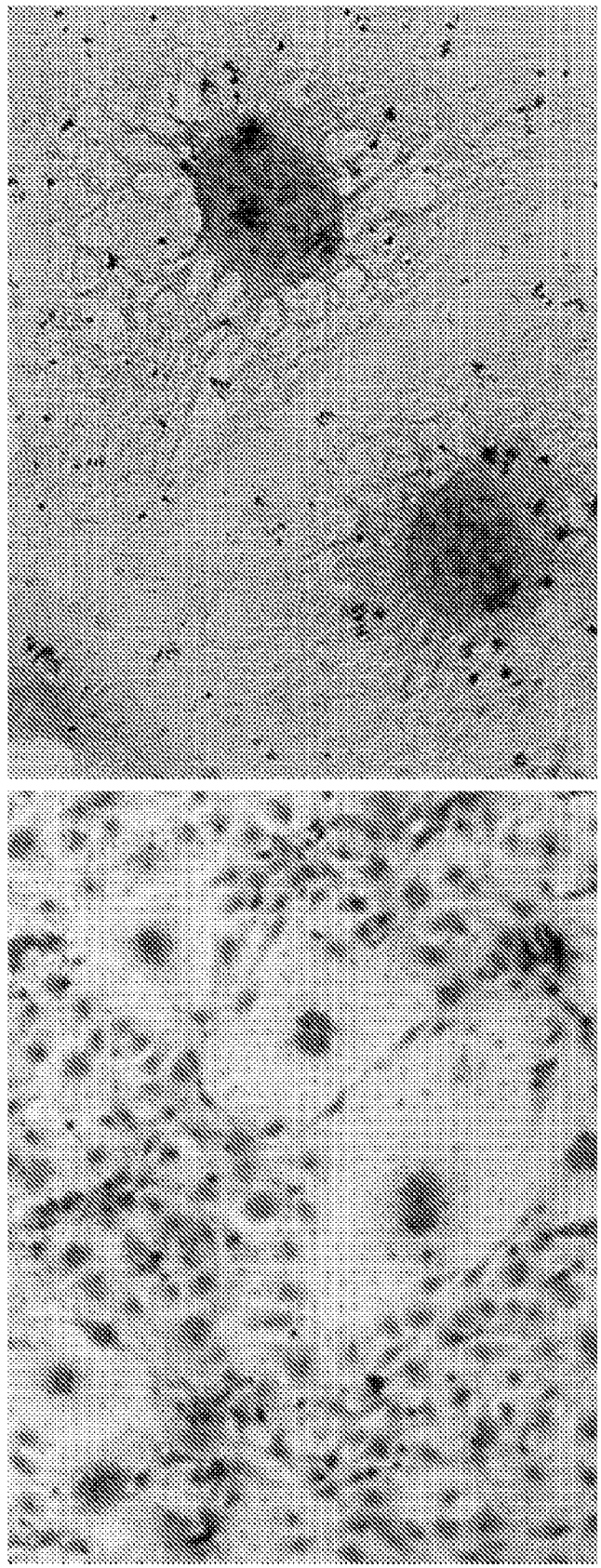

FIGS. 16A and 16B are digitized images showing that the prelamin A peptide induces differentiation of preadipocytes (FIG. 16A is 10×; FIG. 16B is 60×).

Figure 17:
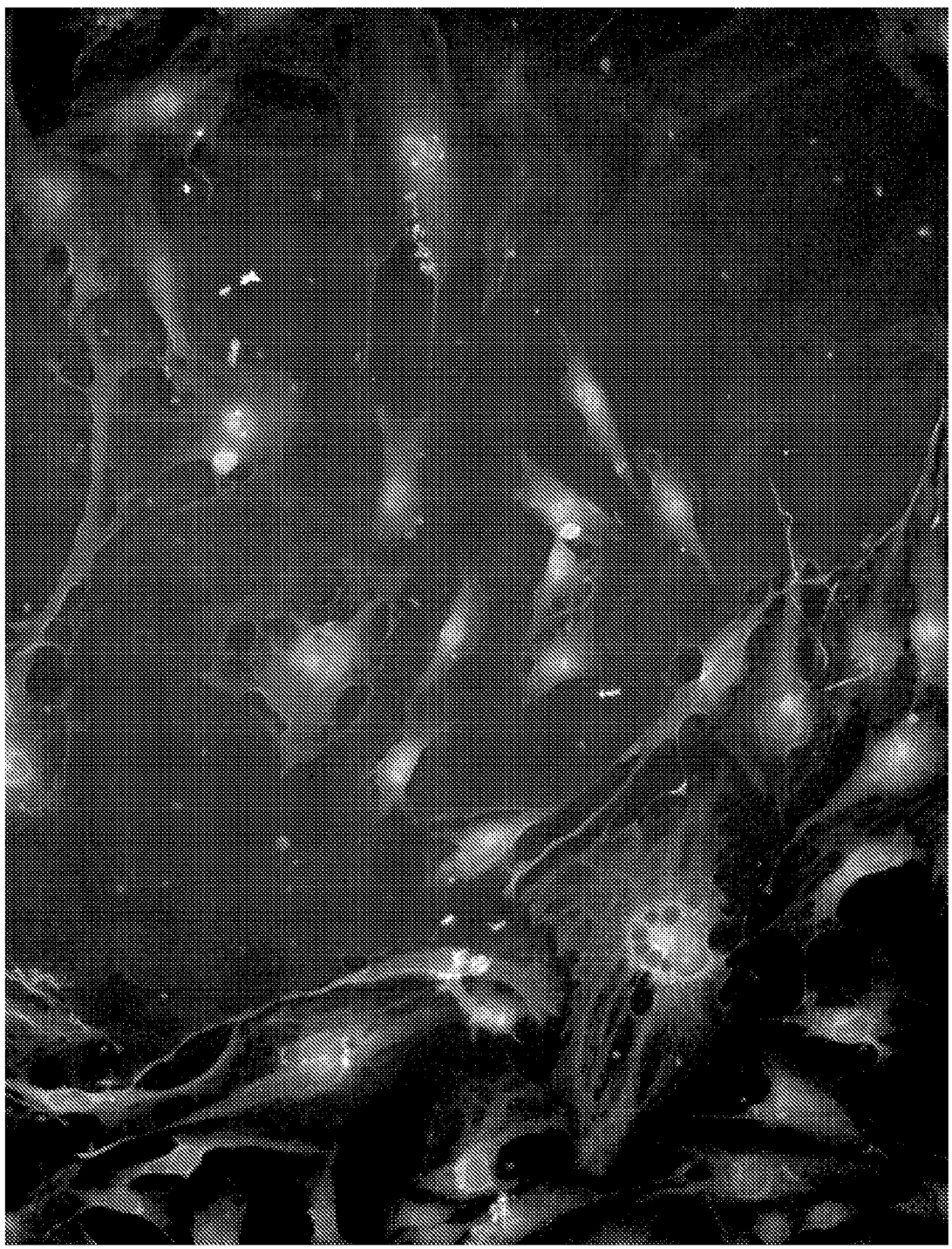

FIG. 17 is a digitized image showing that prelamin A pre peptide induces differentiation toward multiple different cell types, the interaction of different cell types and tissue formation.

Figure 18A:
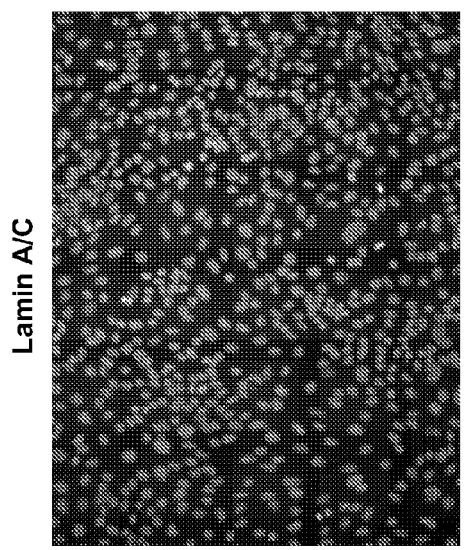
Figure 18B:
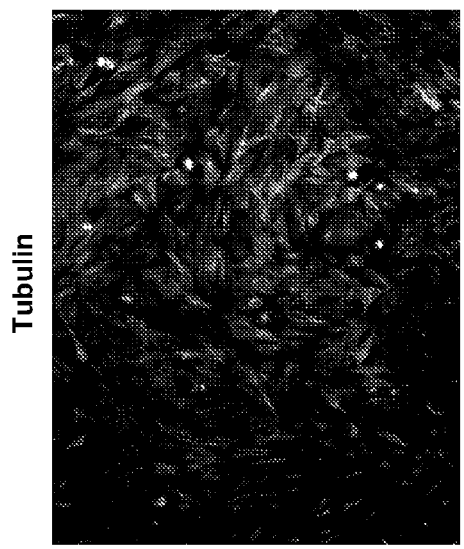
Figure 18C:
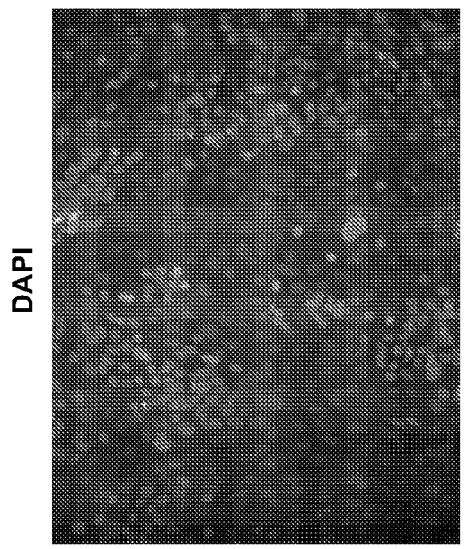
Figure 18D:
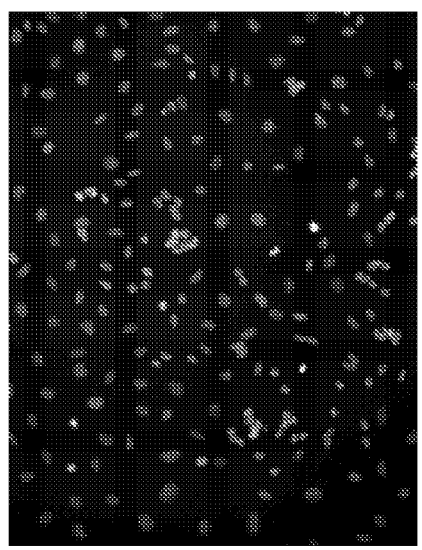
Figure 18E:
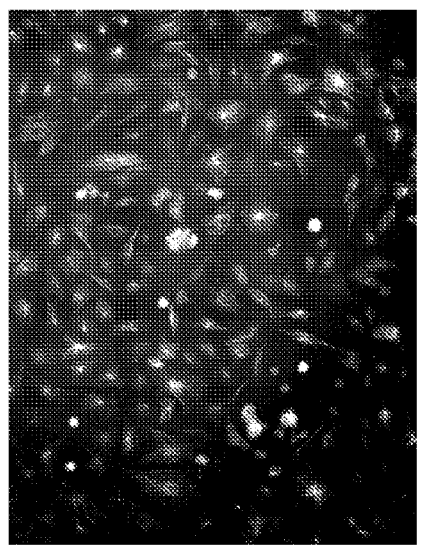
Figure 18F:
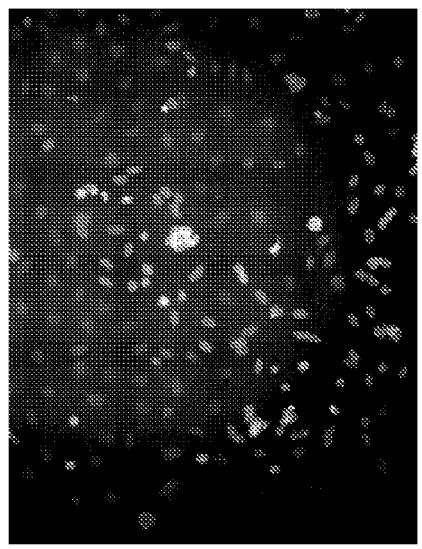

FIGS. 18A-18F is a digitized image showing that prelamin A pre peptide induces differentiation of neural stem cells toward mature neural cells, including glial cells (lamin A/C expression=FIGS. 18A and 18D; tubulin expression=FIGS. 18B and 18E, and DAPI FIGS. 18C and 18F).

FIGS. 19A-19F is a digitized image showing that prelamin A pre peptide induces differentiation of embryonic carcinoma cells (lamin A/C expression=FIGS. 19A and 19D; keratin expression=FIGS. 19B and 19E, and DAPI=FIGS. 19C and 19F).

DETAILED DESCRIPTION OF THE INVENTION

The present invention relates to the discovery by the present inventor that the farnesylated and carboxymethylated C-terminal peptide of prelamin A, also referred to herein as the prelamin A pre peptide, is a universally conserved stem cell differentiation signal for tissue growth and repair.

The inventor has previously demonstrated that defects in prelamin A processing causes severely aberrant cardiac and skeletal myocyte differentiation, and that the "pre" sequence of prelamin A functions as a signaling molecule when proteolytically released from the prelamin A protein. More particularly, the inventor previously demonstrated that the "pre" sequence of prelamin A indicates the proximity and direction of mononucleate myoblasts during differentiation and cell fusion to generate multinucleate myocytes, and has described a method of using this peptide to promote myoblast activation and differentiation and for the growth and repair of cardiac and skeletal muscle tissue, as well as for the treatment of cardiac and skeletal muscle disorders. The inventor had previously discovered that the "pre" peptide of prelamin A serves an analogous function to that of the S. cerevisiae a-type mating factor or a-type mating pheromone, which is the only known protein that is processed in a similar manner to prelamin A. The present inventor's data indicated that the "pre" sequence of prelamin A functions as a signaling molecule when proteolytically released from the prelamin A protein. Therefore, lamin A/C mutations affecting prelamin A processing, "pre" signaling, or lamin polymerization will result in disease.

The present inventor has now made the surprising discovery that the ability of the prelamin A pre peptide to induce differentiation extends beyond cardiac and muscle tissue to reveal this peptide as a universally conserved stem cell differentiation signal for tissue and organ growth and repair. The experimental data described herein first confirm that prelamin A processing functions exactly as the inventor's previous studies indicated, including to regulate the incorporation of prelamin A and mature lamin A into the extracellular, cytoskeletal and nuclear lamina of differentiating muscle cells. Second, the data presented herein unexpectedly and significantly move beyond the prior results to show that the activity of prelamin A pre peptide is extended generally to any cells (i.e., the activity of the peptide is not limited to muscle cells).

In particular, the data presented herein show that the extensively post-translationally modified C-terminal peptide of prelamin A is the highly active, universally (or evolutionarily) conserved, stem cell differentiation signal for organ growth and repair, and not simply a waste product of lamin A maturation. Furthermore, application of the peptide to stem cells has revealed that the function of prelamin A and lamin A incorporation into the nuclear lamina during stem cell differentiation establishes cell morphology and tissue architecture. These experiments have also revealed that prelamin A forms cytoskeletal and extracellular matrices and is directly involved in determining cell morphology and tissue architecture. Importantly, the inventor has shown that the prelamin A pre peptide can induce differentiation of post-embryonic and embryonic stem cells, opening up a wide range of applications for this peptide and for functional analogs thereof.

The prelamin A pre peptide, as well as functional variants and analogs thereof, represents a profoundly significant platform compound for the treatment of heart disease, muscular dystrophy, and bone degeneration, as well as other genetic and non-genetic problems affecting these tissues. The peptide and its analogs will improve heart, muscle and bone function during aging and extend human lifespan. In addition, given the discovery by the present inventor as set forth herein, the peptide and its analogs will induce growth and repair of many other tissues and organs, extending the use of this peptide as a platform compound for the treatment and/or prevention of a wide variety of diseases and conditions, as well as a tool for the manipulation of biological processes including fertility and aging. The peptide causes changes in cell morphology and intercellular organization in differentiated and non-differentiated cell types.

Therefore, this peptide, analogs thereof, and related molecules identified by its application, usher in a new era of tissue and organ engineering and repair at the molecular level, and impact areas from therapeutic treatment of disease, to novel tissue/organ engineering, to fertility, to modulation of the aging process. The present inventor has already demonstrated the creation of novel living tissues in the laboratory, which are described below. These tissues may be used to treat a variety of disorders, for organ, tissue and cell creation and repair, for research purposes including, but not limited to, toxicity testing, and for commercial production processes. These processes also represent new methods for drug delivery and other patient treatment and laboratory procedures.

In addition to the above-discoveries, the present inventor has discovered that under certain conditions, application of the prelamin A pre peptide and/or its analogs results in a form of cell death, a property which has significant promise in treating cancer. For example, the present inventor has shown that the prelamin A pre peptide induces fusion of closely spaced myoblasts into a syncicium which eventually results in cell death, and as such, the peptide represents a promising treatment for myosarcoma, or muscle cancers. Furthermore, because the peptide appears to be capable of fusing multiple different cell types, it is proposed herein that the peptide can be used as a general treatment to induce fusion and death of cancer cells, and to produce different hybrid cell lines for commercial, medical, and/or research use. In addition, because tumor cells may also be undifferentiated stem cells that have lost the signal to properly differentiate and consequently display uninhibited growth, without being bound by theory, the present inventor believes that contact of tumor cells with prelamin A pre peptide will cause the tumor cell to differentiate and consequently arrest growth and division. Application of the prelamin A pre peptide by the inventor caused the arrest and aggregation of neuroblastoma (data not shown) and embryonic carcinoma cells (Example 10, FIG. 19), demonstrating its application in cancer treatment.

Furthermore, the specific effect that the prelamin A pre peptide and/or its analogs can have on intercellular organization indicates that it also has significant applications in human and animal fertility.

More particularly, as described in detail herein, the inventor has confirmed his previous findings by first showing that the prelamin A pre peptide can induce the differentiation of myoblasts in vitro, and that the peptide induces the formation of an extensive intra- and extracellular matrix in the differentiating cells. Surprisingly, the induction of differentiation occurred within minutes of contact with the peptide and in the absence of conventional differentiation factors or cell confluence (conditions that would normally prevent differentiation). The peptide was further demonstrated to cause rapid and extensive muscle fiber formation through induction of cell cycle arrest, tissue-specific gene expression, and cellular morphogenesis and fusion (i.e., all three pathways known to direct muscle cell differentiation). Much of the differentiation process occurred in vitro in the presence of the prelamin A pre peptide within hours, a process that normally takes days in vitro and that occurs only after stem cells are confluent and placed in a differentiation medium. Moreover, the prelamin A pre peptide induced myoblast differentiation at micromolar and even nanomolar concentrations. Together, these results indicate that the prelamin A pre peptide is a native signal for mammalian myoblast migration and differentiation.

In the course of the experiments described herein, the inventor has now identified both the prelamin A protein and the muscle-specific intermediate filament protein desmin, as downstream signals of prelamin A pre peptide-induced morphogenesis and intercellular organization. Just 6 hours after prelamin A pre peptide exposure, prelamin A forms intra- and intercellular matrices, and desmin expression is either upregulated or redistributed with desmin protein co-localizing with the nuclear lamina in all differentiating myoblasts. The inventor's results show that a desmin gradient is involved in the recruitment of new cells to the myotube, and that intra- and extracellular desmin filaments whose arrangement is based on the intra- and extracellular lamin architecture (FIGS. 6 and 7) are involved in the organization and movement of nuclei into myotubes (FIG. 4). Without being bound by theory, the present inventor proposes herein that while desmin is a muscle-specific intermediate filament protein, the concomitant expression of prelamin A and tissue-specific cytoskeleton-forming intermediate filament proteins at the time of cellular differentiation in nearly all cell types indicates that other intermediate filament family members play an analogous role to desmin in hybridizing to and replicating the lamina architecture in the cytoskeleton and extracellular matrix of non-muscle cell types. Direct evidence for this observation is provided herein in the investigation of the effects of prelamin A pre peptide in F9 teratocarcinoma cells, where the intermediate filament cytoskeleton which forms upon cellular differentiation is composed of keratin 8 (FIGS. 10A-10D). Also, the present inventor has observed changes in lamin and cytoskeletal architecture in HeLa cervical carcinoma cells that are communicated to adjacent cells from cells transfected with the different GFP mutants (FIGS. 13A-13L).

The present inventor has also now demonstrated that prelamin A pre peptide differentiates or dedifferentiates (i.e., changes the cytoskeletal morphology) neonatal rat cardiac myocytes (NRMCs). After treatment with the peptide for just six hours, some of the NRMCs appeared to be shmooing like mating yeast responding to an a-factor gradient, and showed an elongated morphology, and a number of cells were fused. Significantly, after 72 hours of exposure to the peptide, the NRMCs had fused into beating myosheets. The peptide also induced fusion/cross-talk between different cell types, as demonstrated by tubulin cytoskeletal rearrangements occurring at the site of interaction between an NRMC and an adjacent fibroblast. Consequently, the present inventor proposes herein that the prelamin A pre peptide not only determines tissue organization amongst the same type of cells, but also directs the intracellular organization between different cell and tissue types. Furthermore, the ability of the prelamin A peptide to induce morphogenesis and interaction of fibroblasts in these experiments demonstrates that prelamin A peptide function extends beyond muscle cell types. Homogeneous cultures of fibroblasts also underwent structural reorganization when exposed to the prelamin A peptide.

The present inventor has now also generated viable living heart tissue outside of the body for what is believed to be the first time. Indeed, this is believed to be the first time that any true, living tissue has been induced to form in vitro from stem cells. Specifically, treatment of H9C2 cardiac myoblasts with the prelamin A pre peptide produced ground breaking results. Unlike skeletal myoblasts which fuse to form myotubes, cardiac myocytes are single cells interconnected by a filamentous extracellular meshwork, or matrix. However, under previously known laboratory conditions, cardiac myoblasts could only be induced to form multinucleate myotubes more similar to skeletal myocytes than mono- and binucleated cardiac muscle tissue. While not sharing morphological features with true cardiac myocytes or heart muscle tissue, these cells were considered to be cardiac myoblasts because the differentiating myotubes they form express heart-specific as opposed to skeletal muscle proteins. In contrast to prior results with these cells in vitro, when the present inventor contacted these cardiac myoblasts with the prelamin A pre peptide, the peptide induced extracellular matrix formation within 5 minutes, which was clearly evident at 6 hours. At 48 hours, instead of fusing into myotubes, the peptide had induced the cardiac myoblasts to remain as healthy single cells, and to have differentiated into myocytes, excreted an interconnecting extracellular desmin matrix, and formed viable living muscle tissue, which is believed to be viable living cardiac muscle tissue, for the first time in the laboratory. The myocytes are mononucleate and binucleate like true cardiac myocytes. Vertical striations can be seen forming higher order intra and intercellular structures. There was overall cellular disorganization, which was due to the supply of the peptide at a homogeneous concentration and not in a gradient, although the cells do appear to be organizing in the more dense region of the field, where the striations are observed, indicating that the differentiating myocytes have the inherent capacity to become properly organized.

The ability of the prelamin A peptide to induce secretion of extracellular matrix as discovered herein is a novel and important observation with significant applications in treating normal and disease-related aging. Perhaps as significant as the senescense of cells themselves is the weakening and breakdown of intercellular interactions that occurs with age. This weakening of the intercellular tissue matrix is readily apparent in the case of skin, resulting in the outward appearance of aging as characterized by such features as increased lines and wrinkles. Consequently, the results described herein demonstrate that the prelamin A peptide will not only induce the differentiation of adult stem cells to functionally replace aging cells in tissues and organs, but will also induce stem cells to excrete extracellular matrix which will structurally strengthen and rejuvenate tissues and organs.

Furthermore, the present inventor demonstrates herein that when adult rabbit cardiac myocytes (i.e., differentiated cells) were treated with the prelamin A pre peptide, cytoskeletal rearrangements were induced, and there was a dissolution of the actin cytoskeleton. This result demonstrates the peptide can induce morphogensis and restructuring of differentiated cells and tissues.

Because prelamin A pre peptide can correctly direct the appropriate differentiation of different cell precursors, these experiments together have demonstrated that the prelamin A pre peptide is not a non-specific signal for cell fusion, but instead is the universally conserved signal for stem cell activation and differentiation leading to embryonic and adult tissue growth and repair.

As further described herein, the present inventor has now shown that the prelamin A pre peptide can induce the differentiation and morphogenesis of preadipocytes (Example 7), neural stem cells (Example 9) and embryonic carcinoma cells (Example 10). In the case of neural cells, the prelamin A pre peptide-treated cells were larger than the controls, more widely spaced, were interacting around certain loci and had undergone morphogenesis and taken on the appearance of nerve cells, including glial cells. In embryonic carcinoma cells, the prelamin A peptide-induced inhibition of cell proliferation, changes in lamin A/C and keratin 8 expression, cell morphogenesis, DNA expansion and alteration of intercellular organization.

The present inventor has now also shown that the prelamin A pre peptide can induce differentiation of embryonic stem (ES) cells. In particular, after 6 hours of treatment with the peptide, the DNA morphology in the ES cells changed drastically, there was no longer any tubulin expression, and there was extensive secretion of the pre peptide. Since tubulin is required for chromosomal segregation, these cells are likely to be cell cycle arrested, as would appear to be the case based on the DNA morphology. The change in DNA morphology, concomitant change in gene expression, apparent cell cycle arrest and secretion of the pre peptide in response to peptide treatment all indicate the peptide was inducing differentiation of these ES cells.

The experiments described herein also show that the application of the prelamin A pre peptide has also induced the formation of novel tissue sheets containing a variety of cell types that are interacting (Example 8, FIG. 17). Cell morphology indicates the prelamin A peptide induces the formation of osteoclasts, cells involved in bone growth and regeneration, as well as neural cell types with axonal extensions, and intercellular vessels.

The present inventor has also now demonstrated that the highly divergent prelamin A peptide homologue of chicken (as compared to human prelamin A pre peptide) can induce the differentiation of mouse skeletal myoblasts (Example 6) and preadipocytes (Example 7, FIG. 16). These findings demonstrate that signaling information contained in the human, mouse and chicken prelamin A pre peptides has been retained during the evolution of the primary amino acid sequences encoding these peptides. These results also show that the human prelamin A peptide can tolerate a considerable number of conservative and non-conservative substitutions, insertions and/or deletions and retain activity, and that the chicken prelamin A peptide and mouse prelamin A peptide (and predictably those of other species) share many of the applications of the human prelamin A peptide.

The present inventor has also discovered that a granular signal detected with a prelamin A antibody in a micrograph of the nuclei forming connections with each other in the experiments described herein is prelamin A (i.e., as opposed to the pre peptide). This data demonstrates that GFP-prelamin A moves between nuclei and is not limited to nuclear domains. This leads the inventor to propose herein significant additional roles for prelamin A itself. First, these data indicate that prelamin A is very likely to be involved in signaling and differentiation itself, most likely as a downstream effector of the signal generated by the pre peptide, although one signal may propagate the other. Second, transcription factors and other regulatory molecules are also known not to be limited to nuclear domains, and since lamin A binds transcription factors, the junctions between nuclei are, without being bound by theory, likely to be the way in which transcription factors signal and travel between nuclear domains, possibly piggybacking onto prelamin A. Therefore, the present inventor proposes that one can transfect a myoblast or other stem cell with prelamin A, or a virus containing it, or any protein or viral or DNA expression system, and then activate the stem cell with the prelamin A pre peptide and inject the construct or protein, the result will be delivery of the protein or DNA to untreated tissue.

Application of the prelamin A peptide has led the present inventor to also discover that prelamin A itself is involved in forming previously unobserved extranuclear cytoskeletal and intercellular matrices during cellular differentiation (FIGS. 6 and 7). This role for prelamin A in establishing cell and tissue architecture explains why different lamin A/C mutations affect different tissues and tissue sub-groups. Furthermore, the finding that the tissue-specific intermediate filament desmin hybridizes to the nascent prelamin A cytoskeleton indicates that, like the laminopathies which cause heart and skeletal muscle disease, the desminopathies result in heart and skeletal muscle disease by interfering with normal myocyte differentiation and stem cell-based tissue growth and repair. Furthermore, these findings indicate that the many forms of heart disease with adult onset are due to defects in stem cell based tissue growth and repair, as opposed to defects in force generation and transmission as current models suggest. Consequently the ability of the prelamin A peptide to induce cardiac and skeletal myoblast differentiation will have broad applications in the treatment of different forms of heart disease and skeletal muscle dystrophy.

The present inventor has also demonstrated that both cardiac and skeletal myoblasts share the common feature of being the first cell lines examined to contain unprocessed prelamin A, as well as a previously unidentified "prelamin C" splice variant (FIGS. 5D, 5E and 9A-9B). The observation that only mature lamin C has been observed in somatic cell types indicates that prelamin C can serve as an additional source for the prelamin A peptide. (In addition, the identification of prelamin C as a source for the pre peptide explains why mice lacking prelamin A appear normal (JCI March 2006; 116(3):743-52. LG Fong et al)).

In total, and as described in more detail below, the present inventor has made a startling discovery that opens a multitude of applications in the areas of tissue growth and repair. Prior to the present invention, in the area of tissue repair, even relatively simple human cell types were grown on plastic surfaces, and then the cell-layered plastics were implanted into patients for the development of tissue in vivo. However, the present inventor has now generated living cardiac muscle tissue in the laboratory for the first time, and these cardiac muscle sheets are ready to be used for the repair of injured and diseased hearts. In addition to inducing heart muscle stem cells to form living cardiac muscle sheets for the first time, the prelamin A pre peptide has induced skeletal myoblasts to differentiate in minutes into novel myotubes and sheets, and to form intermediates never before seen. Furthermore, the peptide has induced neonatal rat cardiac myocytes to form living, beating cell rings, and adult rabbit cardiac myocytes have been induced to undergo morphogenesis and restructuring. The peptide has induced mitotic arrest and differentiation of preadipocytes, neural stem cells, fibroblasts, embryonic carcinoma and embryonic stem cells.

The identification of the peptide as the native signal for adult muscle stem cell activation is not only a groundbreaking discovery for heart, muscle and bone disease treatment, but the discovery by the present inventor that the activity of the prelamin A pre peptide extends to other tissues represents a landmark in the understanding of and ability to manipulate stem cell function, cellular differentiation, and tissue and organ formation. As discussed above, the present invention relates to the use of the prelamin A pre peptide and functional variants and analogs thereof, as well as compositions and fusion proteins comprising this compound, and molecules identified through the application of the prelamin A pre peptide, in tissue and organ engineering and repair at the molecular level. Importantly, the use of the prelamin A pre peptide is not limited to the induction of differentiation processes in skeletal and cardiac muscle cells, as the present inventor has demonstrated herein that the prelamin A pre peptide is a universal signal for cell differentiation.

Accordingly, the present invention relates to the use of prelamin A pre peptide and/or functional variants or analogs thereof to treat any disease or condition where the differentiation of cells and/or the repair, regeneration and/or generation of tissues or organs would be beneficial. The present invention also relates to the use of the prelamin A peptide to strengthen and rejuvenate tissues and organs in cosmetic applications, and to control the size and/or appearance of tissues for health and/or cosmetic purposes (e.g. muscle size for personal appearance preferences and/or sports applications, and controlling fat for weight/health and/or appearance). The present invention also relates to the use of prelamin A pre peptide and/or functional variants or analogs thereof to engineer tissues and/or organs in vitro, ex vivo, or in vivo, to modulate fertility, to modulate the aging process, and/or to modulate differentiation and cell growth (e.g., to treat diseases such as cancer). The present invention relates to the use of the prelamin A pre peptide and/or functional variants or analogs thereof for research purposes, such as to investigate the molecular and cellular basis of cell differentiation. The present invention also relates to new methods for drug delivery (e.g., the ability to cause cell fusion can be harnessed to deliver pharmaceuticals and other agents in cells and vesicles) and drug discovery, including, but not limited to, tissue-specific ex vivo toxicity testing, as well as the development of functional analogs of prelamin A pre peptide and other compounds that regulate cell differentiation and growth. The prelamin A pre peptide can also be used in methods to identify immediate and downstream genes and proteins that are involved in the regulation of cell differentiation processes via the prelamin A pre peptide pathway, and the discovery of such genes and proteins can be used to develop additional therapeutic, commercial and research tools and methods for use in a variety of applications related to cell differentiation and tissue repair. In addition, the present invention relates to the use of prelamin A pre peptide and/or variants or analogs thereof to tag, identify and isolate stem cells from different tissues. Moreover, the induction of stem cell differentiation by the peptide of the invention can be used to identify and isolate stem cells from different tissues.

According to the present invention, prelamin A is a preprotein expression product of the lamin A/C gene that is post-translationally processed to yield (1) lamin A and (2) the "pre" peptide, also referred to herein as the "prelamin A pre peptide", "pre", or "prelamin A peptide". The nucleotide sequence of the cDNA encoding human "prelamin" C (Database Accession No. NM_005572) is represented herein by SEQ ID NO:7. The cDNA nucleic acid sequence encoding human prelamin A (Database Accession No. NM_170707) is represented here by SEQ ID NO:3. SEQ ID NO:3 encodes the human prelamin A protein that has an amino acid sequence represented herein by SEQ ID NO:4. The nucleic acid and amino acid sequence of prelamin A is also known for a variety of other animal species, including, but not limited to: mouse, chicken, *Xenopus laevis* (African clawed frog), and *Danio rerio* (zebra fish). The nucleic acid sequence of mouse prelamin A (Database Accession No. BC015302) is represented herein by SEQ ID NO:8. SEQ ID NO:8 encodes the mouse prelamin A protein that has an amino acid sequence represented by SEQ ID NO:9. The nucleic acid sequence of chicken prelamin A (Database Accession No. X16879) is represented herein by SEQ ID NO:10. SEQ ID NO:10 encodes the chicken prelamin A protein that has an amino acid sequence represented by SEQ ID NO:11. The nucleic acid sequence of *Xenopus laevis* prelamin A (Database Accession No. X06345) is represented herein by SEQ ID NO:12. SEQ ID NO: 12 encodes the *Xenopus laevis* prelamin A protein that has an amino acid sequence represented by SEQ ID NO: 13. The nucleic acid sequence of *Danio rerio* prelamin A (Database Accession No. AF397016) is represented herein by SEQ ID NO:14. SEQ ID NO:14 encodes the *Danio rerio* prelamin A protein that has an amino acid sequence represented by SEQ ID NO: 15.

As discussed above, prelamin A processing proceeds through a sequential series of post-translational protein modifications (Sinensky et al., (1994), supra). The cysteine residue in the prelamin A C-terminal CAAX motif (C=Cysteine, A=aliphatic amino acid, X=any amino acid) (e.g., positions 661-664 of SEQ ID NO:4) is farnesylated, followed by the endoproteolytic removal of the C-terminal tripeptide (-AAX). The now C-terminal cysteine residue is carboxymethylated, and finally the C-terminal 15 amino acid peptide (in humans) (i.e., the "pre" peptide) containing the modified cysteine residue (e.g., positions 647-661 of SEQ ID NO:4) is removed by an additional endoproteolytic processing step. The nucleic acid sequence of human lamin A is represented herein by SEQ ID NO:5. SEQ ID NO:5 encodes the lamin A protein having the amino acid sequence represented by SEQ ID NO:6.

The nucleic acid sequence of the processed "pre" peptide from human prelamin A is represented herein by SEQ ID NO:1. SEQ ID NO:1 encodes a 15 amino acid prelamin A pre peptide having an amino acid sequence represented herein by SEQ ID NO:2. One of skill in the art will know, based on the sequence of the prelamin A proteins from other animal species and the knowledge of how the protein is processed, the sequence of the processed lamin A and "pre" peptides corresponding to these other prelamin A proteins. For example, the mouse pre peptide is, by homology to the human pre peptide: LLGNSSPRSQSSQNC (SEQ ID NO:16). The chicken pre peptide has been shown to be: VLGGAGPRRQAPAPQGC (SEQ ID NO:17). The pre peptide for *Xenopus laevis* is, by homology to the human pre peptide: IVGNGQRAQVAPQNC (SEQ ID NO: 18). The pre peptide for *Danio rerio* is, by homology to the human pre peptide: IVSNDKPRQAGPKVDNC (SEQ ID NO:19). The sequences of the lamin A and "pre" peptides for any known prelamin A protein or nucleic acid sequence encoding the same are explicitly encompassed by the present invention. The complete sequences represented by each of the sequence database accession numbers recited herein are incorporated herein by reference. An alignment of the prelamin A "pre" peptide amino acid sequences (including the entire CAAX motif that is ultimately processed to reveal a modified cysteine C terminus), is shown in FIG. 3.

Although the embodiments of the invention are discussed below with regard to the human prelamin A and prelamin A pre peptide sequences (e.g., SEQ ID NO:4 and SEQ ID NO:2, respectively), it is to be understood that the present invention expressly encompasses the substitution of sequences of prelamin A or prelamin A pre peptide from any other animal species (including from mouse, chicken, *Xenopus laevis* or *Danio rerio* discussed above), or any functional homologue or analog of prelamin A pre peptide, in any of the embodiments described below.

Various embodiments of the present invention relate to an isolated prelamin A pre peptide or a variant thereof, and the use of the peptide for regulation of cell differentiation. In one embodiment, the peptide is selected from: (a) a peptide consisting essentially of or consisting of SEQ ID NO:2; (b) a biologically active fragment consisting essentially of or consisting of SEQ ID NO:2; (c) a peptide consisting essentially of or consisting of an amino acid sequence that is at least about 70% identical to SEQ ID NO:2 with the biological activity of SEQ ID NO:2; and/or (d) a peptide consisting essentially of or consisting of an amino acid sequence that differs from SEQ ID NO:2 by at least one, two, three, four, five, six, seven, eight, nine, or ten substitutions, deletions or insertions of an amino acid residue at a position of SEQ ID NO:2 selected from the group consisting of: 1, 2, 5, 6, 9, 10, 11, 12, 13 and/or 14, wherein the peptide has the biological activity of SEQ ID NO:2. As discussed above, SEQ ID NO:2 represents the amino acid sequence of a prelamin A pre peptide. The peptide can, in some embodiments, be labeled, provided in a fusion protein or chimeric protein, or provided in a composition or formulation (described below). Biological activities of a prelamin A pre peptide are described in detail herein. In general, a preferred prelamin A pre peptide, including a variant thereof, is a peptide that induces differentiation of a cell.

Some embodiments of the present invention relate to an isolated peptide selected from: (a) a protein comprising, consisting essentially of, or consisting of an amino acid sequence represented by SEQ ID NO:4; (b) a protein comprising, consisting essentially of, or consisting of biologically active fragment of SEQ ID NO:4; and (c) a protein comprising, consisting essentially of, or consisting of an amino acid sequence that is at least about 70% identical to SEQ ID NO:4, wherein the protein has prelamin A or lamin A biological activity. In one aspect, this protein is chemically or recombinantly attached to a therapeutic agent that increases the half-life of the protein in cardiac or skeletal muscle tissue. SEQ ID NO:4 represents the amino acid sequence of a prelamin A protein of the invention.

The "pre" peptide of prelamin A is a small, 15 amino acid, naturally occurring, readily synthesized (e.g., chemically), signaling peptide that specifically promotes cell fusion, cell morphogenesis, cell differentiation, and cell organization in post-embryonic cells and even in embryonic stem cells. Consequently, this peptide is an excellent drug candidate as it will specifically promote the differentiation of any cell type and establishes cell morphology and tissue architecture in cells, as well as promotes cell fusion and regeneration of cells and tissues that have been damaged by disease or other factors. The peptide or a homologue thereof could be given in its protein form, or introduced as a cDNA by gene therapy. Alternatively, synthetic analogs having the activity of the prelamin A pre peptide can be identified or designed and produced, and used in the methods described herein. The prelamin A cDNA is also an excellent candidate for gene therapy of a variety of disorders involving the damage and/or degeneration of organs or tissues (or the protein encoded thereby could be delivered).

According to the present invention, an isolated protein or peptide, such as a prelamin A protein or pre peptide, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein such as a prelamin A protein of the present invention is produced recombinantly. An isolated peptide, such as the pre peptide, can be produced synthetically (e.g., chemically, such as by peptide synthesis) or recombinantly. In addition, and by way of example, a "human prelamin A pre peptide" refers to a prelamin A pre peptide (generally including a homologue of a naturally occurring prelamin A pre peptide) from a human (Homo sapiens), or to a prelamin A pre peptide that has been otherwise produced from the knowledge of the structure (e.g., sequence), and perhaps the function, of a naturally occurring prelamin A pre peptide from Homo sapiens. In other words, general reference to a human prelamin A pre peptide includes any prelamin A pre peptide that has substantially similar structure and function of a naturally occurring prelamin A protein from Homo sapiens or that is a biologically active (i.e., has biological activity) homologue of a naturally occurring prelamin A pre peptide from Homo sapiens as described in detail herein. As such, a human prelamin A pre peptide can include purified, partially purified, recombinant, mutated/modified and synthetic proteins. The same description applies to reference to other proteins or peptides described herein, such as prelamin A.

According to the present invention, the terms "modification" and "mutation" can be used interchangeably, particularly with regard to the modifications/mutations to the primary amino acid sequences of prelamin A or pre (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with a lipid carrier. Such modifications can be considered to be mutations if the modification is different than the post-translational modification that occurs in the natural, wild-type protein or peptide.

According to the present invention, the term "variant" can be used generally to describe protein (e.g., a homologue) and non-protein (e.g., a mimetic or analog) variants of a protein or peptide of the invention. As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. A homologue can include an agonist of a protein or peptide or an antagonist of a protein or peptide.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in protein homologues, as compared to the wild-type protein, either agonize, antagonize, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein.

According to the present invention, an isolated prelamin A protein or an isolated pre peptide (or other isolated protein described herein), including a biologically active homologue or fragment thereof, has at least one characteristic of biological activity of activity the wild-type, or naturally occurring protein (which can vary depending on whether the homologue or fragment is an agonist, antagonist, or mimic of the wild-type protein). The biological activity of prelamin A can include any activity of the pre peptide or of the lamin peptide, including, but not limited to: expression of prelamin A or pre peptide; processing of prelamin A to release the pre peptide and lamin; pre peptide signal transduction, synchronization of intercellular signaling with changes in lamin A localization and nuclear lamina morphology that occur early in myoblast differentiation, synchronization of transcriptional regulation of muscle-specific genes or cell cycle arrest that occurs concomitant with myoblast differentiation, induction of myoblast activation and differentiation, and incorporation of lamin A into the nuclear lamina structure.

Biological activity of prelamin A pre peptide more particularly includes the following activities: (1) induction of cell differentiation; (2) induction of directional cellular morphogenesis and cell polarity; (3) upregulation of intermediate filament expression and organization within the nuclear lamina; (4) induction of tissue-specific gene expression; and/or (5) induction and direction of intracellular and intercellular organization and tissue development. Biological activity of a prelamin A pre peptide can be described generally or with reference to a particular cell type. For example, biological activities of prelamin A pre peptide that are related to skeletal muscle cells include, but are not limited to: induction of cell cycle arrest; induction of skeletal muscle-specific gene expression; induction of cellular morphogenesis and fusion; induction of formation of myotubes; and induction of the formation of intracellular and extracellular matrices in differentiating muscle cells. Biological activities of prelamin A pre peptide that are related to cardiac cells include: induction of single cell, mononucleate and binucleate cardiac myocytes; induction of an interconnecting extracellular desmin matrix; induction of cardiac muscle-specific genes; and induction of formation of higher order intracellular and intercellular structures.

Methods of detecting and measuring prelamin A or prelamin A pre peptide biological activity (which can be applied appropriately to measure agonist or antagonist activity) include, but are not limited to, measurement of transcription of prelamin A; measurement of translation of prelamin A; measurement of posttranslational modification of prelamin A; measurement of processing of the prelamin A pre peptide; measurement of pre peptide signal transduction; measurement of binding of prelamin A pre peptide to a receptor on a cell; measurement of induction of cell differentiation; measurement of lamin A incorporation into the nuclear lamina structure; measurement of prelamin A incorporation into the cytoskeletal and extracellular matrix, measurement of transcriptional regulation of tissue-specific genes; measurement of cell cycle arrest; measurement of nuclear lamina morphology changes; measurement of pre peptide transport; measurement of lamin A localization; measurement of prelamin A localization, measurement of cell fusion; measurement of cell morphogenesis, measurement of cell activation; and/or measurement of formation of intercellular organization and tissue development. It is noted that an isolated protein of the present invention (including homologues) is not necessarily required to have the biological activity of the wild-type protein. For example, a prelamin A protein or a prelamin A pre peptide can be a truncated, mutated or inactive protein. Such proteins are useful in diagnostic assays or some screening assays, for example, or for other purposes such as antibody production. In a preferred embodiment, the isolated proteins of the present invention (e.g., prelamin A or pre peptide) have biological activity that is similar to that of the wild-type protein or peptide (although not necessarily equivalent to the wild-type protein or peptide) and in some embodiments, may have increased or decreased activity as compared to the wild-type protein or peptide.

Methods to measure protein expression levels of this invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to DNA binding, ligand binding, or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichrosim, or nuclear magnetic resonance (NMR). To evaluate whether two proteins interact, two hybrid assays (e.g., yeast two hybrid assays) are useful and are particularly useful for identifying proteins (gene products) that interact with prelamin A or pre peptide.

As used herein, an "agonist" of a protein or peptide of the invention refers to any compound that is characterized by the ability to agonize (e.g., stimulate, induce, increase, enhance, or mimic) the biological activity of the naturally occurring (wild-type) protein as described herein. More particularly, an agonist can include, but is not limited to, a protein, peptide, or nucleic acid that stimulates, induces, mimics or enhances the activity of the natural ligand, (e.g., prelamin A or pre peptide), and includes homologue of the wild-type protein, a binding protein (e.g., an antibody), or any suitable product of drug/compound/peptide design or selection which is characterized by its ability to agonize (e.g., stimulate, induce, increase, enhance) the biological activity of a naturally occurring protein. Agonists can be useful in methods for regulating cellular differentiation and growth activation and/or the repair or regeneration of tissues and/or organs, and in fertility applications.

The phrase, "antagonist" refers to any compound which inhibits (e.g., antagonizes, reduces, decreases, blocks, reverses, or alters) the effect of a naturally occurring or wild-type protein of the invention or of an agonist thereof, as described above. More particularly, an antagonist is capable of associating with proteins or other compounds in a manner similar to the wild-type protein, or otherwise acts in a manner relative to the activity of the wild-type protein, such that the biological activity of the wild-type protein is decreased or blocked in a manner that is antagonistic (e.g., against, a reversal of, contrary to) to the natural action of wild-type protein. Such antagonists can include, but are not limited to, a protein, peptide, or nucleic acid (including ribozymes, antisense, RNAi, or aptamers) or products of drug/compound/peptide design or selection that provides the antagonistic effect.

Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that is able to perform biological catalysis (e.g., by breaking or forming covalent bonds). More specifically, ribozymes are antisense RNA molecules that function by binding to the target RNA moiety and inactivate it by cleaving the phosphodiester backbone at a specific cutting site. An anti-sense nucleic acid molecule is defined as an isolated nucleic acid molecule that reduces expression of a protein by hybridizing under high stringency conditions to a gene encoding the protein (including to regulatory regions of the gene encoding the protein).

Homologues of prelamin A or the pre peptide, including peptide and non-peptide agonists and antagonists of prelamin A or the pre peptide, can be products of drug design or selection and can be produced using various methods known in the art. Such homologues can be referred to as mimetics or analogs of prelamin A or the pre peptide. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In one embodiment of the present invention, a prelamin A protein has an amino acid sequence that comprises, consists essentially of, or consists of, SEQ ID NO:4. SEQ ID NO:4 represents a human prelamin A protein (encoded by nucleic acid sequence SEQ ID NO:3). The present invention also includes homologues of SEQ ID NO:4, or fragments of SEQ ID NO:4, wherein the homologue or fragment has prelamin A biological activity (including agonist or antagonist activity), as described previously herein.

In one embodiment of the present invention, a prelamin A pre peptide has an amino acid sequence that comprises, consists essentially of, or consists of, SEQ ID NO:2, SEQ ID NO:16, SEQ ID NO:17, SEQ ID NO:18 or SEQ ID NO:19. SEQ ID NO:2 represents a human pre peptide (encoded by SEQ ID NO:1). SEQ ID NO:16 represents mouse pre peptide. SEQ ID NO: 17 represents chicken pre peptide. SEQ ID NO: 18 represents *Xenopus laevis* pre peptide. SEQ ID NO: 19 represents *Danio rerio* pre peptide. The present invention also includes homologues of SEQ ID NO:2, SEQ ID NO:16, SEQ ID NO: 17, SEQ ID NO:18 or SEQ ID NO:19 or fragments of SEQ ID NO:2, SEQ ID NO:16, SEQ ID NO:17, SEQ ID NO:18 or SEQ ID NO:19, wherein the homologue or fragment has pre peptide biological activity (including agonist or antagonist activity), as described previously herein and as described in more detail below.

In one embodiment, a pre peptide or a prelamin A protein of the present invention, including a homologue thereof, has an amino acid sequence that is at least about 50% identical to the wild-type sequence (e.g., an amino acid sequence of SEQ ID NO:2 or SEQ ID NO:4, or sequences from other species, including those described herein), respectively, over the full length of any of such sequences, wherein the protein has pre peptide or prelamin A biological activity (which can include agonist or antagonist activity), respectively. In another embodiment, a pre peptide or a prelamin A protein useful in the present invention has an amino acid sequence that is at least about 55% identical, or at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical to the wild-type or reference sequence (e.g., SEQ ID NO:2 or SEQ ID NO:4, or sequences from other species, including those described herein), respectively, over the full length of any of such sequences.

In one embodiment of the present invention, a homologue of a protein, such as a prelamin A protein or a prelamin A pre peptide according to the present invention has an amino acid sequence that is less than about 100% identical to the wild-type sequence (e.g., SEQ ID NO:4 or SEQ ID NO:2, or sequences from other species, including those described herein). In another aspect of the invention, a homologue according to the present invention has an amino acid sequence that is less than about 99% identical to the wild-type amino acid sequence, and in another embodiment, is less than is less than 98% identical to the wild-type amino acid sequence, and in another embodiment, is less than 97% identical to the wild-type amino acid sequence, and in another embodiment, is less than 96% identical to the wild-type amino acid sequence, and in another embodiment, is less than 95% identical to the wild-type amino acid sequence, and in another embodiment, is less than 94% identical to the wild-type amino acid sequence, and in another embodiment, is less than 93% identical to the wild-type amino acid sequence, and in another embodiment, is less than 92% identical to the wild-type amino acid sequence, and in another embodiment, is less than 91% identical to the wild-type amino acid sequence, and in another embodiment, is less than 90% identical to the wild-type amino acid sequence, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Sch ffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a pre peptide homologue or a prelamin A homologue includes a protein having an amino acid sequence that is sufficiently similar to a naturally occurring pre peptide or prelamin A amino acid sequence, respectively, that a nucleic acid sequence encoding the homologue is capable of hybridizing under moderate, high, or very high stringency conditions (described below) to (i.e., with) a nucleic acid molecule encoding the naturally occurring protein (i.e., to the complement of the nucleic acid strand encoding the naturally occurring amino acid sequence). Preferably, a protein useful in the invention, including a homologue, is encoded by a nucleic acid sequence that hybridizes under moderate, high or very high stringency conditions to the complement of a nucleic acid sequence that encodes a protein comprising an amino acid sequence represented by SEQ ID NO:2 or SEQ ID NO:4, or sequences from other species, including those described herein. Even more preferably, a protein useful in the present invention, including a homologue, is encoded by a nucleic acid sequence that hybridizes under moderate, high or very high stringency conditions to the complement of the coding region of a nucleic acid sequence selected from SEQ ID NO:1 or SEQ ID NO:3, or fragments thereof. Such hybridization conditions are described in detail below. A nucleic acid sequence complement of nucleic acid sequence encoding a protein useful in the present invention refers to the nucleic acid sequence of the nucleic acid strand that is complementary to the strand that encodes the protein. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence of pre peptide or prelamin A, for example, and/or with the complement of the nucleic acid sequence that encodes any of such amino acid sequences. Methods to deduce a complementary sequence are known to those skilled in the art. It should be noted that since amino acid sequencing and nucleic acid sequencing technologies are not entirely error-free, the sequences presented herein, at best, represent apparent sequences of pre peptide and prelamin A of the present invention. In addition, the sequences described herein are representative of the sequences that are useful in the present invention. However, it is to be understood that, in addition to other homologues described herein, sequences representing naturally occurring polymorphisms of the described sequences, or sequences using alternative codons (e.g., optimized or preferred or alternative) which encode the same amino acid sequence, are encompassed by the invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In another embodiment of the invention, a homologue of a prelamin A protein or a pre peptide can include at least one modification to a specific amino acid residue of the wild-type sequence, wherein the resulting homologue preferably retains a biological activity of the wild-type protein or peptide. Particularly preferred modifications include at least one, two, three, four, five, six, seven, eight, nine or ten substitutions, deletions, or insertions of an amino acid residue for an amino acid residue that does not, or is predicted not to, substantially affect the biological activity of the protein. Referring to FIG. 3, the present inventor has aligned the prelamin A pre peptide (including the ultimately cleaved –AAX motif from prelamin A, described above) to show the conserved amino acid positions relative to the human sequence. Based on such an alignment, one of skill in the art can readily predict which amino acid positions are most likely to tolerate substitution, modification, insertion or deletion, and whether substitutions or additions should be conservative or less conservative.

For example, from the alignment provided in FIG. 3, it is clear that the human sequence (positions 647-664 of SEQ ID NO:4; represented by SEQ ID NO:20) is most closely related to the mouse (positions 648-665 of SEQ ID NO:9; represented by SEQ ID NO:21) and chicken sequence (positions 638-657 of SEQ ID NO:11; represented by SEQ ID NO:22), and less so to frog (positions 648-665 of SEQ ID NO:13; represented by SEQ ID NO:23) and fish (positions 640-659 of SEQ ID NO:15; represented by SEQ ID NO:24), as would be expected based on taxonomy. With reference to the human sequence shown in FIG. 3, since the amino acid position of relative to human T9 (threonine at position 9 of SEQ ID NO:20) is not conserved in any species, the substitutions of serine (S), arginine (R) and glutamic acid (Q) for this amino acid sequence of other species are unlikely to have an effect and therefore, this position is likely to tolerate a variety of substitutions or other modifications. The substitutions seen in chicken, frog and fish for human S5, S6, Q10 and S11 are more intermediate in terms of the type of substitution at this position between species, and so one could make more conservative, but not necessarily very conservative, substitutions or modifications at these positions with a reasonable expectation of avoiding significantly altering protein activity or processing. The alignment indicates that modifications could also be made at positions relative to human L1 and L2. However, since the differences among species at these positions are very conservative (e.g., a valine or isoleucine for a leucine), one would preferably limit modifications at this position to the most conservative possibilities (e.g., one would typically avoid substitution of a polar or charged amino acid at these aliphatic positions, but favor substitutions of other aliphatic amino acids such as valine or isoleucine for the leucine residue). The positions relative to human G3, N4, P7, R8, P12, Q13, N14, C15, S16, I17 and M18 are conserved in 4 of the 5 species, or in all 5 species. Substitutions in these amino acids would be the most likely to affect protein activity and/or processing, although as discussed below, substitutions or modifications at these positions are not excluded in the present invention.

In general, one could use the following guidelines with reference to the human sequence (SEQ ID NO:20). L1 and L2 are conservatively substituted among other species and so good choices for substitution would be other aliphatic amino acids. G3 is only non-conservatively substituted in zebrafish, and would be an unlikely choice for substitutions that would not affect activity. N4 is only nonconservatively substituted in chicken and would be a weak choice. S5 is conservatively substituted in chicken, zebrafish and frog, and the S6 is non-conservatively substituted in these three species. Therefore, both serines (S5 and S6) would be intermediate sites for substitutions. P7 and R8 are only non-conservatively substituted in *Xenopus* and would be weak targets, while the following T9 is nonconservatively substituted in all 4 species, making it the strongest target for substitutions that are not predicted to affect activity. Q10 has nonconservative substitutions in zebrafish and frog, making it an intermediate candidate, while S11 is nonconservatively substituted in chick, fish and frog, making it an intermediate candidate as well. P12 has a conservative substitution to an S in mouse only, indicating this particular amino acid change may not affect activity, but other changes at this residue would be predicted to affect activity. Q13 has a conservative substitution in zebrafish only, making it a poor choice, and the following N14 has a nonconservative substitution in chicken only, indicating it is not a preferred position for substitutions. However, it is noted that the chicken prelamin A pre peptide is able to induce differentiation of cells from mammalian species (e.g., mouse), demonstrating the ability to modify substantial regions of the peptide while maintaining function of the peptide or to use any of the pre peptides described herein or derived from prelamin A or C in other species in any of the methods and compositions described herein. The final CSIM (positions 15-18 of SEQ ID NO:20 in FIG. 3, corresponding to positions 661-664 of SEQ ID NO:4) is the CAAX motif, and is conserved through all species, indicating it is not normally modified. However, because the –AAX motif is known to be degenerate regarding the ability to direct farnesylation, the present inventor envisions the possibility of making substitutions in these amino acids, particularly with regard to embodiments directed to modifying the farnesylation processing steps of prelamin A.

Finally, it is to be understood that while positions that contain the most variability across species are the most likely to be mutated without effect, any substitution which occurs between species may be conservative functionally. Therefore, even though there are only single substitutions in each of the P12, Q13 and N14 amino acids at the end of the human sequence (SEQ ID NO:20), one might want to introduce these single amino acid substitutions in the human sequence because they have low probabilities of affecting activity.

Preferred amino acid residues of the human prelamin A pre peptide sequence for modification include, but are not limited to: 1, 2, 5, 6, 9, 10, 11, 12, 13 and/or 14, with modifications at positions 1, 2, 5, 6, 9, 10, 11 and/or 12 being more preferred, and modifications at positions 1, 2, 5, 6, 9, 10 and/or 11 being particularly preferred.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol*. (1982) 157: 105-132), or on the basis of the ability to assume similar polypeptide secondary structure (Chou and Fasman, *Adv. Enzymol*. (1978) 47: 45-148, 1978).

The minimum size of a protein and/or homologue of the present invention is, in one aspect, a size sufficient to have the requisite biological activity, including agonist or antagonist activity, or sufficient to serve as an antigen for the generation of an antibody or as a target or detectable reagent in an in vitro assay. In one embodiment, a pre peptide of the present invention is at least about 8 amino acids in length, or at least about 9 amino acids in length, or at least about 10 amino acids in length, or at least about 11 amino acids in length, or at least about 12 amino acids in length, or at least about 13 amino acids in length, or at least about 14 amino acids in length, or at least about 15 amino acids in length. There is no limit, other than a practical limit, on the maximum size of such a protein in that the protein can include a portion of a pre peptide or a full-length pre peptide, plus additional sequence (e.g., a fusion protein sequence), if desired.

In one embodiment, a prelamin A protein of the present invention is at least about 8 amino acids in length (e.g., suitable for an antibody epitope or as a detectable reagent in an assay), or at least about 25 amino acids in length, or at least about 50 amino acids in length, or at least about 100 amino acids in length, or at least about 150 amino acids in length, or at least about 200 amino acids in length, or at least about 250 amino acids in length, or at least about 300 amino acids in length, or at least about 350 amino acids in length, or at least about 400 amino acids in length, or at least about 450 amino acids in length, or at least about 500 amino acids in length, or at least about 550 amino acids in length, or at least about 600 amino acids in length. Again, there is no limit, other than a practical limit, on the maximum size of such a protein in that the protein can include a portion of a prelamin A protein or a full-length prelamin A protein, plus additional sequence (e.g., a fusion protein sequence), if desired.

The present invention also includes a fusion protein that includes a prelamin A pre peptide- or a prelamin A-containing segment (i.e., an amino acid sequence for a prelamin A pre peptide or a prelamin A protein according to the present invention, including homologues and fragments thereof) attached to one or more fusion segments. Suitable fusion segments for use with the present invention include, but are not limited to, segments that can: enhance a protein's stability or half-life; provide a means to identify the protein; provide another desirable biological activity (e.g., a therapeutic protein/peptide to be delivered to a site); and/or assist with the purification of the protein (e.g., by affinity chromatography). A suitable fusion segment can be a domain of any size that has the desired function (e.g., imparts increased stability, solubility, biological activity; and/or simplifies purification of a protein). Fusion segments can be joined to amino and/or carboxyl termini of the pre peptide- or prelamin A-containing segment of the protein and can be susceptible to cleavage in order to enable straight-forward recovery of the desired protein. Fusion proteins are preferably produced by culturing a recombinant cell transfected with a fusion nucleic acid molecule that encodes a protein including the fusion segment attached to either the carboxyl and/or amino terminal end of a pre peptide- or prelamin A-containing segment. Fusion proteins can also be expressed from vectors encoding them in vivo or in situ. Discussion of expression of nucleic acid molecules in vivo is provided below.

In one embodiment of the present invention, any of the amino acid sequences described herein can be produced with from at least one, and up to about 20, additional heterologous amino acids flanking each of the C- and/or N-terminal ends of the specified amino acid sequence (the specified amino acid sequence being, for example, SEQ ID NO:2, SEQ ID NO:4, a biologically active fragment thereof or a biologically active homologue thereof). The resulting protein or polypeptide can be referred to as "consisting essentially of" the specified amino acid sequence. According to the present invention, the heterologous amino acids are a sequence of amino acids that are not naturally found (i.e., not found in nature, in vivo)

flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts an additional function to the protein or changes the function of the protein having the specified amino acid sequence.

Another embodiment of the present invention relates to a composition comprising at least about 500 µg, and preferably at least about 1 µg, and more preferably at least about 5 µg, and more preferably at least about 10 µg, and more preferably at least about 25 µg, and more preferably at least about 50 µg, and more preferably at least about 75 µg, and more preferably at least about 100 µg, and more preferably at least about 250 µg, and more preferably at least about 500 µg, and more preferably at least about 750 µg, and more preferably at least about 1 mg, and more preferably at least about 5 mg, of an isolated pre peptide or a prelamin A protein comprising any of the proteins, fragments thereof or homologues thereof discussed herein (including, for example, a fragment having the prelamin A inter-nuclear transport domain biological activity). Such a composition of the present invention can include any carrier with which the protein is associated by virtue of the protein preparation method, a protein purification method, or a preparation of the protein for use in an in vitro, ex vivo, or in vivo method according to the present invention. For example, such a carrier can include any suitable excipient, buffer and/or delivery vehicle, such as a pharmaceutically acceptable carrier (discussed below), which is suitable for combining with the protein so that the protein can be used in vitro, ex vivo or in vivo according to the present invention. Compositions of the invention, including therapeutic compositions, are discussed in detail below.

Further embodiments of the present invention include nucleic acid molecules that encode any of the above-identified proteins, including a homologue or fragment thereof. In one embodiment, a nucleic acid molecule encoding pre peptide includes the nucleic acid sequence represented by SEQ ID NO: 1, fragments thereof, or nucleic acid molecules encoding homologues of SEQ ID NO:2, SEQ ID NO:16, SEQ ID NO: 17, SEQ ID NO:18 or SEQ ID NO: 19 as described herein. Nucleic acid molecules encoding prelamin A include the nucleic acid sequence represented by SEQ ID NO:3, fragments thereof, or nucleic acid molecules encoding homologues of SEQ ID NO:4 as described herein. In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene or a portion of a gene (e.g., the regulatory region or promoter). An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

Isolated nucleic acid molecules include natural nucleic acid molecules and homologues thereof, including, but not limited to modified (mutated) nucleic acid molecules in which, as compared to the natural or wild-type sequence, nucleotides have been inserted, deleted, substituted, and/or inverted in such a manner that such modifications (mutations) result in a nucleic acid sequence that encodes a desired homologue of a protein as described herein. A nucleic acid molecule homologue (e.g., a nucleic acid molecule encoding a protein homologue of the present invention) can be produced using a number of methods known to those skilled in the art (see, for example, Sambrook et al., *Molecular Cloning: A Laboratory Manual*, Cold Spring Harbor Labs Press, 1989). For example, wild-type nucleic acid molecules can be modified or nucleic acid molecules encoding modified proteins can be created using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids, for example, by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions, discussed in detail above) with the complementary sequence of a nucleic acid molecule useful in the present invention, or of a size sufficient to encode an amino acid sequence for a protein of the invention. The nucleic acid molecule may also include regulatory regions, linker sequences, vector sequence or other sequence as necessary to provide a nucleic acid molecule according to the present invention. The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. An oligonucleotide preferably ranges from about 5 to about 50 or about 500 nucleotides, including any size between about 5 and about 500 in whole integers (i.e., 5, 6, 7, 8, 9, . . . 34, 35, 36, . . . 200, 201, 202, . . . 500), and more preferably from about 10 to about 40 nucleotides, and most preferably from about 15 to about 40 nucleotides in length. There is no limit, other than a practical limit, on the maximal size of a nucleic acid molecule of the present invention, in that the nucleic acid molecule can include a sequence sufficient to encode the proteins of the invention and since the size of the nucleic acid molecule encoding such proteins can be dependent on nucleic acid composition and whether regulatory regions and/or other sequence are included (e.g., linkers, vector sequence, etc.).

Particularly preferred nucleic acid molecules according to the present invention include nucleic acid molecules comprising, consisting essentially of, or consisting of, nucleic acid sequences encoding any of the above-described amino acid sequences, including homologues thereof. In one embodiment, such a nucleic acid sequence includes an a nucleic acid sequence that is at least about 55% identical, or at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical to SEQ ID NO:1 or SEQ ID NO:3, or to any of the other nucleic acid sequences described herein or encoding any of the amino acid sequences described herein, over the full length of any of such sequences. Particularly preferred nucleic acid sequences include, but are not limited to, SEQ ID NO: 1, SEQ ID NO:3, or fragments of such sequences, including a nucleic acid sequence encoding an isolated fragment of SEQ ID NO:4 with inter-nuclear transport domain biological activity or a biologically active homologue thereof. Additionally, fragments and other homologues of such sequences corresponding to the encoded amino acid sequences described above are also included. In one embodiment, the nucleic acid molecule does not encode a protein with biological activity, but is an oligonucleotide probe or primer (described previously herein).

One embodiment of the present invention relates to a recombinant nucleic acid molecule which comprises any of the isolated nucleic acid molecules described above which is operatively linked to at least one transcription control sequence. More particularly, according to the present invention, a recombinant nucleic acid molecule typically comprises a recombinant vector and an isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a prelamin A pre peptide) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence (e.g., a transcription control sequence and/or a translation control sequence) in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Preferred promoters to use in a recombinant nucleic acid molecule according to the invention include any promoter which can function in cell-type in which the recombinant nucleic acid molecule is expressed. For example, for use in cardiac or skeletal muscle tissue, such promoters include, but are not limited to, a cardiac-specific promoter, a muscle-specific promoter, and a prelamin A promoter. In one aspect, the promoter is a myosin heavy chain promoter.

Recombinant nucleic acid molecules of the present invention can also contain additional expression control and other regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into a membrane of a host cell. Suitable leader sequences include a leader sequence that is naturally associated with the protein, or any heterologous leader sequence capable of directing the delivery and insertion of the protein to a membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells, and is used herein to generally encompass transfection of animal cells and transformation of microbial cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

One or more recombinant molecules of the present invention can be used to produce an encoded product (e.g., a prelamin A protein or a prelamin A pre peptide) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole (e.g., for ex vivo administration), either of which can be used in a composition. In some instances, the protein may be expressed in a host cell in vivo (e.g., via gene therapy). A preferred cell to culture is any suitable host cell as described above. Effective in vitro or ex vivo culture conditions include, but are not limited to, effective media, bioreactor, temperature, pH and oxygen conditions that permit protein production and/or recombination. An effective medium refers to any medium in which a given host cell is typically cultured. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins produced according to the present invention are preferably retrieved in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is typically substantially free of contaminants, other proteins and/or chemicals that might interfere or that would interfere with its use in a method disclosed by the present invention, or that at least would be undesirable for inclusion with the protein (including homologues) when it is used in a method disclosed by the present invention. assays, preparation of therapeutic compositions, administration in a therapeutic composition, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., a prelamin A protein is about 80% of the total protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

In one embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The isolated nucleic acid molecules of the present invention, as well as the proteins produced by such molecules are all useful in various compositions of the invention. For example, in one embodiment, the isolated nucleic acid molecule (preferably as part of a recombinant nucleic acid molecule) is useful as for gene therapy, wherein administration of the nucleic acid molecule to an animal results in transfection of host cells of the animal with the molecule and expression of the protein(s) expressed by the molecule. As discussed above, nucleic acids encoding the prelamin A pre peptide or prelamin A are excellent candidates for gene therapy of a variety of disorders related to degeneration of tissue or failure of tissue or organs to grow and develop. For example, the present inventor has shown that prelamin A is rapidly transferred between the multiple nuclei within a myocyte, and affects the morphology and organization of the transfected myocytes as well as that of adjacent untransfected myocytes. In another embodiment, the isolated nucleic acid molecule is used to produce the encoded protein(s) in vitro, which can then be used in a therapeutic composition. In yet another embodiment, the isolated nucleic acid molecule can be used to transfect cells ex vivo and then the cells are returned to the patient from which they were removed.

In one embodiment of the present invention, a therapeutic composition (comprising a nucleic acid or a protein) comprises a pharmaceutically acceptable carrier, which includes pharmaceutically acceptable excipients and/or delivery vehicles, for delivering the recombinant nucleic acid molecule or the proteins to a patient. As used herein, a pharmaceutically acceptable carrier refers to any substance or vehicle suitable for delivering a therapeutic composition useful in a therapeutic method of the present invention (described below) to a suitable in vivo or ex vivo site. When a nucleic acid molecule is in the composition, preferred pharmaceutically acceptable carriers are capable of maintaining the nucleic acid molecule in a form that, upon arrival of the nucleic acid molecule to a target cell or tissue, the nucleic acid molecule is capable of entering the cell and being expressed by the cell, whereby the expressed protein can perform one or more biological activities of the protein as described previously herein. When the composition comprises a protein, preferred pharmaceutically acceptable carriers are capable of maintaining the protein composition in a form that, upon arrival of the protein composition to a target cell or tissue, the proteins are capable of performing one or more biological functions of the protein as discussed above at the cell or tissue site.

A pharmaceutically acceptable carrier can include a pharmaceutically acceptable excipient. Suitable excipients of the present invention include excipients or formularies useful in a therapeutic composition. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable pharmaceutically acceptable carriers for nucleic acids include, but are not limited to liposomes or other lipid-containing vehicles, viral vectors, ribozymes, gold particles, poly-L-lysine/DNA-molecular conjugates, and artificial chromosomes. Natural lipid-containing delivery vehicles include cells and cellular membranes. Artificial lipid-containing delivery vehicles include liposomes and micelles. A delivery vehicle can be modified to target to a particular site in a patient, thereby targeting and making use of a nucleic acid molecule at that site. Suitable modifications include manipulating the chemical formula of the lipid portion of the delivery vehicle and/or introducing into the vehicle a targeting agent (e.g., an antibody or peptide) capable of specifically targeting a delivery vehicle to a preferred site, for example, a preferred cell type. It is noted, however, that the prelamin A pre peptide can induce differentiation of any cell in a cell-type specific manner and therefore, appropriate administration of the prelamin A pre peptide (e.g., appropriate route and dosage) inherently will "target" the appropriate tissue and cell types. Therefore, the present invention can be particularly advantageous in that while targeting moieties can be used, they are likely not necessary to administer these proteins or peptides (or nucleic acids encoding them) in vivo. However, depending on the mode of administration, it may be desired to limit access of the prelamin A pre peptide to a specified cell or tissue and in this instance, targeting moieties, or in vitro or ex vivo delivery may be employed.

A liposome delivery vehicle comprises a lipid composition that is capable of delivering a nucleic acid molecule of the present invention, including naked DNA, plasmids and viral vectors, to a suitable cell and/or tissue in a patient. A liposome delivery vehicle comprises a lipid composition that is capable of fusing with the plasma membrane of the target cell to deliver the recombinant nucleic acid molecule into a cell. As discussed above, liposome delivery vehicles can be modified to target a particular site in a patient (i.e., a targeting liposome), thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms include targeting a site by addition of exogenous targeting molecules (i.e., targeting agents) to a liposome (e.g., antibodies, soluble receptors or ligands). Targeting liposomes are described, for example, in Ho et al., 1986, *Biochemisty* 25: 5500-6; Ho et al., 1987a, *J Biol Chem* 262: 13979-84; Ho et al., 1987b, *J Biol Chem* 262: 13973-8; and U.S. Pat. No. 4,957,735 to Huang et al., each of which is incorporated herein by reference in its entirety).

Suitable pharmaceutically acceptable carriers for protein compositions include, but are not limited to, liquid injectables or solids which can be taken up in a suitable liquid as a suspension or solution for injection, liquids that can be aerosolized, capsules, tablets, or liposomes. In a non-liquid formulation, the excipient can comprise, for example, dextrose, human serum albumin, and/or preservatives to which sterile water or saline can be added prior to administration.

One type of pharmaceutically acceptable carrier includes a controlled release formulation that is capable of slowly releasing a composition of the present invention into an animal. As used herein, a controlled release formulation comprises recombinant nucleic acid molecule or protein composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems.

Proteins and variants thereof, nucleic acids and compositions of the invention are useful in a variety of methods, including assays for the identification of compounds (including genes and proteins), as well as a variety of therapeutic methods, commercial methods and research methods. The present invention includes methods which use prelamin A pre peptide, homologues and fragments thereof, analogs thereof, nucleic acids encoding the peptide, and/or isolated cells that express the peptide, as therapeutic reagents, research tools, screening tools and/or diagnostic tools.

Accordingly, embodiments of the present invention relate to: (1) a method to induce differentiation of a cell; (2) a method to generate a tissue or organ in vitro or ex vivo; (3) a method to induce regeneration or repair of a damaged or degenerated tissue or organ; (4) a method to stimulate tissue or organ growth; (5) a method to treat a disorder associated with tissue or organ damage or degeneration; (6) a method to protect a subject from a condition or disorder associated with lamin A/C mutations, whether or not such a condition or disorder is actually caused by the lamin A/C mutation; (7) a method to promote fertility in a mammal; (8) a method to promote the fertilization of a gamete; (8) a method to slow the aging process in a mammal; (9) a method to treat cancer; (10) a method to reduce or reverse non-disease related muscle atrophy; (11) a method to repair or enhance the repair of bone fractures; and (12) a method to improve joint physiology. Each of these methods includes the step of contacting a cell, tissue or organ, by in vitro, ex vivo, or in vivo administration, with a prelamin A pre peptide or a functional homologue or analog thereof (also possibly an antagonist, as stopping prelamin A processing may also be beneficial, possibly in cancers, etc.). The peptide (or homologue or analog) can be provided alone, in a composition or formulation, linked to another compound, or when a protein, as a nucleic acid molecule encoding the peptide, or as a fusion protein, tagged protein, a chimeric protein, or in conjunction with an agonist.

In addition to being useful for tissue and organ engineering, to repair or regenerate injured tissue, to reduce the effects of aging, to enhance athletic performance, and in fertility applications, the methods of the present invention can be used to treat a number of diseases and conditions in which manipulation of cell differentiation and particularly, induction or enhancement of tissue and organ growth and repair, or alternatively enhanced cell fusion and apoptosis, could be beneficial. The methods of the current invention can also be used to treat any disease or condition resulting from or associated with mutations in the lamin A/C gene or genes encoding lamin A/C processing enzymes, or those which affect lamin A/C expression, whether or not said condition is caused by lamin A/C mutations in the case to be treated. Such diseases include, but are not limited to, Hutchinson Gilford Progeria Syndrome, Dilated Cardiomyopathy, Emery-Dreifuss Muscular Dystrophy, Limb Girdle Muscular Dystrophy, Mandiboluacryl Dysplasia, Partial Lipodystrophy, Charcot-Marie Tooth Disease, Lipoatrophy with Diabetes, Hepatic Steatosis, Hypertrophic Cardiomyopathy, and Leukomelanodermic Papules, and Restrictive Dermopathy. Since lamin A/C mutations may result in diseases with overlapping pathologies, the methods of the current invention can also be used to treat any disease or condition in which there is any combination of pathologies or symptoms associated with lamin A/C disease mutations or mutations affecting prelamin A expression and/or processing, such as those arising from mutations in Zmpste24. The methods of the invention can also be used to treat any disease or condition in which the same or similar pathologies and/or symptoms of diseases and conditions resulting from lamin A/C mutations, or mutations which affect prelamin A processing and/or expression, occur alone or in conjunction with any pathologies or conditions not associated with lamin A/C disease mutations or those effecting its processing and/or expression, or in which the disease pathologies or conditions affect the same tissue but in a different way, in a different subgroup, and/or in a different region of the tissue. In these embodiments, the method is applicable whether or not such diseases and conditions are due to genetic or other factors, or a combination thereof. Such diseases and conditions include, but are not limited to, Dilated Cardiomyopathy, Conduction System Defects, Arrhythmogenic Right Ventricular Dysplasia, Hypertrophic Cardiomyopathy, Atrial Standstill, Congestive Cardiomyopathy, Coronary Artery Disease, and any other disease or condition effecting cardiac cells, tissue or the heart as an organ. Such diseases also include, but are not limited to, Fukuyama Congenital Muscular Dystrophy, Duchenne Muscular Dystrophy, Rigid Spine Muscular Dystrophy, Spinal Muscular Atrophy, and any other muscular dystrophy, myopathy, muscle disorder or condition affecting skeletal muscle tissue and/or cells and/or connective tissue. Such diseases also include, but are not limited to, Cockayne Syndrome, alopecia, atherosclerosis, lipodystrophy, joint disorders and dysfunction, skin abnormalities, or any disease or condition associated with aging and/or progeria, or affecting skin, nerve, heart, skeletal muscle, smooth muscle, liver, kidney, pancreas, hair follicles, connective tissue, bone, adipose, blood vessels or any other cell, tissue or organ that is affected or that fails to grow normally in Hutchinson Gilford Progeria Syndrome. Such disorders and conditions also include but are not limited to lipodystrophy, diabetes, aberrant adipocyte development, aberrant adipocyte localization, or aberrant fat distribution, or any disease or condition affecting a cell, tissue or organ that is affected in lipodystrophy or diabetes. Such disorders and conditions also include but are not limited to sclerosis, contractures, defective wound healing, skeletal abnormalities, tooth, hair and skin abnormalities, lipodystrophy, insulin resistance, or any disease or condition affecting a cell, tissue or organ that is effected in Mandibuloacryl Dysplasia.

The methods of the current invention can also be used to treat any downstream disease or condition arising from a disease or condition associated with, or having overlapping pathologies and/or characteristics to those observed in any disease caused by mutations in the lamin A/C gene, or mutations affecting prelamin A expression and/or processing, such as those arising from mutations in the gene encoding Zmpste24.

The methods of the current invention can also be used to treat any disease or condition in which the induction of cellular differentiation, the cessation of cellular proliferation, the induction of cell- and/or tissue-specific proteins, and/or the induction of cell and/or tissue morphogenesis could be beneficial. Such diseases and conditions include, but are not limited to, Leukemia, Sarcoma, Lymphoma, Mesothelioma, Lung Cancer, Myeloma, Carcinoma, Teratoma, or any malignant or benign primary or downstream (i.e. secondary, tertiary, etc.) metastatic or non-metastatic cancer or precancerous disease, tumor, tissue, cell, area, growth, lesion or condition.

In the method of inducing differentiation in a cell, the cell is contacted with a prelamin a pre peptide, or a functional homologue or analog thereof, such that differentiation of a cell is induced. The contact can occur in vitro, ex vivo or in vivo. The conditions under which the cell is contacted in vitro or ex vivo can include any suitable culture conditions for the cell type, but need not necessarily include the conditions of cell confluence or a particular media or combination of differentiation or growth factors. Indeed, the present inventor has demonstrated that prelamin A pre peptide can induce differentiation of stem cells under conditions whereby cell differentiation would not normally proceed or is inhibited (e.g., in the absence of cell confluence or differentiation factors). Preferably, the cell is a stem cell, including embryonic stem cells and adult stem cells, although the invention also includes embodiments wherein the cell is any differentiated or non-differentiated cell, or a cancer cell. Suitable stem cells include, but are not limited to, a mesodermal stem cell, an endodermal stem cell, or an ectodermal stem cell, and can more particularly include, but is not limited to, a neural stem cell, a hematopoietic stem cell, a mesenchymal stem cell, an epithelial stem cell, an intestinal stem cell, a skin stem cell, an osteoblast stem cell, a preadipocyte, a pancreatic stem cell, a liver stem cell, a lung stem cell, a cardiac muscle stem cell, a skeletal muscle stem cell. Combination of stem cells can also be contacted using the method of the invention. The cells can be provided as isolated cells, populations of cells, or cells that are already associated in a tissue or organ. Additional suitable cells include any differentiating or differentiated cell, including, but not limited to, differentiating or differentiated cells derived from any of the stem cell types described above (e.g., a differentiated or differentiating neural cell).

In the methods of generating a tissue or organ ex vivo or in vitro, of inducing regeneration or repair of a damaged or degenerated tissue or organ, or stimulating tissue or organ growth, of treating a disorder associated with tissue or organ damage or degeneration, of protecting a subject from a disorder associated with lamin A/C mutations or affected by lamin A/C polymorphisms, of promoting fertility in a mammal or promoting fertility of a gamete, of slowing the aging process, or of treating cancer, the appropriate cell, tissue or organ is contacted with a prelamin A pre peptide of the invention, or a functional homologue or analog thereof, which can include contacting the cell, tissue or organ in vitro or ex vivo or by administering the compound by an in vivo method. In the case of tissue or organ generation, repair or regeneration or treating a disease, the cells that are preferably contacted are stem cells in or from or which can differentiate into the cell type, tissue or organ of interest. In fertility methods, the gamete is preferably contacted with the compound, most preferably concurrent with or immediately following fertilization. In a subject with cancer, the cell to be contacted is the tumor cell.

As discussed above, many of the above-described methods include the use of stem cells. Reference to "stem cells", as used herein, refers to the term as it is generally understood in the art. For example, stem cells, regardless of their source, are cells that are capable of dividing and renewing themselves for long periods, are at least to a degree unspecialized (undifferentiated), and can give rise to (differentiate into) specialized cell types (i.e., they are progenitor or precursor cells for a variety of different, specialized cell types). "Long-term", when used in connection with stem cells, refers to the ability of stem cells to renew themselves by dividing into the same non-specialized cell type over long periods (e.g., many months to years) depending on the specific type of stem cell. The phenotypic characteristics of various long-term stem cells from different animal species are known in the art. Adult stem cells include stem cells that can be obtained from any non-embryonic tissue or source, and typically generate the cell types of the tissue in which they reside. The term "adult stem cell" may be used interchangeably with the term "somatic stem cell".

Stem cells used in the present invention can include any adult stem cells or embryonic stem cells obtained from any source. Adult stem cells useful in the present invention include, but are not limited to, hematopoietic stem cells, mesenchymal stem cells (including, but not limited to, lung mesenchymal stem cells, bone marrow stromal cells), neural stem cells, epithelial stem cells (from any tissue type, such as lung, breast, vascular system, intestine), intestinal stem cells, cardiac myocyte progenitor stem cells, skin stem cells (including, but not limited to, epidermal stem cells and follicular stem cells (hair follicle stem cells)), skeletal muscle stem cells, osteoblastic precursor stem cells, preadipocytes, pancreatic stem cells and liver stem cells. Hematopoietic stem cells give rise to all of the types of blood cells, including but not limited to, red blood cells (erythrocytes), B lymphocytes, T lymphocytes, natural killer cells, neutrophils, basophils, eosinophils, monocytes, macrophages, and platelets. Mesenchymal stem cells (including bone marrow stromal cells) give rise to a variety of cell types, including, but not limited to bone cells (osteocytes), cartilage cells (chondrocytes), fat cells (adipocytes), lung cells, and other kinds of connective tissue cells such as those in tendons. Neural stem cells in the brain give rise to its three major cell types: nerve cells (neurons) and two categories of non-neuronal cells, astrocytes and oligodendrocytes. Epithelial stem cells in the lining of various tissues give rise to several cell types that form the epithelium in tissues. Skin stem cells occur in the basal layer of the epidermis and at the base of hair follicles. The epidermal stem cells give rise to keratinocytes, which migrate to the surface of the skin and form a protective layer, and the follicular stem cells can give rise to both the hair follicle and to the epidermis. Other sources of adult stem cells will be known to those of skill in the art.

Methods for obtaining such stem cells and providing initial culture conditions, such as a liquid culture or semi-solid culture medium, are known in the art. The cells are initially expanded in vivo or in vitro, by contacting the source of the stem cells with a suitable reagent that expands or enriches such cells in the tissue source or in culture. Preferably, adult stem cells are isolated from a tissue source and then expanded or enriched in vitro by exposure to a suitable agent. Cells are obtained from an individual by any suitable method for obtaining a cell sample from an animal, including, but not limited, to, collection of bone marrow collection of a bodily fluid (e.g., blood), collection of umbilical cord blood, tissue punch, and tissue dissection, including particularly, but not limited to, any biopsies of skin, intestine, cornea, spinal cord, brain tissue, scalp, stomach, breast, lung (e.g., including lavage and bronchioschopy), fine needle aspirates of the bone marrow, amniotic fluid, placenta and yolk sac.

Unique features of the prelamin A "pre" peptide described in detail herein are that it is a naturally occurring, small, biologically active signaling peptide. It would be easy to synthesize using a variety of systems, including in a host cell, and particularly, in yeast, since yeast contain all of the necessary processing enzymes. In addition, the peptide will induce the appropriate differentiation or repair program in the cell, tissue or microoenvironment in which it is placed, and it would have no toxicity. Also, in the case of use of the invention for the treatment of cancer, the peptide will induce the differentiation of the treated cell, aberrant or otherwise, and/or the death of the treated cell (and tumors comprising the cell), such that these cells would no longer be metastatic and/or invasive.

According to the present invention, the phrase "protected from a disease" refers to reducing the symptoms of the disease; reducing the occurrence of the disease, and/or reducing the severity of the disease. Protecting a patient can refer to the ability of a therapeutic composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease or that is experiencing initial symptoms or later stage symptoms of a disease (therapeutic treatment). In particular, protecting a patient from a disorder as described herein can be accomplished according to the present invention by increasing: cell differentiation, cell fusion, intercellular organization, prelamin A processing, prelamin A pre peptide signal transduction, and/or proper lamina formation. Protecting a patient from a cancer is accomplished by: increasing cell fusion and death, for example, or by causing a tumor cell to differentiate, which is believed to be able to cause the tumor cell to stop growing and dividing. The term, "disease" refers to any deviation from the normal health of a patient and includes a state when disease symptoms are present, as well as conditions in which a deviation (e.g., infection, gene mutation, genetic defect, etc.) has occurred, but symptoms are not yet manifested.

According to the present invention, an effective administration protocol (i.e., administering a therapeutic composition in an effective manner) comprises suitable dose parameters and modes of administration that result in the desired result associated with the prelamin A pre peptide as described above. Preferably, a cell is induced to differentiate, a tissue or organ is repaired, regenerated, or created, or a patient or subject is protected from a disease (e.g., by disease prevention or by alleviating one or more symptoms of ongoing disease) or gains a different beneficial effect from the administration of a compound or composition of the invention (e.g., enhanced fertility, reduced impact of aging). Effective dose parameters can be determined using methods standard in the art for a particular disease or condition. In some circumstances, the patient may not have disease, but rather tissue atrophy, a bone fracture, some cell or tissue damage, or perhaps no disease or condition at all (e.g., an athlete or other healthy but perhaps aging individual who would benefit from regeneration or repair of tissues and/or organs that have damage or reduced function due to aging). Effective dose parameters can be determined by those of skill in the art depending on the desired effect (e.g., stimulation of growth of healthy tissue, repair or regeneration of damaged tissue, etc.). Such parameters include, for example, determination of survival rates, side effects (i.e., toxicity), progression or regression of disease, or progress in tissue growth. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that results in regulation of the prelamin A pre peptide signal transduction pathway and associated biological activities, when used or administered one or more times over a suitable time period. Doses can vary depending upon the disease being treated. For example, in the treatment of cancer, a suitable single dose can be dependent upon whether the cancer being treated is a primary tumor or a metastatic form of cancer. One of skill in the art can readily determine appropriate single dose sizes for a given patient based on the size of a patient and the route of administration. In the case of in vitro or ex vivo applications, the present inventor has discovered that the prelamin A pre peptide is effective at very small doses (e.g., in the micromolar and nanomolar range), and that the effect of the peptide on cell cycle arrest, morphogenesis and cell fusion is dose dependent.

One of skill in the art can monitor the effectiveness of a treatment to repair damaged tissue or organs by measuring, for example, cell morphology, physiological indicators of healthy tissue, physiological indicators of damaged tissue, and include standard physiological tests for various tissues and organs. For example, in the case of cardiac or skeletal muscle tissue, such tests include, but are not limited to, EKG, echocardiography, catheterization, heart biopsy, MRI, motion and strength tests, measurement of muscle isoforms of creatine kinase in serum, and muscle biopsies.

In one aspect of the invention, a suitable single dose of a compound or composition of the present invention is an amount that, when administered to a cell, tissue, organ, or individual by any type of administration, increases or induces at least one aspect of the prelamin A pre peptide signaling pathway of cell differentiation (e.g., cell fusion, cell morphological changes, gene expression, cell cycle arrest, inter- and intracellular organization and morphology), as compared to a cell, tissue, organ or individual which has not been contacted with the compound or composition of the present invention, as compared to the cell, tissue, organ or individual prior to contact with the compound or composition, or as compared to a known or predetermined standard for the cell, tissue, organ or individual.

It will be obvious to one of skill in the art that the number of doses or administrations needed is dependent upon the particular method and the result desired, and in the case of a patient, the response of an individual patient to the treatment. Thus, it is within the scope of the present invention that a suitable number of doses or administrations of a compound or composition includes any number required to treat a given disease or to achieve a desired effect.

As discussed above, a compound or composition of the present invention is administered to a patient in a manner effective to deliver the compound or composition to a cell, a tissue, an organ, and/or to an individual, whereby regulation of the prelamin A pre peptide signaling pathway of cell differentiation and downstream biological activities is achieved as a result of the administration of the compound or composition. Suitable administration protocols include any in vitro, in vivo or ex vivo administration protocol. The preferred types and routes of administration will be apparent to those of skill in the art, depending on the type of condition to be prevented or treated; whether the composition is nucleic acid based, protein based, or cell based; and/or the target cell/tissue.

For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Combinations of routes of delivery can be used and in some instances, may enhance the therapeutic effects of the composition.

Ex vivo administration refers to performing part of the regulatory step outside of the patient, such as administering a composition (nucleic acid or protein) of the present invention to a population of cells (e.g., stem cells) removed from a patient under conditions such that the composition contacts and/or enters the cell, and returning the cells to the patient. Ex vivo methods are particularly suitable when the target cell can easily be removed from and returned to the patient.

Cells, tissues or organs can be contacted ex vivo or in vitro with a compound of the invention by any suitable method, including mixing, the use of a delivery vehicle, or a method of introducing the compound into the cell. Effective in vitro or ex vivo culture conditions include, but are not limited to, effective media, bioreactor, temperature, pH and oxygen conditions that permit protein production and/or recombination. An effective medium refers to any medium in which a given host cell or tissue is typically cultured. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a cell or tissue. Such culturing conditions are within the expertise of one of ordinary skill in the art.

Many of the above-described routes of in vivo administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety.

For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo.

Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811: 299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270: 470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a $\beta$2-adrenergic receptor, administered by intracoronary delivery, resulted in diffuse multichamber myocardial expression of the gene in vivo, and subsequent significant increases in hemodynamic function and other improved physiological parameters. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a bicistronic recombinant molecule. Naked nucleic acid delivery can include intramuscular, subcutaneous, intradermal, transdermal, intranasal and oral routes of administration, with direct injection into the target tissue (e.g., skeletal muscle or cardiac muscle) being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to treat using a composition of the invention include humans, dogs, cats, mice, rats, sheep, cattle, horses and pigs, with humans being most preferred. In one embodiment, the invention is used to differentiate stem cells from various livestock/food animals into tissue (e.g., muscle) to provide consumable protein sources (e.g., meat).

The discovery by the present inventor has also led the inventor to propose using this information to provide enhanced methods of tagging, identifying and/or isolating stem cells, and methods to identify compounds that regulate cell differentiation, through a variety of different assays. Such methods are useful for identifying therapeutic reagents for treating various disorders and diseases and/or for promoting cell, tissue or organ growth and repair; for identifying reagents useful for promoting tissue and organ engineering (i.e., in vitro); for identifying reagents useful in fertility research and treatment; and for identifying additional research and therapeutic targets (e.g., downstream molecules) for further applications in cell differentiation, disease, aging, fertility and cancer prevention.

One method of the present invention relates to a method to identify a method to tag or identify stem cells from a tissue. The method includes the step of: (a) contacting a tissue with a labeled prelamin A pre peptide; and (b) identifying cells that incorporate the labeled prelamin A pre peptide. In one aspect, the method further includes a step of isolating the stem cells identified in (b). Useful labels can include fluorescent dyes (e.g., fluorescein, texas red, rhodamine, Alexa fluors, Spectrum dyes, and the like), quantum dots, radiolabels (e.g., $^3$H, $^{125}$I, $^{35}$S, C, or $^{32}$P), and colorimetric labels.

Another embodiment of the present invention relates to a method to identify and isolate stem cells from a tissue, comprising: (a) contacting a tissue with a prelamin A pre peptide or a functional homologue or analog thereof; (b) identifying cell types that differentiate when contacted with the peptide or functional homologue or analog thereof; and (c) isolating the type of cells identified in (b) from an undifferentiated cell population or tissue.

Another embodiment of the invention relates to a method to identify compounds that regulate prelamin A pre peptide-induced cell differentiation, comprising: (a) contacting stem cells with prelamin A pre peptide or functional homologue or analog thereof in the presence and absence of a putative regulatory compound, wherein in the absence of the putative regulatory compound, the stem cells will differentiate when contacted with the prelamin A pre peptide or functional homologue or analog thereof; and (b) detecting a change in the differentiation of the stem cells in the presence of the putative regulatory compound as compared to in the absence of the putative regulatory compound, wherein detection of a change in the differentiation of the stem cells indicates that the compounds regulate prelamin A pre peptide-induced cell differentiation.

Another embodiment of the invention relates to a method to identify compounds that regulate cell differentiation, comprising: (a) contacting an isolated prelamin A processing-deficient cell with a test compound for regulation of cell activation and differentiation; and (b) detecting whether the test compound regulates an activity in the cell selected from the group consisting of: prelamin A processing, prelamin A pre peptide transport, and cell differentiation, as compared to in the absence of the test compound.

In one aspect, the test compound is selected from the group consisting of: a homologue of prelamin A pre peptide with putative prelamin A pre peptide biological activity; a pharmaceutical compound with putative prelamin A pre peptide biological activity; a homologue of prelamin A with putative prelamin A biological activity; a candidate protein for a prelamin A processing enzyme, or a gene encoding the candidate protein; a candidate protein for a downstream prelamin A pre peptide signal transduction protein, or a gene encoding the candidate protein; and a putative pharmaceutical compound for use in the treatment of a disorder.

In one embodiment, the step of detecting in the methods above comprises detecting binding between prelamin A pre peptide and the test compound. Such an assay need not be a cell based assay (e.g., immunoprecipitation assay), although cells can be particularly useful for this type of assay (e.g. a yeast two hybrid system).

The test compound can include a variety of different types of compounds. In one aspect, the test compound is a protein encoded by a gene that is a candidate for regulation of prelamin A pre peptide signal transduction in the cell. In another aspect, the test compound is a pharmaceutical compound. In yet another aspect, the test compound is a homologue of a prelamin A pre peptide or downstream signal transduction molecule, or a gene encoding any of these test compounds.

Cells useful in the present assay include any cell that can be induced to differentiate (or de-differentiate) or undergo a change related to the differentiation process. Stem cells, including adult and embryonic stem cells, are particularly useful in the methods of the invention, and have been described in detail above. The cells can include cells isolated from an individual to be treated.

With respect to the prelamin A processing deficient cells, the present inventor has identified disease mutations that inhibit proper prelamin A processing in myocyte cell lines. This protein, and these transfected cell lines, will permit the elucidation of the enzymes and steps in the prelamin A processing pathway by complementation experiments. These cell lines will also serve as a reagent to test therapeutic agents to rectify the prelamin A processing deficiencies. Cell lines generated from a patient identified as carrying this or other lamin A/C mutations can be used for similar purposes.

Having generally described various methods of identification of the invention, more particular details of the assays that apply to one or more of the methods above will now be described. For example, it will be apparent that the methods described above are typically cell-based assays, but may include cell-free assays, such as when one wishes to assess binding of one protein to another.

In one aspect of these methods, the methods can include a step of contacting a cell with a putative regulatory compound (a test compound, including a gene, protein or candidate drug), either prior to, concurrent with, or after contact of the cell with prelamin A pre peptide, followed by a step of detecting an effect on the cell, preferably as compared to in the absence of the putative regulatory compound.

In these embodiments, a change in the regulation of some aspect of cell differentiation or the prelamin A processing pathway, including downstream events that result from activation of this pathway, in the presence of the test compound as compared to in the absence of the test compound indicates that the test compound is an regulator of cell differentiation or the prelamin A processing pathway. If the initial assay is not a cell-based assay (e.g., detects only binding of the test compound to a protein such as prelamin A), then the compound can be further tested, if desired, in a cell-based assay to determine whether the compound inhibits or enhances a biological activity as described herein. Such further steps will help detect the mode of action of the compound and whether it might be an agonist or antagonist of the cell differentiation and/or prelamin A pre peptide signaling.

As used herein, the term "putative" or "test" or "candidate" refers to compounds having an unknown or previously unappreciated regulatory activity in a particular process. As such, the term "identify" is intended to include all compounds, the usefulness of which as a regulatory compound according to the invention determined by a method of the present invention.

The methods of the present invention include contacting test compounds and cells, proteins or genes with one another to detect binding of one component to another or to detect the effect of the contact on expression and/or biological activity of one or more of the components. The step of contacting can be performed by any suitable method, depending on how the test compound and the cell, proteins, or genes are provided. For example, cells can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micro-nutrients. Cell lysates can be combined with other cell lysates and/or the compound to be tested in any suitable medium. In another embodiment, proteins and/or cell lysates containing such proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form. The putative regulatory compound can be contacted with the immobilized protein by any suitable method, such as by flowing a liquid containing the compound over the immobilized protein.

The present methods involve contacting cells or proteins with the compound being tested for a sufficient time to allow for interaction with the cell or protein, and regulation of the cell by the compound. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which the proteins are in contact with the compound being tested and/or the time period during which the proteins or cells and the test compounds are in contact (or in a condition where contact is possible) with each other. The term "incubation period" refers to the entire time during which, for example, cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. It will be recognized that shorter incubation times are preferable because compounds can be more rapidly screened.

The conditions under which a cell or cell lysate is contacted with a putative regulatory compound, such as by mixing, are any suitable culture or assay conditions and includes an effective medium in which the cell can be cultured or in which the cell lysate can be evaluated in the presence and absence of a putative regulatory compound. Similarly, the conditions under which proteins (e.g., prelamin A or pre peptide) are contacted with a putative regulatory compound or cells are any suitable assay conditions, such as by immobilization of the protein or peptide on a substrate or by mixing of the protein or peptide with the compound and/or cells, in conditions under which the protein or peptide can contact the putative regulatory compound or cells.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Acceptable protocols to contact a cell with a putative regulatory compound in an effective manner include the number of cells per container contacted, the concentration of putative regulatory compound(s) administered to a cell, the incubation time of the putative regulatory compound with the cell, and the concentration of compound administered to a cell. Determination of such protocols can be accomplished by those skilled in the art based on variables such as the size of the container, the volume of liquid in the container, the type of cell being tested and the chemical composition of the putative regulatory compound (i.e., size, charge etc.) being tested. A preferred amount of putative regulatory compound(s) comprises between about 1 nM to about 10 mM of putative regulatory compound(s) per well of a 96-well plate.

As discussed above, the step of detecting whether a test compound regulates any aspect of prelamin a pre peptide signal transduction and/or cell differentiation and/or its downstream biological effects, can be performed by any suitable method. Such methods include, but are not limited to: measurement of protein-protein binding or interaction, measurement of transcription of prelamin A; measurement of translation of prelamin A; measurement of posttranslational modification of prelamin A; measurement of processing of the prelamin A pre peptide; direct measurement of the prelamin A protein or peptide expression and localization; measurement of pre peptide signal transduction; measurement of binding of prelamin A pre peptide to a receptor on a cell; measurement of induction of cell differentiation; measurement of lamin A incorporation into the nuclear lamina structure; measurement of prelamin incorporation into the cytoskeleton or extracellular matrix; measurement of transcriptional regulation of tissue-specific genes; measurement of cell cycle arrest; measurement of nuclear lamina morphology changes; measurement of pre peptide transport; measurement of lamin A localization; measurement of cell fusion; measurement of cell activation; and/or measurement of formation of intercellular organization and tissue development. Techniques for performing such measurements are known in the art, and include a variety of binding assays, western blotting, immunocytochemistry, flow cytometry, other immunological based assays, phosphorylation assays, kinase assays, immunofluorescence microscopy, RNA assays, immunoprecipitation, cytokine assays, evaluation of cell morphology, in situ hybridization, and other biological assays. Binding assays include BIAcore machine assays, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Binding and/or interaction between two proteins can be determined using yeast two hybrid systems. Methods for evaluating prelamin A processing, prelamin A pre peptide signal transduction, and its biological effects are described in the Examples section.

As discussed above, in vitro cell based assays may be designed to screen for compounds that regulate prelamin A processing and associated biological events at either the transcriptional or translational level. For example, one embodiment of the invention relates to a method to identify a genes or gene products that are regulated by prelamin A pre peptide signaling. In one aspect, a nucleic acid sequence encoding a reporter molecule can be linked to a regulatory element of prelamin A or an associated protein and used in appropriate intact cells, cell extracts or lysates to identify compounds that modulate prelamin A gene expression or expression of a gene involved in prelamin A processing or pre peptide signal transduction. Appropriate cells or cell extracts can be prepared, if desired, from any cell type. The screen can be used to identify compounds that modulate the expression of the reporter construct. In such screens, the level of reporter gene expression is determined in the presence of the test compound and compared to the level of expression in the absence of the test compound.

In a related method to identify genes that are expressed during cell differentiation, the method comprises: (a) contacting stem cells with prelamin A pre peptide or functional homologue or analog thereof; and (b) identifying genes that are differentially regulated in the stem cells after contact with the peptide or functional homologue or analog thereof as compared to in the absence of contact with the peptide or functional homologue or analog thereof.

The method includes the step of detecting the expression of at least one, and preferably more than one, of the downstream genes that are expressed during prelamin A pre peptide induced cell differentiation. As used herein, the term "expression", when used in connection with detecting the expression of a downstream gene of the present invention, can refer to detecting transcription of the gene and/or to detecting translation of the gene. To detect expression of a gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene). Expression of transcripts and/or proteins is measured by any of a variety of known methods in the art. For RNA expression, methods include but are not limited to: extraction of cellular mRNA and chip analysis of downstream changes in mRNA expression, northern blotting using labeled probes that hybridize to transcripts encoding all or part of one or more of the genes of this invention; amplification of mRNA expressed from one or more genes using gene-specific primers, if available and reverse transcriptase—polymerase chain reaction, followed by quantitative detection of the product by any of a variety of means; extraction of total RNA from the cells, which is then labeled and used to probe cDNAs or oligonucleotides encoding all or part of the genes of this invention, arrayed on any of a variety of surfaces. For detecting changes in protein expression, a variety of techniques are known, including, but not limited to, Western blotting and 2-D mass spectrophotometry. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Another embodiment of the methods described above includes identifying whether a candidate gene is a gene that encodes a product that is involved in prelamin A pre peptide induced cell differentiation. Such methods are typically performed by protein-protein interaction assays to identify gene products that interact with a given protein (e.g., prelamin A or pre peptide), or by complementation assays using cell lines expressing various proteins in the pathway.

Yet another embodiment of the present invention relates to the use of prelamin A itself, or a fragment thereof with internuclear and intercellular transport activity, or a nucleic acid molecule encoding prelamin A of the fragment thereof, to deliver a compound to a cell, and to cells in the microenvironment of the cell to which the compound is delivered (e.g. in the same tissue, neighboring or adjoining cells, or the extracellular spaces between cells). Such a prelamin A protein can be delivered in protein form, or for example, encoded by a viral vector. Preferably, the prelamin A is linked to (e.g., as a fusion protein or by other forms of linkage, such as chemical linkage, if delivered as a protein) to a compound, such as a therapeutic compound or a labeling compound. Accordingly, a prelamin A protein useful in this aspect of the invention can include: (a) a protein comprising an amino acid sequence represented by SEQ ID NO:4; (b) a protein comprising biologically active fragment of SEQ ID NO:4 as discussed above; and (c) a protein comprising an amino acid sequence that is at least about 70% identical to SEQ ID NO:4, wherein the protein has prelamin A or lamin A biological activity. As discussed above, the protein can be chemically or recombinantly attached to a compound (agent) that is a therapeutic agent, a labeling agent, or increases the half-life of the protein in tissues. Accordingly, in one aspect, the prelamin A acts as a "carrier", which refers to any substance or vehicle suitable for delivering a therapeutic composition useful in a therapeutic method to a suitable in vivo or ex vivo site. Methods of conjugating or operatively linking the above-described protein or fragment to another protein or to a non-protein compound are well known in the art.

In one aspect, the prelamin A fusion protein or conjugated protein, or nucleic acid molecule encoding the same, is administered to a cell, and preferably a stem cell, ex vivo. The cell can then be activated using prelamin A pre peptide according to the invention, and the cell can be implanted or administered to an individual at a particular site, in order to provide a way to specifically deliver a compound to a site or tissue. More particularly, based on the present inventor's discovery of the ability of the movement of prelamin a between cells after stimulation/activation with prelamin a pre peptide, this method will provide an elegant and highly site or cell-specific method to deliver a compound to a tissue. Alternatively, the cell can be activated with prelamin A pre peptide once it has been implanted or delivered to the individual. In one embodiment, this method is particularly useful for delivery of compounds to muscle cells, although the method is not limited to these cells.

Yet another embodiment of the present invention relates to the use of prelamin A itself, or a biologically active fragment thereof, or a nucleic acid molecule encoding prelamin A of the fragment thereof, to induce or enhance differentiation of a stem cell. In this embodiment, the prelamin A or nucleic acid molecule encoding prelamin A is administered or delivered to a cell, tissue, or organism before, after, or at the same time as a prelamin A pre peptide as described herein. Without being bound by theory, the present inventor believes that prelamin A is involved in the signaling processes leading to cell differentiation and has shown that prelamin A is directly involved in forming the cytoskeleton and extracellular matrix and establishing cell morphology and tissue architecture, and therefore will be an important adjunct or alternative to the use of prelamin A pre peptide as described herein.

Yet another embodiment of the present invention relates to the use of Zmpste24, biologically active homologues and fragments thereof, and analogs thereof, to regulate differentiation in a cell. Zmpste24 is a zinc metalloproteases that cleaves (processes) prelamin A. Zmpste24 has retained the evolutionary ability to process prelamin A and can also process yeast a-factor, further demonstrating the homology between the yeast a-type mating pheromone system and the prelamin A pre peptide processing of the present invention. Zmpste24 is upregulated by prelamin A expression. Therefore, given the data provided herein with respect to prelamin a pre peptide and prelamin A, the present inventor proposes a method to identify homologues or agonists of Zmpste24 that can be used in additional methods of regulation of cell differentiation as described herein. As proliferative stages in stem cell differentiation, such as myoblasts, contain unprocessed prelamin A pools, the processing of these pools by Zmpste24, or a protease or other agent designed to cleave the prelamin A peptide is likely to initiate the signaling cascade in these stem cells, and possibly other stem cell types, leading to cellular differentiation. Consequently, Zmpste24 and other prelamin A processing agents can also be used to regulate cellular differentiation, tissue growth, and organ repair.

Another embodiment of the present invention relates to the use of genes that are upregulated in response to prelamin A pre peptide and prelamin A signaling (e.g., desmin, myogenin) as biomarkers for stem cell differentiation and activation. For example, such genes can be used as endpoint markers in methods for identification of homologues and analogs of prelamin A pre peptide or prelamin A function, or for the identification of other regulators of stem cell differentiation.

Each publication or other reference cited herein is incorporated by reference herein in its entirety.

The following examples are provided for the purpose of illustration and are not intended to limit the scope of the present invention.

EXAMPLES

Example 1

This example shows that the farnesylated carboxymethylated prelamin A pre peptide is the signal for skeletal muscle cell and cardiac muscle cell differentiation, growth and repair.

Materials and Methods

Cells and transfections. C2C12 and H9C2 cells were cultured in Growth Media (GM) defined as DMEM containing 10% (vol/vol) fetal bovine serum supplemented with Lglutamine, HEPES, non-essential amino acids and antibiotics. Effectene (Qiagen) was used to transfect plasmid DNA into cells following the manufacturer's instructions. Nondifferentiating transfected cells were allowed to continue growing for an additional 24 h before being processed for microscopy, or until confluent for protein isolation.

Peptide synthesis. The farnesylated and carboxymethylated prelamin A C-terminal peptide N-LLGNS-SPRTQSPQNC-C (SEQ ID NO:2) was generated by FMOC solid phase peptide synthesis, and farnesylated and carboxymethylated (Biosynthesis). The peptide was analyzed on a C4 column and by laser desorption mass spectrometry. The lyophilized peptide was resuspended in DMSO.

Microscopy. Cells were fixed in cold 70% methanol/30% acetone solution for 10 min. Immunostaining was performed with anti-human lamin A/C (Novocastra), anti-prelamin A (Santa Cruz), or anti-desmin (Sigma) primary antibodies followed by the appropriate fluorescently labeled secondary antibody and mounting in anti-fade media containing DAPI (Vector Laboratories). Images were captured on an Olympus IX81 inverted microscope with Olympus objectives (U PLAN APO 10× oil N.A. 0.40, UAPO 40× oil N.A. 1.35, TIRFM PLAN APO 60× oil N.A. 1.45 WD 0.15 mm) and a Hamamatsu ORCA IIER monochromatic CCD camera and Intelligent Imaging Slidebook software. Images were also acquired on an Olympus IX70 Infinity inverted microscope with Olympus objectives (100× U PLAN APO, N.A. 1.35, W.D. 0.1 mm, oil; 20× U PLAN Fluorite, N.A. 0.5) with a Photometrics Quantix cooled CCD camera using Deltavision software. Signal strengths for the individual channels were adjusted using Adobe Photoshop strictly for improving the overall signal to noise ratio.

Western blots. Cells were lysed in cell buffer (1% Triton X-100, 20 mM Tris-Cl, 7.5, 10 mM NaCl, 5 mM MgC2) containing 46 μg/ml leupeptin, 10 μg/ml aprotinin, and 250 μg/ml AE-BSF for 10 min on ice. Total protein concentration was determined using BioRad Protein Assay reagent and equal amounts of total protein were loaded in each lane. Western blots were probed with anti-lamin A/C (Novocastra, Santa Cruz), antiprelamin A (Santa Cruz) and anti-myogenin (Santa Cruz) primary antibodies and HRP-conjugated secondary antibodies (Santa Cruz, Pierce). Secondary antibody detection was performed using Super signal HRP (Pierce).

Results and Discussion

The farnesylated and carboxymethylated prelamin A pre peptide was chemically synthesized, and mitotically dividing C2C12 myoblasts were treated with the peptide at 1, 10 and 25 μg/ml in complete growth media containing 10% FBS. Six hours after peptide treatment at 1 μg/ml, cells have undergone morphogenesis into a bipolar configuration (FIG. 4B). The muscle-specific cytoskeletal IF protein desmin can be seen localizing to the interface with the nuclear lamina and forming a filamentous skeleton at the locations where cells interact. In some areas, cell fusion can be seen after just 6 hours of peptide treatment. At 72 hours, depending on cell density, the cells have fused to form either sheets or myotubes (FIGS. 4C and 4D). The non-directional nature in which the cells fuse indicates that, like a-factor, under normal conditions the peptide induces linear myotube formation by creating a signal gradient. The peptide also induces the kidney-shaped polarization of nuclei, with desmin aggregating at the central area. The peptide can also be seen to have a dose-dependant effect on cell proliferation.

To prove the peptide is a true myoblast differentiation signal and that it does not stimulate a general cellular fusion process, H9c2 rat cardiac myoblasts were treated with the peptide. These cells were previously considered to be of cardiac lineage in part because they express heart-specific L-type calcium channels after prolonged exposure to retinoic acid during serum starvation induced differentiation (24). However, differentiation of H9c2 cells in culture has previously led to fusion and multinucleate myotube formation more resembling skeletal myotubes than cardiac myocytes.

However, when exposed to the prelamin A pre peptide in growth media containing 10% FBS, H9c2 cells secrete an extensive desmin extracellular matrix (ECM) within just six hours (FIG. 5B). After 48 hours, the treated cardiac myoblasts have formed a tissue sheet of mono- and binucleated cells interconnected by an extensive ECM (FIG. 5C). Higher order intra- and intercellular organization is clearly evident in visible striations in the desmin staining pattern. Peptide-treated H9c2 cells show modest increases in lamin A/C and prelamin A expression (FIGS. 5D and 5E) consistent with results indicating that the processing of preexisting prelamin A and lamin A pools is necessary for myoblast differentiation (25). As in serum starvation induced differentiation of H9c2 myoblasts (26), an increase in the myogenic transcription factor myogenin is seen upon peptide treatment (FIG. 5F). As the promoter region of cardiac actin contains a functional myogenin binding site which appears to be active in a subset of cardiac and vascular smooth muscle cells (27), and as postnatal inhibition of myogenin expression does not effect skeletal muscle but results in a 30% decrease in animal size (28), these results indicate that myogenin may play a role in the differentiation of non-skeletal muscle stem cell types.

As intermediate filament proteins form polymers, the excretion of desmin into the ECM by H9c2 cells treated with the prelamin A pre peptide demonstrates that peptide treatment will refortify the ECM and consequently strengthen intercellular interactions and organization. The ability of the prelamin A peptide to induce ECM secretion demonstrates that peptide treatment will not only slow and, to a large degree, stop the aging process, but that it is also likely to reverse the physical and cosmetic effects of aging by directly rejuvenating tissue and organ architecture.

Immunostaining of prelamin A in peptide-treated C2C12 myoblasts indicates that prelamin A is involved in organizing chromatin, and forms a cytoskeleton and extracellular matrix during myoblast differentiation (FIG. 6). Internuclear connections containing prelamin A and desmin can be seen forming (FIGS. 6B, 6E and 6H) that are the likely route by which the GFP-prelamin A fusion proteins (FIG. 8) and other proteins are transferred between nuclear domains during myotube formation (29). The intranuclear prelamin A signal disappears as the nucleus becomes encapsulated in cytoplasmic prelamin A and desmin (FIGS. 6C, 6F, and 6I), indicating that prelamin A processing is responsible for protein redistribution (17, 18). Other DNA organizing proteins appear to maintain the chromatin organization once the prelamin A is released. Prelamin A and desmin envelope the differentiating nuclei and form a distinct cytoskeleton concomitant with the disappearance of the intranuclear prelamin A signal. This is also seen in the masking of the DAPI signal (FIG. 6L). An extensive system of vertical prelamin A and desmin "pillars" is seen at the periphery of the nucleus (FIGS. 6C, 6F, and 6I).

The round nucleus in the cell labeled A in FIG. 7B is not polarized, and intranuclear prelamin A is still present. The nucleus labeled B has become polarized, and the intranuclear prelamin A pools are mostly gone. However, prelamin A and desmin localization to the lamina interface is minimal as reflected by the strong DAPI signal. Prelamin A processing appears timed to coincide with cell polarization and the formation of a prelamin A-desmin cytoskeleton and extracellular matrix. In the cell labeled C, the chromatin domains have been organized into parallel rows. Prelamin A and desmin filaments can be seen to be forming at the nuclear periphery and running parallel to the cell bodies towards the direction of the cell mass. The extracellular prelamin A and desmin matrices are growing towards the mass of cells which are polarized and appear to have released the prelamin A peptide, and not those which are round and still contain intranuclear prelamin A. The cells labeled D have no intranuclear prelamin A, and have extensive prelamin A and desmin cyto- and exoskeletons forming. The cytoskeleton can be seen to be seeding at the nuclear lamina, and causing significant masking of the DAPI signal.

A distinct filamentous prelamin A cytoskeleton formed at the nuclear interface (FIGS. 6A, 6D and 6G) in all treated cells. Prelamin A also formed filamentous intercellular connections as well as intra- and internuclear matrices in all fusing cells which were not seen in any of the mock-treated DMSO controls (FIG. 7). Desmin colocalizes with the intra- and extracellular prelamin A matrices, indicating that the desmin architecture hybridizes to and is determined by the prelamin A cytoskeleton and extracellular matrix (FIGS. 6 and 7). These results demonstrate that prelamin A function extends beyond nuclear organization during cellular differentiation.

Referring again to FIG. 8, this figure shows nuclear disorganization, aberrant myotube morphology and intercellular disorganization. More particularly, mouse C2C12 skeletal myoblasts were transfected with wild type (WT) and mutant GFP-prelamin A fusion protein constructs indicated, and differentiated for two days by serum starvation. Bright field microscopy (A-G), direct fluorescence microscopy (H-N), and indirect immunofluorescence microscopy with an anti-desmin antibody (Sigma) (O-U) demonstrate aberrant cell morphology and nuclear organization as well as intercellular disorganization resulting from mutant prelamin A expression. The Arg89Leu mutation continues to result in aggregate formation while the effect of the Asn195Lys mutation on lamin aggregation has less penetrance in differentiating myotubes.

Together, these results demonstrate that the covalently modified C-terminal prelamin A peptide signals cardiac and skeletal myoblast differentiation. Without being bound by theory, the inventor believes that the covalently modified prelamin A C-terminal peptide functions by activating myoblasts and establishing a gradient that determines lamin architecture. The lamin architecture establishes the intracellular IF cytoskeleton, which determines cell morphology, and the extracellular IF matrix, which determines tissue organization and architecture. Lamin A/C mutations which interfere with particular lamin structures would only be predicted to affect the tissue, or tissue sub-group in which those structures are needed for proper tissue architecture, which explains why different lamin A/C mutations affect different tissues and tissue groups. The mutant, partially processed prelamin A protein would be predicted to interfere with cytoskeletal organization at the nuclear interface, explaining why farnesyl-transferase inhibitors show efficacy in a mouse HGPS disease model (9). The reason mice lacking prelamin A appear relatively normal (30) is because these mice are not true knockouts, and other endogenous lamin A/C splice variants seen in prelamin A peptide-specific Western blots of the C2C12 mouse (FIG. 9) and H9c2 rat cell lines (FIG. 5E) are likely still expressed in these animals. Concomitant expression of lamin A/C and tissue-specific IFs at the time of cellular differentiation (14) indicates that the lamin architecture seeds the IF cytoskeleton and is responsible for cell morphology in other differentiating cell types. Furthermore, the present inventor's findings, when viewed with studies showing that inhibition of prelamin A processing leads to a dose-dependant inhibition of tissue growth and repair in MADA (5), HGPS (6) and RD (7), provide compelling evidence that prelamin A peptide function is evolutionarily conserved in the differentiation of other stem cell types. In addition, it has been reported that a cleavage site mutation that prevents prelamin A processing accumulates in the somatic tissues of normal individuals as they age (12). The present inventor's results indicate that reintroduction of the prelamin A peptide can stop and reverse significant aspects of the normal human aging process caused by inhibition of prelamin A processing.

Example 2

The following example shows that cell morphology and tissue architecture in non-muscle cell types are determined by lamin architecture through the intermediate filament protein cytoskeleton.

While desmin is a muscle-specific intermediate filament protein, the concomitant expression of prelamin A and tissue-specific cytoskeleton-forming intermediate filament proteins at the time of cellular differentiation in nearly all cell types indicates that other intermediate filament family members play an analogous role to desmin in hybridizing to and replicating the nuclear lamina architecture in the cytoskeleton and extracellular matrix of non-muscle cell types. Direct evidence for this model is presented in FIGS. 10A-10D in which mouse F9 teratocarcinoma cells are transfected with the GFP-prelamin A fusion protein containing the Arg60Gly mutation and the Arg89Leu prelamin A processing mutation. In these cells, the intermediate filament cytoskeleton which forms upon cellular differentiation includes keratin 8, as opposed to the desmin in muscle cells. In the Arg60Gly transfected cells, the keratin 8 filaments were observed to be hybridizing to the prelamin A filaments in the nuclear lamina, producing a signal indicative of complete keratin 8-lamin A co-localization at the nuclear periphery (FIG. 10B). Furthermore, analysis of the keratin 8 localization demonstrated that the filamentous organization extends to the cell cytoskeleton and extracellular matrix (FIG. 10B, arrow).

The expression of the Arg89Leu processing defective prelamin A mutant, which can't release the peptide, results in the inhibition of the normal keratin cytoskeleton and the formation of aberrant keratin aggregates at polar locations at the nuclear periphery (FIG. 10D, arrows), which are similar in appearance to the desmin aggregates seen when myoblasts are exposed to the peptide. Furthermore, disruption of the nuclear lamina structure is communicated to adjacent cells not expressing the mutant lamin protein, demonstrating that lamin architecture not only determines cytoskeletal organization and cell morphology, but also intercellular organization and tissue architecture. These results directly demonstrate that lamin A architecture determines the intermediate filament cytoskeletal and intercellular organization in non-muscle cell types.

When the images of the F9 transfectants were re-examined after the peptide had caused C2C12 fusion, it became apparent that the expression of the different wild type and mutant GFP-prelamin A constructs had resulted in cellular morphogenesis and interaction. Expression of GFP-prelamin A containing the Asn195Lys mutation results in fusion of cells expressing the mutant GFP construct, as well as the untransfected cells around them (FIG. 10E-G). The DNA can be seen to be streaming out of untransfected cells that are fusing. Furthermore, expression of GFP-prelamin A has induced nuclear polarity, with many of the F9 nuclei taking on the identical kidney shaped appearance seen in peptide treated C2C12 myoblasts. The keratin staining pattern in the differentiating cells reproduces the pentagonal desmin-prelamin architecture (FIG. 10H, arrows), demonstrating that the same processes described in the image are taking place with prelamin A and lamin A, but with the intermediate filament keratin 8 replacing desmin, during the differentiation of a non-muscle cell type. Cells can also be seen to be interacting in areas where cells are expressing the GFP-lamin A protein, indicating that prelamin A expression is inducing intercellular organization. These results directly demonstrate that cell morphology and tissue architecture in non-muscle cell types are determined by the nuclear lamina architecture through the intermediate filament protein cytoskeleton.

Example 3

The following example shows that the prelamin A pre peptide not only induces fusion and morphogenesis of skeletal muscle satellite cells and F9 teratocarcinoma cells, but also differentiated neonatal rat cardiac myocytes (NRMCs).

After treatment with 10 ug/ml peptide for just six hours, some of the NRMCs appear to be shmooing, like yeast responding to an a-factor gradient, and show an elongated morphology (FIG. 11A). In addition, a number of cells can be seen to have fused. After 18 hours of treatment with 25 ug/ml peptide, more extensive myocytes morphogenesis and fusion is observed (FIG. 11B). After 72 hours of exposure to the peptide, the NRMCs have fused into beating myosheets (FIG. 12). The peptide also induces the differentiation of fibroblasts and fusion/cross-talk between different cell types, as demonstrated by the morphogenesis of the fibroblasts and tubulin and actin cytoskeletal rearrangements occurring at the site of interaction between an NRMC and an adjacent fibroblast in FIG. 12. Consequently, the prelamin A pre peptide not only determines tissue organization amongst the same type of cells, but also intracellular organization between different cell and tissue types.

The finding that the peptide can induce morphogensis and fusion of differentiated NRMCs indicates that these cells are not fully differentiated and that their morphology, intercellular organization and tissue architecture are still malleable. However, when adult rabbit cardiac myocytes were treated with the prelamin A pre peptide, cytoskeletal rearrangements were induced and there was a dissolution of the actin cytoskeleton. This result demonstrates that under certain conditions the peptide can induce morphogensis and restructuring of differentiated cells and tissues.

Example 4

The following example demonstrates that changes in lamin and cytoskeletal architecture in HeLa cervical carcinoma cells are communicated to adjacent cells from cells transfected with different GFP mutants.

Human HeLa cervical carcinoma cells were transfected with GFP-prelamin A fusion protein constructs (FIGS. 13B-C, and 13E-13L) and stained for emerin, the lamina associated nuclear membrane protein responsible for X-linked Emery-Dreifuss muscular dystrophy. Initially, it was noted that expression of the wild type (FIGS. 13A and 13D) and some of the mutant GFP-prelamin A constructs resulted in alterations to the emerin staining pattern, and that these alterations were being communicated and replicated in adjacent untransfected nuclei (FIGS. 13A-13L). Furthermore, the emerin staining (FIGS. 13D-13F and 13J-13L) appeared to also be present in the intermediate filament cytoskeleton, and this extra-nuclear staining pattern, as well as the spacing between and arrangement of nuclei was altered by prelamin A expression (FIGS. 13A-13L). Given the Examples and data provided above, these results again demonstrate that prelamin A pre peptide signaling and lamina architecture determine cytoskeletal and intercellular tissue matrix architecture in non-muscle cell types. Furthermore, these results suggest a putative role for using mutant prelamin A proteins and prelamin A pre peptide in therapeutic strategies for the treatment of cancers.

Example 5

The following example demonstrates that prelamin A pre peptide induces differentiation of embryonic stem cells.

ES cells were contacted with the prelamin A pre peptide (courtesy of Dr. Chris Hogan, University of Colorado).

FIGS. 14A-14C show a 10× control. The ES cells have round distinct nuclei and are expressing tubulin. The prelamin A signal is primarily in extracellular aggregates, though nuclear staining can also be detected. After 6 hours of treatment with prelamin A pre peptide at 1 μg/ml (FIGS. 14D-14F), the DNA morphology in the ES cells has changed drastically, there is no longer any tubulin expression, and there is extensive secretion of the pre peptide.

It is not likely that all of the tubulin in the cell could have non-specifically degraded in just 6 hours, indicating the protein is being specifically degraded. As tubulin is required for chromosomal segregation, these cells are likely cell cycle arrested, as would appear to be the case based on the DNA morphology. The change in DNA morphology, concomitant change in gene expression, apparent cell cycle arrest and secretion of the pre peptide in response to peptide treatment, all indicate the peptide is inducing differentiation of these ES cells.

Example 6

The following example demonstrates that the chicken variant of the prelamin A pre peptide induces the differentiation of skeletal myoblasts.

The chicken homologue of the human prelamin A peptide (SEQ ID NO: 17) was chemically synthesized and farnesylated and carboxymethylated. The lyophilized peptide was dissolved at 10 mg/ml in 50% DMSO/50% water. Actively proliferating C2C12 cells were treated with the chicken prelamin A peptide at 40 ug/ml on plastic chamber slides in complete DMEM media containing 10% fetal bovine serum (FBS). After 20 hours the cells were fixed in methanol/acetone and then immunostained with a rabbit anti-desmin primary antibody and a Texas Red conjugated anti-rabbit secondary antibody. Cover slips were mounted with media containing DAPI.

Within 20 hours, the chicken prelamin A peptide induced cell cycle arrest, myoblast morphogenesis and fusion. In FIGS. 15B and 15D mitotic arrest is clearly evident. Furthermore, intensely staining round cells that are in the process of cell division are evident in the control (FIGS. 15A and 15C) but largely absent from the treated samples (FIGS. 15B and 15D), directly demonstrating the chicken peptide has induced cell cycle arrest.

At low magnification, peptide treatment results in a more distinct cytoskeletal staining pattern (FIG. 15B) than the diffuse signal seen in the controls (FIG. 15A). Furthermore, large areas of fused cells are clearly evident throughout the field (FIG. 15B).

In higher magnification images the actively dividing cells in the untreated control containing two hemispheres of dividing DNA are clearly visible (FIG. 15C). Even in this small field, numerous intensely staining round dividing cells are present in the control, as well as a number of cells which have just divided. At higher magnification, one can see that the desmin staining pattern in the control cells remains diffuse with little filamentous character as would be necessary for the cells to continue dividing. In the fields of peptide-treated cells a distinct and extensive filamentous desmin cytoskeleton is clearly evident as the cells have differentiated (FIG. 15D). The cell cytoskeleton can be seen to be initiating at the nuclear interface and growing outward towards the plasma membrane, whereas in most treated cells cytoskeleton formation is already extensive at the 20 hour time-point. Differentiation is also indicated by the larger size and expanded DNA of the treated cells.

These results demonstrate that the chicken prelamin A peptide induces cell cycle arrest, cellular morphogenesis and cytoskeleton formation, and skeletal myoblast fusion when topically applied to proliferating myoblasts in complete growth media containing 10% FBS. Together, these data demonstrate that the chicken prelamin A peptide functions analogously to the human prelamin A peptide as an extracellular signal for myoblast differentiation.

Example 7

The following example demonstrates that the prelamin A peptide induces differentiation of preadipocytes.

NIH3T3-L1 preadipocytes treated with the chicken prelamin A peptide for 72 hours differentiated into adipocytes cells (FIG. 16). While the control cells remained small, a large number of peptide-treated cells became very large and stained positively with oil red 0, which is used to identify the fat droplets in differentiating adipocytes (FIG. 16). Based on the change in morphology and the oil red 0 staining, the chicken peptide induces the differentiation of NIH3T3-L1 cells into adipocytes.

Example 8

The following example demonstrates that the prelamin A peptide induces differentiation toward multiple different cell types, the interaction of different cell types and tissue formation.

While treatment of C2C12 cells with higher concentrations of the prelamin A peptide results in cell fusion and myotube formations, topical exposure of these same cells to lower peptide concentrations led to differentiation and morphogenesis representing a number of different cell types, and to intercellular interactions and tissue formation (FIG. 17).

Cells treated with low concentrations of the prelamin A peptide excrete ECM. The cells also differentiated into a number of different cell morphologies that interacted with the ECM and with each other. Some treated cells displayed the multinucleate morphology and physical appearance of osteoclasts; bone cells involved in the recycling and growth of bone tissue. Other treated cells formed axonal-like extensions which interacted with the ECM and appear to be neural cells. Still other treated cells extended vessels between cell bodies and directly interacted. These results demonstrate that the prelamin A peptide can induce cells to differentiate towards multiple different fates and cell types which interact and form tissue.

Example 9

The following example demonstrates that the prelamin A peptide induces differentiation of neural stem cells into nerve cells, including glial cells.

Mouse neural stem cells were treated with the prelamin A peptide for two days (FIGS. 18D-18F) and were then fixed, immunostained for lamin A/C expression (FIGS. 18A and 18D) and tubulin expression (FIGS. 18B and 18E), and stained for DNA with DAPI (FIGS. 18C and 18F). Peptide treatment inhibited cell proliferation and induced changes in cell morphology and tubulin expression (FIG. 18A-18F). Tubulin expression in untreated cells is cytoplasmic and relatively diffuse, and tubulin is excluded from the cell nucleus. In peptide-treated cells a distinct filamentous tubulin staining pattern is seen initiating at the cell nucleus and extending into the cell body. Furthermore, these experiments reveal the peptide-treated cells are larger than the controls, more widely spaced, are interacting around certain loci and have undergone morphogenesis and taken on the appearance of nerve cells, including glial cells. Together, peptide-induced inhibition of cell proliferation, changes in tubulin expression, localization and structure, cell morphogenesis and interaction demonstrate that the prelamin A peptide induces the differentiation of neural stem cells.

Example 10

The following example demonstrates that the prelamin A pre peptide induces the differentiation of embryonic carcinoma cells.

Mouse F9 embryonic carcinoma cells were treated with the prelamin A peptide for two days (FIGS. 19D-19F) and then were fixed, immunostained for lamin A/C expression (FIGS. 19A and 19D) and keratin 8 expression (FIGS. 19B and 19E), and stained for DNA with DAPI (FIGS. 19C and 19F). Keratin 8 and lamin A/C co-localize in all cells. Peptide treatment severely inhibits cell proliferation and induces changes in cell morphology, DNA morphology, intercellular organization, and lamin A/C and keratin 8 expression (FIGS. 19A-19F). Both keratin 8 and lamin A/C display distinct perinuclear filamentous staining, with greater expression towards the center of cell colonies than the periphery, in untreated F9 cells. In contrast, keratin 8 and lamin A/C show intense peripheral staining in peptide-treated cell colonies with a greatly reduced expression towards the center of the treated cell colonies. The treated cells display a DNA morphology consistent with expansion of DNA into heterochromatin. Furthermore, cells at the edges of the treated colonies display altered cell morphology and are extending away from the colony, and intercellular spacing in the treated cell colonies has clearly been expanded. Together, prelamin A peptide-induced inhibition of cell proliferation, changes in lamin A/C and keratin 8 expression, cell morphogenesis, DNA expansion and alteration of intercellular organization demonstrate the prelamin A peptide induces the differentiation of embryonic carcinoma cells.

REFERENCES

1. Fatkin, D. et al. Missense mutations in the rod domain of the lamin A/C gene as causes of dilated cardiomyopathy and conduction-system disease. N Engl J Med 341, 1715-24 (1999).
2. Bonne, G. et al. Mutations in the gene encoding lamin A/C cause autosomal dominant Emery-Dreifuss muscular dystrophy. Nature Genet. 21, 285-288 (1999).
3. Muchir, A. et al. Identification of mutations in the gene encoding lamin A/C in the autosomal dominant form of limb-girdle muscular dystrophy with cardiac involvement (LGMD1B). Neuromuscular Disorders 9, 500 (1999).
4. Raharjo, W. H., Enarson, P., Sullivan, T., Stewart, C. L. & Burke, B. Nuclear envelope defects associated with LMNA mutations cause dilated cardiomyopathy and Emery-Dreifuss muscular dystrophy. J Cell Sci 114, 4447-57. (2001).
5. Novelli, G. et al. Mandibuloacral dysplasia is caused by a mutation in LMNA encoding lamin A/C. Am J Hum Genet 71, 426-31. (2002).
6. Eriksson, M. et al. Recurrent de novo point mutations in lamin A cause Hutchinson-Gilford progeria syndrome. Nature 423, 293-8 (2003).
7. Moulson, C. L. et al. Homozygous and compound heterozygous mutations in ZMPSTE24 cause the laminopathy restrictive dermopathy. J Invest Dermatol 125, 913-9 (2005).
8. Mattout, A., Dechat, T., Adam, S. A., Goldman, R. D. & Gruenbaum, Y. Nuclear lamins, diseases and aging. Curr Opin Cell Biol (2006).
9. Fong, L. G. et al. A protein farnesyltransferase inhibitor ameliorates disease in a mouse model of progeria. Science 311, 1621-3 (2006).
10. Scaffidi, P. & Misteli, T. Lamin A-Dependent Nuclear Defects in Human Aging. Science (2006).
11. Libotte, T. et al. Lamin A/C-dependent localization of Nesprin-2, a giant scaffolder at the nuclear envelope. Mol Biol Cell 16, 3411-24 (2005).
12. Haque, F. et al. SUN1 Interacts with Nuclear Lamin A and Cytoplasmic Nesprins To Provide a Physical Connection between the Nuclear Lamina and the Cytoskeleton. Mol Cell Biol 26, 3738-51 (2006).
13. Constantinescu, D., Gray, H. L., Sammak, P. J., Schatten, G. P. & Csoka, A. B. Lamin A/C expression is a marker of mouse and human embryonic stem cell differentiation. Stem Cells 24, 177-85 (2006).
14. Fuchs, E. & Weber, K. Intermediate filaments: structure, dynamics, function, and disease. Annu Rev Biochem 63, 345-82 (1994).
15. Taylor, M. R. et al. Natural history of dilated cardiomyopathy due to lamin A/C gene mutations. J Am Coll Cardiol 41, 771-80 (2003).
16. Corrigan, D. P. et al. Prelamin A endoproteolytic processing in vitro by recombinant Zmpste24. Biochem J 387, 129-38 (2005).
17. Hennekes, H. & Nigg, E. A. The role of isoprenylation in membrane attachment of nuclear lamins. A single point mutation prevents proteolytic cleavage of the lamin A precursor and confers membrane binding properties. J Cell Sci 107, 1019-29 (1994).
18. Lutz, R. J., Trujillo, M. A., Denham, K. S., Wenger, L. & Sinensky, M. Nucleoplasmic localization of prelamin A: implications for prenylation dependent lamin A assembly into the nuclear lamina. Proc Natl Acad Sci USA 89, 3000-4 (1992).
19. Kumagai, H., Kawamura, Y., Yanagisawa, K. & Komano, H. Identification of a human cDNA encoding a novel protein structurally related to the yeast membrane-associated metalloprotease, Step 24p. Biochim Biophys Acta 1426, 468-74 (1999).
20. Sullivan, T. et al. Loss of A-type lamin expression compromises nuclear envelope integrity leading to muscular dystrophy. J Cell Biol 147, 913-20 (1999).

21. Pendas, A. M. et al. Defective prelamin A processing and muscular and adipocyte alterations in Zmpste24 metalloproteinase-deficient mice. Nature Genetics 31, 94-9 (2002).
22. Bergo, M. O. et al. Zmpste24 deficiency in mice causes spontaneous bone fractures, muscle weakness, and a prelamin A processing defect. Proc Natl Acad Sci USA 99, 13049-54. (2002).
23. Cadinanos, J. et al. Identification, functional expression and enzymic analysis of two distinct CaaX proteases from Caenorhabditis elegans. Biochem J 370, 1047-54 (2003).
24. Menard, C. et al. Modulation of L-type calcium channel expression during retinoic acid-induced differentiation of H9C2 cardiac cells. J Biol Chem 274, 29063-70. (1999).
25. Frock, R. L. et al. Lamin A/C and emerin are critical for skeletal muscle satellite cell differentiation. Genes Dev 20, 486-500 (2006).
26. Pagano, M. et al. Differentiation of H9c2 cardiomyoblasts: The role of adenylate cyclase system. J Cell Physiol 198, 408-16 (2004).
27. Biben, C., Hadchouel, J., Tajbakhsh, S. & Buckingham, M. Developmental and tissue-specific regulation of the murine cardiac actin gene in vivo depends on distinct skeletal and cardiac muscle-specific enhancer elements in addition to the proximal promoter. Dev Biol 173, 200-12 (1996).
28. Knapp, J. R. et al. Loss of myogenin in postnatal life leads to normal skeletal muscle but reduced body size. Development 133, 601-10 (2006).
29. Pavlath, G. K., Rich, K., Webster, S. G. & Blau, H. M. Localization of muscle gene products in nuclear domains. Nature 337, 570-3. (1989).
30. Fong, L. G. et al. Prelamin A and lamin A appear to be dispensable in the nuclear lamina. J Clin Invest 116, 743-52 (2006).
31. U.S. Provisional Application Ser. No. 60/808,722, filed May 26, 2006.
32. Newport, J. W., K. L. Wilson, and W. G. Dunphy, A lamin-independent pathway for nuclear envelope assembly. J Cell Biol, 1990. 111(6 Pt 1): p. 2247-59.
33. Ozaki, T., et al., Complex formation between lamin A and the retinoblastoma gene product: identification of the domain on lamin A required for its interaction. Oncogene, 1994. 9(9): p. 2649-53.
34. Gotzmann, J. and R. Foisner, Lamins and lamin-binding proteins in functional chromatin organization. Crit Rev Eukaryot Gene Expr, 1999. 9(3-4): p. 257-65.
35. Haas, M. and E. Jost, Functional analysis of phosphorylation sites in human lamin A controlling lamin disassembly, nuclear transport and assembly. Eur J Cell Biol, 1993. 62(2): p. 237-47.
36. Slee, E. A., C. Adrain, and S. J. Martin, Executioner caspase-3, -6, and -7 perform distinct, non-redundant roles during the demolition phase of apoptosis. J Biol Chem, 2001. 276(10): p. 7320-6.
37. Kitten, G. T. and E. A. Nigg, The CaaX motif is required for isoprenylation, carboxyl methylation, and nuclear membrane association of lamin B2. J Cell Biol, 1991. 113(1): p. 13-23.
38. Izumi, M., et al., Head and/or CaaX domain deletions of lamin proteins disrupt preformed lamin A and C but not lamin B structure in mammalian cells. Mol Biol Cell, 2000. 11(12): p. 4323-37.
39. Fisher, D. Z., N. Chaudhary, and G. Blobel, cDNA sequencing of nuclear lamins A and C reveals primary and secondary structural homology to intermediate filament proteins. Proc Natl Acad Sci USA, 1986. 83(17): p. 6450-4.
40. Brodsky, G. L., et al., Lamin A/C gene mutation associated with dilated cardiomyopathy with variable skeletal muscle involvement. Circulation, 2000. 101(5): p. 473-6.
41. Shackleton, S., et al., LMNA, encoding lamin A/C, is mutated in partial lipodystrophy [see comments]. Nat Genet, 2000. 24(2): p. 153-6.
42. De Sandre-Giovannoli, A., et al., Homozygous defects in LMNA, encoding lamin A/C nuclear-envelope proteins, cause autosomal recessive axonal neuropathy in human (Charcot-Marie-Tooth disorder type 2) and mouse. Am J Hum Genet, 2002. 70(3): p. 726-36.
43. Lloyd, D. J., R. C. Trembath, and S. Shackleton, A novel interaction between lamin A and SREBP1: implications for partial lipodystrophy and other laminopathies. Hum Mol Genet, 2002. 11(7): p. 769-77.
44. Mounkes, L. C., et al., Expression of an LMNA-N195K variant of A-type lamins results in cardiac conduction defects and death in mice. Hum Mol Genet, 2005. 14(15): p. 2167-80.
45. Sullivan, T., et al., Loss of A-type lamin expression compromises nuclear envelope integrity leading to muscular dystrophy. J Cell Biol, 1999. 147(5): p. 913-20.
46. Mallampalli, M. P., et al., Inhibiting farnesylation reverses the nuclear morphology defect in a HeLa cell model for Hutchinson-Gilford progeria syndrome. Proc Natl Acad Sci USA, 2005. 102(40): p. 14416-21.
47. Toth, J. I., et al., Blocking protein farnesyltransferase improves nuclear shape in fibroblasts from humans with progeroid syndromes. Proc Natl Acad Sci USA, 2005. 102(36): p. 12873-8.
48. Yang, S. H., et al., Blocking protein farnesyltransferase improves nuclear blebbing in mouse fibroblasts with a targeted Hutchinson-Gilford progeria syndrome mutation. Proc Natl Acad Sci USA, 2005. 102(29): p. 10291-6.
49. Broers, J. L., et al., Dynamics of the nuclear lamina as monitored by GFP-tagged A-type lamins. J Cell Sci, 1999. 112 (Pt 20): p. 3463-75.
50. Elion, E. A., *Pheromone response, mating and cell biology*. Curr Opin Microbiol, 2000. 3(6): p. 573-81.
51. Wakelam, M. J., The fusion of myoblasts. Biochem J, 1985. 228(1): p. 1-12.
52. Ardati, A., et al., Statin-associated rhabdomyolysis. Pharmacoepidemiol Drug Saf, 2005. 14(4): p. 287.
53. Chen, E. H., et al., Control of myoblast fusion by a guanine nucleotide exchange factor, loner, and its effector ARF6. Cell, 2003. 114(6): p. 751-62.
54. Lockard, V. G. and S. Bloom, Trans-cellular desmin-lamin B intermediate filament network in cardiac myocytes. J Mol Cell Cardiol, 1993. 25(3): p. 303-9.
55. Capetanaki, Y., D. J. Milner, and G. Weitzer, Desmin in muscle formation and maintenance: knockouts and consequences. Cell Struct Funct, 1997. 22(1): p. 103-16.

While various embodiments of the present invention have been described in detail, it is apparent that modifications and adaptations of those embodiments will occur to those skilled in the art. It is to be expressly understood, however, that such modifications and adaptations are within the scope of the present invention.

What is claimed is:

1. A method to induce differentiation of a cell, comprising contacting a cell selected from the group consisting of a myoblast and an adipocyte stem cell, with the prelamin A prepeptide of SEQ ID NO:2, in vitro wherein contact of the cell with the prelamin A prepeptide induces differentiation of the cell.

2. The method of claim 1, wherein the cell is an adipocyte stem cell.

3. The method of claim 1, wherein the cell is a cardiac myoblast.

4. The method of claim 1, wherein the cell is a skeletal myoblast.

* * * * *

SEQUENCE LISTING

<160> NUMBER OF SEQ ID NOS: 24

<210> SEQ ID NO 1
<211> LENGTH: 57
<212> TYPE: DNA
<213> ORGANISM: Homo sapiens

<400> SEQUENCE: 1
ctcctgggca actccagccc ccgaacccag agcccccaga actgcagcat catgtaa       57

<210> SEQ ID NO 2
<211> LENGTH: 15
<212> TYPE: PRT
<213> ORGANISM: Homo sapiens

<400> SEQUENCE: 2

Leu Leu Gly Asn Ser Ser Pro Arg Thr Gln Ser Pro Gln Asn Cys
1               5                   10                  15

<210> SEQ ID NO 3
<211> LENGTH: 3181
<212> TYPE: DNA
<213> ORGANISM: Homo sapiens

<400> SEQUENCE: 3
actcagtgtt cgcgggagcg ccgcacctac accagccaac ccagatcccg aggtccgaca      60
gcgcccggcc cagatcccca cgcctgccag gagcaagccg agagccagcc ggccggcgca     120
ctccgactcc gagcagtctc tgtccttcga cccgagcccc gcgcccttc cgggacccct      180 gccccgcggg cagcgctgcc aacctgccgg ccatggagac cccgtcccag cggcgcgcca     240
cccgcagcgg ggcgcaggcc agctccactc cgctgtcgcc cacccgcatc acccggctgc     300
aggagaagga ggacctgcag gagctcaatg atcgcttggc ggtctacatc gaccgtgtgc     360
gctcgctgga aacggagaac gcagggctgc gccttcgcat caccgagtct gaagaggtgg     420
tcagccgcga ggtgtccggc atcaaggcgc cctacgaggc cgagctcggg gatgcccgca     480
agacccttga ctcagtagcc aaggagcgcg cccgcctgca gctggagctg agcaaagtgc     540
gtgaggagtt taaggagctg aaagcgcgca ataccaagaa ggagggtgac ctgatagctg     600
ctcaggctcg gctgaaggac ctggaggctc tgctgaactc caaggaggcc gcactgagca     660
ctgctctcag tgagaagcgc acgctggagg cgagctgca tgatctgcgg ggccaggtgg      720
ccaagcttga ggcagcccta ggtgaggcca agaagcaact tcaggatgag atgctgcggc     780
gggtggatgc tgagaacagg ctgcagacca tgaaggagga actggacttc cagaagaaca     840
tctacagtga ggagctgcgt gagaccaagc gccgtcatga gacccgactg gtggagattg     900
acaatgggaa gcagcgtgag tttgagagcc ggctggcgga tgcgctgcag gaactgcggg     960
cccagcatga ggaccaggtg gagcagtata agaaggagct ggagaagact tattctgcca    1020
agctggacaa tgccaggcag tctgctgaga ggaacagcaa cctggtgggg ctgcccacg     1080 aggagctgca gcagtcgcgc atccgcatcg acagcctctc tgcccagctc agccagctcc    1140
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggccctgg    1320
acatggagat ccacgcctac cgcaagctct ggagggcga ggaggagagg ctacgcctgt    1380
cccccagccc tacctcgcag cgcagccgtg gccgtgcttc ctctcactca tcccagacac    1440

```
agggtgggggg cagcgtcacc aaaaagcgca aactggagtc cactgagagc cgcagcagct   1500
tctcacagca cgcacgcact agcgggcgcg tggccgtgga ggaggtggat gaggagggca   1560
agtttgtccg gctgcgcaac aagtccaatg aggaccagtc catgggcaat tggcagatca   1620
agcgccagaa tggagatgat cccttgctga cttaccggtt cccaccaaag ttcaccctga   1680
aggctgggca ggtggtgacg atctgggctg caggagctgg ggccacccac agccccccta   1740
ccgacctggt gtggaaggca cagaacacct ggggctgcgg gaacagcctg cgtacggctc   1800
tcatcaactc cactggggaa gaagtggcca tgcgcaagct ggtgcgctca gtgactgtgg   1860
ttgaggacga cgaggatgag gatggagatg acctgctcca tcaccaccac ggctcccact   1920
gcagcagctc gggggacccc gctgagtaca acctgcgctc gcgcaccgtg ctgtgcggga   1980
cctgcgggca gcctgccgac aaggcatctg ccagcggctc aggagcccag gtgggcggac   2040
ccatctcctc tggctcttct gcctccagtg tcacggtcac tcgcagctac cgcagtgtgg   2100
ggggcagtgg gggtggcagc ttcggggaca atctggtcac ccgctcctac ctcctgggca   2160
actccagccc ccgaacccag agcccccaga actgcagcat catgtaatct gggacctgcc   2220
aggcaggggt gggggtggag gcttcctgcg tcctcctcac ctcatgccca ccccctgccc   2280
tgcacgtcat gggagggggc ttgaagccaa agaaaaataa ccctttggtt ttttcttct   2340
gtatttttt ttctaagaga agttattttc tacagtggtt ttatactgaa ggaaaaacac   2400
aagcaaaaaa aaaaaaaagc atctatctca tctatctcaa tcctaatttc cctcccttc   2460
cttttccctg cttccaggaa actccacatc tgccttaaaa ccaaagaggg cttcctctag   2520
aagccaaggg aaaggggtgc ttttatagag gctagcttct gcttttctgc cctggctgct   2580
gccccccaccc cggggaccct gtgacatggt gcctgagagg caggcataga ggcttctccg   2640
ccagcctcct ctggacggca ggctcactgc caggccagcc tccgagaggg agagagagag   2700
agagaggaca gcttgagccg ggcccctggg cttggcctgc tgtgattcca ctacacctgg   2760
ctgaggttcc tctgcctgcc ccgccccccag tccccacccc tgccccagc cccggggtga   2820
gtccattctc ccaggtacca gctgcgcttg cttttctgta ttttatttag acaagagatg   2880
ggaatgaggt gggaggtgga agaagggaga agaaaaggtga gtttgagctg ccttccctag   2940
ctttagaccc tgggtgggct ctgtgcagtc actggaggtt gaagccaagt gggggtgctgg   3000
gaggagggag agggaggtca ctggaaaggg gagagcctgc tggcacccac cgtggaggag   3060
gaaggcaaga gggggtggag gggtgtggca gtggttttgg caaacgctaa agagcccttg   3120
cctccccatt tcccatctgc accccttctc tcctccccaa atcaatacac tagttgtttc   3180
t                                                                   3181
```

<210> SEQ ID NO 4
<211> LENGTH: 664
<212> TYPE: PRT
<213> ORGANISM: Homo sapiens

<400> SEQUENCE: 4

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

```
Glu Ser Glu Glu Val Val Ser Arg Glu Val Ser Gly Ile Lys Ala Ala
 65                  70                  75                  80

Tyr Glu Ala Glu Leu Gly Asp Ala Arg Lys Thr Leu Asp Ser Val Ala
                 85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
```

```
                    485                 490                 495
Ile Trp Ala Ala Gly Ala Gly Ala Thr His Ser Pro Thr Asp Leu
            500                 505                 510
Val Trp Lys Ala Gln Asn Thr Trp Gly Cys Gly Asn Ser Leu Arg Thr
            515                 520                 525
Ala Leu Ile Asn Ser Thr Gly Glu Glu Val Ala Met Arg Lys Leu Val
            530                 535                 540
Arg Ser Val Thr Val Val Glu Asp Asp Glu Asp Gly Asp
545                 550                 555                 560
Leu Leu His His His Gly Ser His Cys Ser Ser Gly Asp Pro
                565                 570                 575
Ala Glu Tyr Asn Leu Arg Ser Arg Thr Val Leu Cys Gly Thr Cys Gly
            580                 585                 590
Gln Pro Ala Asp Lys Ala Ser Ala Gly Ser Gly Ala Gln Val Gly
            595                 600                 605
Gly Pro Ile Ser Ser Gly Ser Ser Ala Ser Ser Val Thr Val Thr Arg
            610                 615                 620
Ser Tyr Arg Ser Val Gly Gly Ser Gly Gly Ser Phe Gly Asp Asn
625                 630                 635                 640
Leu Val Thr Arg Ser Tyr Leu Leu Gly Asn Ser Ser Pro Arg Thr Gln
                645                 650                 655
Ser Pro Gln Asn Cys Ser Ile Met
            660

<210> SEQ ID NO 5
<211> LENGTH: 1938
<212> TYPE: DNA
<213> ORGANISM: Homo sapiens

<400> SEQUENCE: 5
atggagaccc cgtcccagcg gcgcgccacc cgcagcgggg cgcaggccag ctccactccg      60
ctgtcgccca cccgcatcac ccggctgcag agaaggagg acctgcagga gctcaatgat     120
cgcttggcgg tctacatcga ccgtgtgcgc tcgctggaaa cggagaacgc agggctgcgc     180
cttcgcatca ccgagtctga agaggtggtc agccgcgagg tgtccggcat caaggccgcc     240
tacgaggccg agctcgggga tgcccgcaag acccttgact cagtagccaa ggagcgcgcc     300
cgcctgcagc tggagctgag caaagtgcgt gaggagttta aggagctgaa agcgcgcaat     360
accaagaagg agggtgacct gatagctgct caggctcggc tgaaggacct ggaggctctg     420
ctgaactcca aggaggccgc actgagcact gctctcagtg agaagcgcac gctggagggc     480
gagctgcatg atctgcgggg ccaggtggcc aagcttgagg cagccctagg tgaggccaag     540
aagcaacttc aggatgagat gctgcggcgg gtggatgctg agaacaggct gcagaccatg     600
aaggaggaac tggacttcca gaagaacatc tacagtgagg agctgcgtga gaccaagcgc     660
cgtcatgaga cccgactggt ggagattgac aatgggaagc agcgtgagtt tgagagccgg     720
ctggcggatg cgctgcagga actgcgggcc cagcatgagg accaggtgga gcagtataag     780
aaggagctgg agaagactta ttctgccaag ctggacaatg ccaggcagtc tgctgagagg     840
aacagcaacc tggtggggc tgcccacgag gagctgcagc agtcgcgcat ccgcatcgac     900
agcctctctg cccagctcag ccagctccag aagcagctgg cagccaagga ggcgaagctt     960
cgagacctgg aggactcact ggcccgtgag cgggacacca gcggcggct gctggcggaa    1020 aaggagcggg agatggccga gatgcgggca aggatgcagc agcagctgga cgagtaccag    1080
gagcttctgg acatcaagct ggccctggac atggagatcc acgcctaccg caagctcttg    1140
```

```
gagggcgagg aggagaggct acgcctgtcc cccagcccta cctcgcagcg cagccgtggc    1200
cgtgcttcct ctcactcatc ccagacacag ggtgggggca gcgtcaccaa aaagcgcaaa    1260
ctggagtcca ctgagagccg cagcagcttc tcacagcacg cacgcactag cgggcgcgtg    1320
gccgtggagg aggtggatga ggagggcaag tttgtccggc tgcgcaacaa gtccaatgag    1380
gaccagtcca tgggcaattg gcagatcaag cgccagaatg agatgatccc cttgctgact    1440
taccggttcc caccaaagtt caccctgaag gctgggcagg tggtgacgat ctgggctgca    1500
ggagctgggg ccacccacag ccccctacc gacctggtgt ggaaggcaca gaacacctgg    1560
ggctgcggga acagcctgcg tacggctctc atcaactcca ctggggaaga agtggccatg    1620
cgcaagctgg tgcgctcagt gactgtggtt gaggacgacg aggatgagga tggagatgac    1680
ctgctccatc accaccacgg ctcccactgc agcagctcgg gggaccccgc tgagtacaac    1740
ctgcgctcgc gcaccgtgct gtgcgggacc tgcgggcagc tgccgacaa ggcatctgcc    1800 agcggctcag gagcccaggt gggcggaccc atctcctctg ctcttctgc ctccagtgtc    1860 acggtcactc gcagctaccg cagtgtgggg ggcagtgggg gtggcagctt cggggacaat    1920
ctggtcaccc gctcctac                                                  1938

<210> SEQ ID NO 6
<211> LENGTH: 646
<212> TYPE: PRT
<213> ORGANISM: Homo sapiens

<400> SEQUENCE: 6

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
```

```
            225                 230                 235                 240
Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
                260                 265                 270

Asn Ala Arg Gln Ser Ala Glu Arg Asn Ser Asn Leu Val Gly Ala Ala
                275                 280                 285

His Glu Glu Leu Gln Gln Ser Arg Ile Arg Ile Asp Ser Leu Ser Ala
            290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
                340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
        370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
                420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
        450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
                500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
        530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
                580                 585                 590

Gln Pro Ala Asp Lys Ala Ser Ala Ser Gly Ser Gly Ala Gln Val Gly
            595                 600                 605

Gly Pro Ile Ser Ser Gly Ser Ser Ala Ser Ser Val Thr Val Thr Arg
        610                 615                 620

Ser Tyr Arg Ser Val Gly Gly Ser Gly Gly Ser Phe Gly Asp Asn
625                 630                 635                 640

Leu Val Thr Arg Ser Tyr
                645
```

<210> SEQ ID NO 7
<211> LENGTH: 2032
<212> TYPE: DNA
<213> ORGANISM: Homo sapiens

<400> SEQUENCE: 7

```
actcagtgtt cgcgggagcg ccgcacctac accagccaac ccagatcccg aggtccgaca      60
gcgcccggcc cagatcccca cgcctgccag gagcaagccg agagccagcc ggccggcgca     120
ctccgactcc gagcagtctc tgtccttcga cccgagcccc gcgcccttc cgggacccct      180
gccccgcggg cagcgctgcc aacctgccgg ccatggagac cccgtcccag cggcgcgcca     240
cccgcagcgg ggcgcaggcc agctccactc cgctgtcgcc cacccgcatc acccggctgc     300
aggagaagga ggacctgcag gagctcaatg atcgcttggc ggtctacatc gaccgtgtgc     360
gctcgctgga aacggagaac gcagggctgc gccttcgcat caccgagtct gaagaggtgg     420
tcagccgcga ggtgtccggc atcaaggcgc cctacgaggc cgagctcggg gatgcccgca     480
agaccccttga ctcagtagcc aaggagcgcg cccgcctgca gctggagctg agcaaagtgc     540
gtgaggagtt taaggagctg aaagcgcgca ataccaagaa ggagggtgac ctgatagctg     600
ctcaggctcg gctgaaggac ctggaggctc tgctgaactc caaggaggcc gcactgagca     660
ctgctctcag tgagaagcgc acgctggagg gcgagctgca tgatctgcgg ggccaggtgg     720
ccaagcttga ggcagcccta ggtgaggcca agaagcaact tcaggatgag atgctgcggc     780
gggtggatgc tgagaacagg ctgcagacca tgaaggagga actggacttc agaagaaca     840
tctacagtga ggagctgcgt gagaccaagc gccgtcatga cccgactg gtggagattg        900
acaatgggaa gcagcgtgag tttgagagcc ggctggcgga tgcgctgcag gaactgcggg     960
cccagcatga ggaccaggtg gagcagtata agaaggagct ggagaagact tattctgcca    1020
agctggacaa tgccaggcag tctgctgaga ggaacagcaa cctggtgggg gctgccacg     1080
aggagctgca gcagtcgcgc atccgcatcg acagcctctc tgcccagctc agccagctcc    1140
agaagcagct ggcagccaag gaggcgaagc ttcgagacct ggaggactca ctggcccgtg    1200
agcgggacac cagccggcgg ctgctggcgg aaaaggagcg ggagatggcc gagatgcggg    1260
caaggatgca gcagcagctg gacgagtacc aggagcttct ggacatcaag ctggccctgg    1320
acatggagat ccacgcctac cgcaagctct tggaggcga ggaggagagg ctacgcctgt     1380
cccccagccc tacctcgcag cgcagccgtg gccgtgcttc ctctcactca tcccagacac    1440
agggtggggg cagcgtcacc aaaaagcgca aactggagtc cactgagagc cgcagcagct    1500
tctcacagca cgcacgcact agcgggcgcg tggccgtgga ggaggtggat gaggagggca    1560
agtttgtccg gctgcgcaac aagtccaatg gaccagtc catgggcaat tggcagatca     1620
agcgccagaa tggagatgat cccttgctga cttaccggtt cccaccaaag ttcaccctga    1680
aggctgggca ggtggtgacg atctgggctg caggagctgg ggccacccac agccccccta    1740
ccgacctggt gtgaaggca cagaacaccc tggggctgcgg aacagcctg cgtacggctc     1800
tcatcaactc cactggggaa gaagtggcca tgcgcaagct ggtgcgctca gtgactgtgg    1860
ttgaggacga cgaggatgag gatggagatg acctgctcca tcaccaccac gtgagtggta    1920
gccgccgctg aggccgagcc tgcactgggg ccacccagcc aggcctgggg gcagcctctc    1980
cccagcctcc ccgtgccaaa aatctttca ttaaagaatg tttttggaact tt            2032
```

<210> SEQ ID NO 8
<211> LENGTH: 2354
<212> TYPE: DNA

<213> ORGANISM: Mus musculus

<400> SEQUENCE: 8

```
ccacgcctgc caggagcgag cttcgccggc tcgctgtccc cctgagcagc ctctgtcctt    60
ctgtccaagt cccgcgccct tctcgggacc cctgcccagc gggcagcact gtcaccctgc   120
cggccatgga daccccgtca cagcggcgcg ccacccgcag tggggcgcag gccagctcta   180
ccccactgtc gcccactcgg atcacccggc tgcaggagaa ggaggacctg caggagctca   240
atgaccgcct ggccgtgtac atcgatcgcg tgcgttccct ggagaccgag aacgcggggc   300
tgcgccttcg catcactgag tctgaagagg tggtcagccg agaggtgtcc ggcatcaagg   360
cggcctacga ggccgagctg ggggatgccc gcaagaccct tgattctgtg ccaaggagc    420
gcgcccgcct ccagctagag ctgagcaaag tgcgtgagga gttcaaggag ctgaaggctc   480
gcaacaccaa gaaggagggg gacttgttgg ctgcgcaggc ccggctcaag gacctcgagg   540
ctcttctcaa ctccaaggaa gctgccctga gcactgctct cagtgagaag cgcacattgg   600
agggcgagct ccatgacctg cggggggcagg tagccaagct tgaggcggcc ctgggagagg   660
ctaagaagca gcttcaggat gagatgctga ggcgagtgga tgctgagaac aggctacaga   720
cgctgaagga ggagcttgac ttccagaaga acatttacag cgaggaactg cgtgagacca   780
agcgccggca tgagacgcgg cttgtggaga tcgataacgg gaagcagcga gagtttgaga   840
gccggctggc agatgccctg caggagctgc gggctcagca tgaggaccag gtggaacagt   900
ataagaagga gctagaaaag acatactccg ccaagctgga taatgccagg cagtctgctg   960
agaggaacag caacctcgtg ggggctgccc atgaggaact gcagcagtct cgaatccgca  1020
ttgacagcct ctcggcccag ctcagccagc tccaaaagca gttggcagcc aaggaggcaa  1080
agctgcgtga cctggaggac tcgctggccc gtgagcgcga taccagccgg cgcctgctgg  1140
ctgagaaaga gcgagagatg gcggagatgc gggcgaggat gcagcagcag ctggacgagt  1200
accaggagct gctggacatc aagctggccc tggacatgga gatccatgcc tatcgaaagc  1260
tgctggaggg cgaggaggag aggctgcgc tgtcccccag ccctacctcg cagcgcagcc  1320
gtggccgcgc ctcctcccac tcatcccagt ctcagggtgg aggcagcgtc accaaaaagc  1380
gcaagctgga gtcttccgag agccggagca gcttctcgca gcatgctcgc actagcgggc  1440
gtgtggcggt agaggaagtc gatgaagagg gaaagttcgt gcggctgcgc aacaagtcca  1500
acgaggacca gtccatgggc aactggcaga tcaggcgtca gaatggtgac gatcctttga  1560
tgacctatcg cttcccaccg aagttccacc taaaggctgg gcaggtggtg acgatctggg  1620
cttcaggagc tggggccacc catagccccc ctactgactt ggtgtggaag gcgcagaaca  1680
cctggggctg tgggagcagc cttcgcaccg ctctcatcaa ctccactgga gaagaagtgg  1740
ccatgcgcaa gctggtgcgc tcactgacca tggttgagga caatgaggat gacgacgagg  1800
atggagaaga gctcctccat caccaccgtg gttcccactg cagcggctcg ggggaccccg  1860
ctgagtacaa cctgcgctca cgcaccgtgc tgtgcgggac gtgtgggcag cctgctgaca  1920
aggctgccgg tggagcggga gcccaggtgg gcggatccat ctcctctggc tcttctgcct  1980
ccagtgtcac agtcactcga agcttccgca gtgtgggggg cagtgggggt ggcagcttcg  2040
gggacaacct agtcacccgc tcctacctcc tgggcaactc cagtccccgg agccagagct  2100
cccagaactg cagcatcatg taatctggga cctgccaggc agggctgggg gcagaggcca  2160
cctgctcccc cctcaccaca tgccacctcc tgtctgctcc ttaggagagc aggcctgaag  2220
ccaaagaaaa atttatcccc tgcctttggt tttttttttt tttcttctat tttttttttc  2280
```

-continued

```
tttttctaag agaagttatt ttctacagtg gttttatact gaaggaaaaa ctcaagcaaa    2340
aaaaaaaaaa aaaa                                                     2354
```

<210> SEQ ID NO 9
<211> LENGTH: 665
<212> TYPE: PRT
<213> ORGANISM: Mus musculus

<400> SEQUENCE: 9

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Leu
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Leu Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365
```

```
Leu Asp Met Glu Ile His Ala Tyr Arg Lys Leu Leu Glu Gly Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Gln Ser Gln Gly Gly Gly Ser Val Thr
                405                 410                 415

Lys Lys Arg Lys Leu Glu Ser Ser Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Arg Arg Gln Asn Gly Asp Asp Pro Leu Met Thr
465                 470                 475                 480

Tyr Arg Phe Pro Pro Lys Phe Thr Leu Lys Ala Gly Gln Val Val Thr
                485                 490                 495

Ile Trp Ala Ser Gly Ala Gly Ala Thr His Ser Pro Pro Thr Asp Leu
            500                 505                 510

Val Trp Lys Ala Gln Asn Thr Trp Gly Cys Gly Ser Ser Leu Arg Thr
    515                 520                 525

Ala Leu Ile Asn Ser Thr Gly Glu Glu Val Ala Met Arg Lys Leu Val
530                 535                 540

Arg Ser Leu Thr Met Val Glu Asp Asn Glu Asp Asp Glu Asp Gly
545                 550                 555                 560

Glu Glu Leu Leu His His Arg Gly Ser His Cys Ser Gly Ser Gly
                565                 570                 575

Asp Pro Ala Glu Tyr Asn Leu Arg Ser Arg Thr Val Leu Cys Gly Thr
            580                 585                 590

Cys Gly Gln Pro Ala Asp Lys Ala Ala Gly Ala Gly Ala Gln Val
    595                 600                 605

Gly Gly Ser Ile Ser Ser Gly Ser Ser Ala Ser Ser Val Thr Val Thr
            610                 615                 620

Arg Ser Phe Arg Ser Val Gly Gly Ser Gly Gly Ser Phe Gly Asp
625                 630                 635                 640

Asn Leu Val Thr Arg Ser Tyr Leu Leu Gly Asn Ser Ser Pro Arg Ser
                645                 650                 655

Gln Ser Ser Gln Asn Cys Ser Ile Met
            660                 665

<210> SEQ ID NO 10
<211> LENGTH: 2388
<212> TYPE: DNA
<213> ORGANISM: Gallus gallus

<400> SEQUENCE: 10 cccccaccg cccccaccg ccccccaccc gcggtcccc tcggagctcc gccgcgcccc      60
tccgtgcgcc gtccgccgtc cgccgtccgc cgcccccga cggctcttct ccgcccgccc     120
ggcgcccccg cagcgttccc cgcccgccgc ccgccgtccc ggggtcgcac cgccgccccc     180
cgcccagccg ccatgtccac cccgtcccag cggaggagcg gccgcggcgg cggcccttcg     240
gggacccctc tgtccccgac gcgcatcacc cgactgcagg agaaggagga cctgcaggag     300
ctcaacgacc gctggccgt ctacatcgac aaagtgcgct ctctggagct cgagaacgcc     360
gggctgcgcc tgcgcatcac cgagtccgag gaggtggtga gccggaggt gtcgggcatt     420
```

| | |
|---|---|
| aaggccgcct acgaggccga gttggcggac gcgaggaaga cgttggattc ggtggcgaag | 480 |
| gagcgggcgc gcctgcagct cgagctgagc aaagtgcgcg aggagcacaa ggagctgaag | 540 |
| gccaggaatg ccaagaagga ggcggacctc ctggcggccc aggcgcgcct taaggacctc | 600 |
| gaggctctgc tcaactccaa ggaggccgcg ctgtccacgg cgctgggcga aagaggaac | 660 |
| ctggagaacg aagtgcggga cctgagggcg caggtggcca agttggaggg cgcgctgagc | 720 |
| gaggccaaga agcagctgca ggatgagatg ctgcgccgcg tggacgccga gaaccgcctg | 780 |
| cagaccctga aggaggagtt ggagttccag aagaacattt acagcgagga gctgcgggag | 840 |
| accaaacggc ggcacgagac cgcctggtg gagatcgaca cgggcggca gcaggaattc | 900 |
| gagagcaaat tggccgaggc gctgcaggac ctgcggcggc agcacgagga tcagatccgg | 960 |
| cactaccgcg acgagctgga aaagacctac ggggccaaac tggagaacgc gaagcagtct | 1020 |
| gcggagcgga acagcagcat ggcggggcg gcgcacgagg agctgcagca gacgcacatc | 1080 |
| cgcatcgaca gcctcagcgc agagctcagt cagctgcaga agcagctggc ggccaaagag | 1140 |
| gcgaagctgc gggaggtgga ggaggcgctg agccgggagc ggagggggg cggcggctg | 1200 |
| ctggccgaga aggagcgcga gatggcggag atgcgcgcgc ggatgcagca gcagttggat | 1260 |
| gagtaccagg agctgctgga catcaaactg gcgctggaca tggagatcaa cgcctaccgc | 1320 |
| aaactgctgg agggcgagga ggagcggctc cgtctgtctc cgagcccctc ctcccagcgc | 1380 |
| ggcgcgcgga gctccgggct gcagcactca ggcgcgggca gcgccaagaa gcggcgcctg | 1440 |
| gaggacgggg agggccggga gggccggag ggccgcacga gcttctcgca ccacgccagg | 1500 |
| accagcggga gggtcggcgt cgaggaggtg gacctggagg ggcgcttcgt ccgcctccgc | 1560 |
| aacaaatcca atgaggacca ggccctgggg aactggcagg tgaagcggca gaacggggac | 1620 |
| gaccccccc tgacgtaccg cttccccccg aagttcactc tgaaggcggg tcaggcggtc | 1680 |
| acgatctggg cctcggggc cggcgcgacc cacagccccc ccagcgatgt ggtgtggaag | 1740 |
| gcgcagagct cgtggggcag cggggacagt ctgcgcaccg ccctcatcaa ctccaacgga | 1800 |
| gaggaggtgg ccatgcggaa gttggtgcgc accgtcatca tcaacgacga cgacgaggat | 1860 |
| gaggaggacg acgaagtcag catccatcac cgccaccacc actcgggctg cagcggctcc | 1920 |
| gcagacccgg cggagtacaa cctgcgctcc cgcacggtgc tgtgcgggac gtgcgggcag | 1980 |
| cccgcagaca aaggcagcgc cgccgccgcc tcctccgcct cctccgcctc caccgtcacc | 2040 |
| gtcagccgcg gctaccgcag ctccggcggc ggcatcgggg agggactgct cggccgctcc | 2100 |
| tacgtgctgg gcggagccgg gccgcggcgg caggctccgg ccccgcaggg ctgcagcatt | 2160 |
| atgtaatgcg gaccccccg ggctgctccg cccctcccc cccgggcgg ccccccctc | 2220 |
| attttgggct catttccccc ccaaagcagc gcaaaccaaa gatggctttt tttgttctct | 2280 |
| tttctatggc cgcgttttgt acggagctcc caggggggt ttccctctt tttgtgaagg | 2340 |
| gagacggaga acctttattt ctacgccccc cccccataa aaaaaaaa | 2388 |

<210> SEQ ID NO 11
<211> LENGTH: 657
<212> TYPE: PRT
<213> ORGANISM: Gallus gallus

<400> SEQUENCE: 11

Met Ser Thr Pro Ser Gln Arg Arg Ser Gly Arg Gly Gly Gly Pro Ser
1               5                   10                  15

Gly Thr Pro Leu Ser Pro Thr Arg Ile Thr Arg Leu Gln Glu Lys Glu
            20                  25                  30

```
Asp Leu Gln Glu Leu Asn Asp Arg Leu Ala Val Tyr Ile Asp Lys Val
         35                  40                  45
Arg Ser Leu Glu Leu Glu Asn Ala Gly Leu Arg Leu Arg Ile Thr Glu
 50                  55                  60
Ser Glu Glu Val Val Ser Arg Glu Val Ser Gly Ile Lys Ala Ala Tyr
 65                  70                  75                  80
Glu Ala Glu Leu Ala Asp Ala Arg Lys Thr Leu Asp Ser Val Ala Lys
                 85                  90                  95
Glu Arg Ala Arg Leu Gln Leu Glu Leu Ser Lys Val Arg Glu Glu His
                100                 105                 110
Lys Glu Leu Lys Ala Arg Asn Ala Lys Lys Glu Ala Asp Leu Leu Ala
                115                 120                 125
Ala Gln Ala Arg Leu Lys Asp Leu Glu Ala Leu Leu Asn Ser Lys Glu
        130                 135                 140
Ala Ala Leu Ser Thr Ala Leu Gly Glu Lys Arg Asn Leu Glu Asn Glu
145                 150                 155                 160
Val Arg Asp Leu Arg Ala Gln Val Ala Lys Leu Glu Gly Ala Leu Ser
                165                 170                 175
Glu Ala Lys Lys Gln Leu Gln Asp Glu Met Leu Arg Arg Val Asp Ala
            180                 185                 190
Glu Asn Arg Leu Gln Thr Leu Lys Glu Glu Leu Glu Phe Gln Lys Asn
        195                 200                 205
Ile Tyr Ser Glu Glu Leu Arg Glu Thr Lys Arg Arg His Glu Thr Arg
210                 215                 220
Leu Val Glu Ile Asp Asn Gly Arg Gln Gln Phe Glu Ser Lys Leu
225                 230                 235                 240
Ala Glu Ala Leu Gln Asp Leu Arg Arg Gln His Glu Asp Gln Ile Arg
                245                 250                 255
His Tyr Arg Asp Glu Leu Glu Lys Thr Tyr Gly Ala Lys Leu Glu Asn
            260                 265                 270
Ala Lys Gln Ser Ala Glu Arg Asn Ser Ser Met Ala Gly Ala Ala His
        275                 280                 285
Glu Glu Leu Gln Gln Thr His Ile Arg Ile Asp Ser Leu Ser Ala Glu
290                 295                 300
Leu Ser Gln Leu Gln Lys Gln Leu Ala Ala Lys Glu Ala Lys Leu Arg
305                 310                 315                 320
Glu Val Glu Glu Ala Leu Ser Arg Glu Arg Glu Gly Gly Arg Arg Leu
                325                 330                 335
Leu Ala Glu Lys Glu Arg Glu Met Ala Glu Met Arg Ala Arg Met Gln
            340                 345                 350
Gln Gln Leu Asp Glu Tyr Gln Glu Leu Leu Asp Ile Lys Leu Ala Leu
        355                 360                 365
Asp Met Glu Ile Asn Ala Tyr Arg Lys Leu Leu Glu Gly Glu Glu Glu
    370                 375                 380
Arg Leu Arg Leu Ser Pro Ser Pro Ser Ser Gln Arg Gly Ala Arg Ser
385                 390                 395                 400
Ser Gly Leu Gln His Ser Gly Ala Gly Ser Ala Lys Lys Arg Arg Leu
                405                 410                 415
Glu Asp Gly Glu Gly Arg Glu Gly Arg Glu Gly Arg Thr Ser Phe Ser
            420                 425                 430
His His Ala Arg Thr Ser Gly Arg Val Gly Val Glu Val Asp Leu
        435                 440                 445
Glu Gly Arg Phe Val Arg Leu Arg Asn Lys Ser Asn Glu Asp Gln Ala
450                 455                 460
```

```
Leu Gly Asn Trp Gln Val Lys Arg Gln Asn Gly Asp Asp Pro Pro Leu
465                 470                 475                 480

Thr Tyr Arg Phe Pro Pro Lys Phe Thr Leu Lys Ala Gly Gln Ala Val
            485                 490                 495

Thr Ile Trp Ala Ser Gly Ala Gly Ala Thr His Ser Pro Pro Ser Asp
        500                 505                 510

Val Val Trp Lys Ala Gln Ser Ser Trp Gly Ser Gly Asp Ser Leu Arg
            515                 520                 525

Thr Ala Leu Ile Asn Ser Asn Gly Glu Glu Val Ala Met Arg Lys Leu
        530                 535                 540

Val Arg Thr Val Ile Ile Asn Asp Asp Asp Glu Asp Glu Glu Asp Asp
545                 550                 555                 560

Glu Val Ser Ile His His Arg His His His Ser Gly Cys Ser Gly Ser
                565                 570                 575

Ala Asp Pro Ala Glu Tyr Asn Leu Arg Ser Arg Thr Val Leu Cys Gly
            580                 585                 590

Thr Cys Gly Gln Pro Ala Asp Lys Gly Ser Ala Ala Ala Ser Ser
        595                 600                 605

Ala Ser Ser Ala Ser Thr Val Thr Val Ser Arg Gly Tyr Arg Ser Ser
        610                 615                 620

Gly Gly Gly Ile Gly Glu Gly Leu Leu Gly Arg Ser Tyr Val Leu Gly
625                 630                 635                 640

Gly Ala Gly Pro Arg Arg Gln Ala Pro Ala Pro Gln Gly Cys Ser Ile
            645                 650                 655

Met

<210> SEQ ID NO 12
<211> LENGTH: 2111
<212> TYPE: DNA
<213> ORGANISM: Xenopus laevis

<400> SEQUENCE: 12
ccaagctatg gagaccccag gtcagaagcg ggcgacccgc agcacccaca ccccactctc      60
ccccacccgt atcacccgcc tgcaggagaa ggaagatctg caggggctca atgaccgatt     120
ggccgtctac atcgacaagg tgcgttccct ggagctggag aacgcccggc tgcgtctgcg     180
aatcaccgag tctgaagacg tcatcagccg cgaggtcacg gcatcaagt cagcgtatga     240 gacggagctg gcggacgcac ggaaaaactct ggactcggtg gccaaggaga gggctcgtct     300
gcagctggag ctgagcaaga tccgcgagga gcacaaggag ctgaaagcga ggaatgccaa     360
gaaagagagc gatctattga cagcgcaggc cagactgaag gatttggagg ccctgttgaa     420
ctctaaagat gccgccctca ccacagcgct gggagagaag aggaatctgg agaatgagat     480
cagggaactt aaggctcaca ttgcaaagtt ggaggccagc ctcgccgaca caaagaaaca     540
actgcaggac gagatgctcc gtcgtgtgga tactgagaac cgtaaccaga cgctgaagga     600
ggaacttgag ttccaaaaga gcatttacaa cgaggagatg cgggagacta acgccgcca     660 tgagacccga ctggtggagg tcgacaacgg cgcgccagag gagtttgagt ctaaattggc     720
tgatgccctt catgagttgc gtgcccaaca tgagggcag ataggcctgt acaaggaaga     780
gctggggaag acttacaatg ccaagctgga gaatgccaag cagtcggcgg agaggaacag     840
cagtctggtg ggagaagctc aggaggagat tcagcagagc aggatccgca tcgacagtct     900
ctcggcccag ctcagccaac tgcagaaaca gctggcggcc agagaggcca aacttcggga     960
tctggaggac gcctatgcgc gtgaacggga ctccagccgc cggctcctgg cagacaagga    1020
```

```
ccgggagatg cggaaatga gggcccgcat gcaacaacag ctggacgagt accaggagct    1080
gctggacatt aaactggctc tggacatgga gatcaacgcc taccgcaagt tactggaggg    1140
agaggaggag aggctgcgtc tctccccag tcccaacacc cagaagaggt cggcccggac     1200
catcgcctct cactcggggg cccacatctc ctcctcggcc tccaagagac gtcgcctgga    1260
agaaggggaa tcgcggagca gcagcttcac ccaacacgcc cgcaccaccg ggaaagtgtc    1320
agtggaagag gtggatcccg agggaaata tgtccgactg aggaacaaga gtaatgagga    1380
ccaatcgctg gggaactggc agatcaagcg tcagatcggg gacgagaccc ccattgtgta    1440
caagttccct cccagactta cactaaaggc cggacaaacc gtaacgattt gggcatcagg    1500
agctggagcc acaaatagtc cccccagtga tttagtgtgg aaggcccaga gctcttgggg    1560
aacaggcgac agtattcgca cagctctgct cacatcaagc aatgaggaag ttgctatgag    1620
gaaactggtg cgaactgtgg tcatcaatga tgaagatgat gaagataatg atgatatgga    1680
acatcaccac caccatcatc atcatcatca tgatgggcag aactctagtg gagaccctgg    1740
ggagtacaac ctgcgctctc gcactatcgt ttgcaccagc tgtgggcgcc agctgagaa     1800 gagtgtcctg gcctcccagg ttctgggtt ggtcactgga tcatcaggtt cttcttcctc     1860
cagcgtcacc cttactcgga cctaccgtag cacaggggga accagcgggg gcagtggcct    1920
cggggagagt ccgtcacca ggaacttcat tgttggaaat ggccaacgtg cccaggtcgc     1980
cccgcagaac tgcagtataa tgtaaccgga tgccaccact gttcttatca ccaagtgccc    2040
aagctaaaga gaattttttg ttttttttaat gtattttatt ttttttttat actgcaagaa    2100
tttatataag g                                                         2111
```

<210> SEQ ID NO 13
<211> LENGTH: 665
<212> TYPE: PRT
<213> ORGANISM: Xenopus laevis

<400> SEQUENCE: 13

```
Met Glu Thr Pro Gly Gln Lys Arg Ala Thr Arg Ser Thr His Thr Pro
1               5                   10                  15

Leu Ser Pro Thr Arg Ile Thr Arg Leu Gln Glu Lys Glu Asp Leu Gln
            20                  25                  30

Gly Leu Asn Asp Arg Leu Ala Val Tyr Ile Asp Lys Val Arg Ser Leu
        35                  40                  45

Glu Leu Glu Asn Ala Arg Leu Arg Leu Arg Ile Thr Glu Ser Glu Asp
    50                  55                  60

Val Ile Ser Arg Glu Val Thr Gly Ile Lys Ser Ala Tyr Glu Thr Glu
65                  70                  75                  80

Leu Ala Asp Ala Arg Lys Thr Leu Asp Ser Val Ala Lys Glu Arg Ala
                85                  90                  95

Arg Leu Gln Leu Glu Leu Ser Lys Ile Arg Glu Glu His Lys Glu Leu
            100                 105                 110

Lys Ala Arg Asn Ala Lys Lys Glu Ser Asp Leu Leu Thr Ala Gln Ala
        115                 120                 125

Arg Leu Lys Asp Leu Glu Ala Leu Leu Asn Ser Lys Asp Ala Ala Leu
    130                 135                 140

Thr Thr Ala Leu Gly Glu Lys Arg Asn Leu Glu Asn Glu Ile Arg Glu
145                 150                 155                 160

Leu Lys Ala His Ile Ala Lys Leu Glu Ala Ser Leu Ala Asp Thr Lys
                165                 170                 175
```

```
Lys Gln Leu Gln Asp Glu Met Leu Arg Arg Val Asp Thr Glu Asn Arg
            180                 185                 190
Asn Gln Thr Leu Lys Glu Leu Glu Phe Gln Lys Ser Ile Tyr Asn
        195                 200                 205
Glu Glu Met Arg Glu Thr Lys Arg Arg His Glu Thr Arg Leu Val Glu
            210                 215                 220
Val Asp Asn Gly Arg Gln Arg Glu Phe Glu Ser Lys Leu Ala Asp Ala
225                 230                 235                 240
Leu His Glu Leu Arg Ala Gln His Glu Gly Gln Ile Gly Leu Tyr Lys
                245                 250                 255
Glu Glu Leu Gly Lys Thr Tyr Asn Ala Lys Leu Glu Asn Ala Lys Gln
            260                 265                 270
Ser Ala Glu Arg Asn Ser Ser Leu Val Gly Glu Ala Gln Glu Ile
        275                 280                 285
Gln Gln Ser Arg Ile Arg Ile Asp Ser Leu Ser Ala Gln Leu Ser Gln
            290                 295                 300
Leu Gln Lys Gln Leu Ala Ala Arg Glu Ala Lys Leu Arg Asp Leu Glu
305                 310                 315                 320
Asp Ala Tyr Ala Arg Glu Arg Asp Ser Ser Arg Arg Leu Leu Ala Asp
                325                 330                 335
Lys Asp Arg Glu Met Ala Glu Met Arg Ala Arg Met Gln Gln Gln Leu
            340                 345                 350
Asp Glu Tyr Gln Glu Leu Leu Asp Ile Lys Leu Ala Leu Asp Met Glu
        355                 360                 365
Ile Asn Ala Tyr Arg Lys Leu Leu Glu Gly Glu Glu Arg Leu Arg
            370                 375                 380
Leu Ser Pro Ser Pro Asn Thr Gln Lys Arg Ser Ala Arg Thr Ile Ala
385                 390                 395                 400
Ser His Ser Gly Ala His Ile Ser Ser Ala Ser Lys Arg Arg Arg
                405                 410                 415
Leu Glu Glu Gly Glu Ser Arg Ser Ser Ser Phe Thr Gln His Ala Arg
            420                 425                 430
Thr Thr Gly Lys Val Ser Val Glu Glu Val Asp Pro Glu Gly Lys Tyr
            435                 440                 445
Val Arg Leu Arg Asn Lys Ser Asn Glu Asp Gln Ser Leu Gly Asn Trp
450                 455                 460
Gln Ile Lys Arg Gln Ile Gly Asp Glu Thr Pro Ile Val Tyr Lys Phe
465                 470                 475                 480
Pro Pro Arg Leu Thr Leu Lys Ala Gly Gln Thr Val Thr Ile Trp Ala
                485                 490                 495
Ser Gly Ala Gly Ala Thr Asn Ser Pro Pro Ser Asp Leu Val Trp Lys
            500                 505                 510
Ala Gln Ser Ser Trp Gly Thr Gly Asp Ser Ile Arg Thr Ala Leu Leu
            515                 520                 525
Thr Ser Ser Asn Glu Glu Val Ala Met Arg Lys Leu Val Arg Thr Val
        530                 535                 540
Val Ile Asn Asp Glu Asp Asp Glu Asp Asn Asp Met Glu His His
545                 550                 555                 560
His His His His His His Asp Gly Gln Asn Ser Ser Gly Asp
                565                 570                 575
Pro Gly Glu Tyr Asn Leu Arg Ser Arg Thr Ile Val Cys Thr Ser Cys
            580                 585                 590
Gly Arg Pro Ala Glu Lys Ser Val Leu Ala Ser Gln Gly Ser Gly Leu
            595                 600                 605
```

```
Val Thr Gly Ser Ser Gly Ser Ser Ser Ser Val Thr Leu Thr Arg
    610                 615                 620

Thr Tyr Arg Ser Thr Gly Gly Thr Ser Gly Gly Ser Gly Leu Gly Glu
625                 630                 635                 640

Ser Pro Val Thr Arg Asn Phe Ile Val Gly Asn Gly Gln Arg Ala Gln
                645                 650                 655

Val Ala Pro Gln Asn Cys Ser Ile Met
            660                 665

<210> SEQ ID NO 14
<211> LENGTH: 2078
<212> TYPE: DNA
<213> ORGANISM: Danio rerio

<400> SEQUENCE: 14
```

| | | | | | |
|---|---|---|---|---|---|
| atggagactc | caggtcagaa | acgaagcagc | cgcggtgggg | tgaccaatgt | cctgtcccct | 60 |
| acccgcatct | ctcgattgca | ggaaaaggag | gacttgagca | acctgaatga | ccgtctggcg | 120 |
| gtctacatcg | ataaggttcg | ctctctggag | gtggagaacg | caggtctgcg | tatgcgcatc | 180 |
| actgaatccg | agacggagat | cagccgggag | ctgagtggca | tgaaagcggc | gtacgaggct | 240 |
| gaactcgcag | atgccaggaa | aacactggac | tcggtggcca | agaacgagc | ccgactgcaa | 300 |
| ctggagctca | gcaaagtgcg | tgaggactac | aaggagctga | aggccaggaa | cggtaagaaa | 360 |
| gaagcagatc | tggaatctgc | tctggccagg | ctgaaggatc | tggagtctct | actgaactcc | 420 |
| aaggacgcgt | ctctctccac | agctctgggg | gagaagagaa | cactgaggt | ggaagtcaga | 480 |
| gatttgaaag | cccagctggc | caagttggag | ggcagtctaa | cgatgcaaa | gaagcagctg | 540 |
| caggatgaaa | tgctgcgacg | tgtggatgcc | gaaaaccgaa | tccagacact | gaagaggag | 600 |
| ctggagttcc | agaagaacat | ctactctgag | gagctccgtg | agtctaagcg | cagatatgag | 660 |
| tcacgtgtgg | tggagattga | cagcggccgc | cagcaggatt | atgagagtaa | actggccgac | 720 |
| gctttaactg | acctccgcaa | ccaacatgaa | gagcagcttc | gcatctacaa | ggaagaaatc | 780 |
| gagaagacct | acaactccaa | gctggaaaat | gctcgctctt | ccgctgaaag | gaacagtcat | 840 |
| ctggttggag | ccgcccatga | ggaactgcag | caaacacgtg | ttaggatgga | gggtgtgagt | 900 |
| tcacagctca | gtcagctgca | gaaacagttg | gctgctcgag | aggcgaagat | ccgcgagctg | 960 |
| gaagaggccc | tgtccagaga | gagggatatt | ttgcgccgtc | gtctggagga | caaggagaag | 1020 |
| gagatggctg | agatgagaca | gcgcatgcag | caacagctgg | acgagtacca | ggagctgctg | 1080 |
| gacatcaaac | tcgctctgga | catggagatc | agtgcctaca | ggaagcttct | ggagggagag | 1140 |
| gaggaaagac | ttcgtctgtc | tccgagtcct | cctcctgctc | gtggggtgac | ggtgaccccgc | 1200 |
| tcctctggtt | caggctctca | cactcgtgtg | gttcagagca | gcaccagtcg | cacatcctcc | 1260 |
| ggcagcgcca | gaaacggcg | cttgaatgat | aacgacagtg | atgcctccag | tgtggttgga | 1320 |
| ggaacagtga | cccgcacacg | gatcttccag | caagcctcag | ccagcggccg | cgtcaccgtt | 1380 |
| gacgaagtcg | acctggaagg | aaaatttgtg | cggcttaata | acaagtctga | ccaggatcag | 1440 |
| tctctgggtc | actggcaggt | gaagaggcag | attggttctg | gcactccat | cgtctacaag | 1500 |
| tttccaccca | aatttaacct | gaaggcaggg | cagactgtca | cgatctgggc | tgcaggagcc | 1560 |
| ggaggcaccc | acagtcctcc | cagtgacctg | gtgtggaaga | cccagaactc | atggggcagc | 1620 |
| ggtgatttgt | tccagaccac | cctcatcagc | tccagcggag | aggaaatggc | gatgagaaaa | 1680 |
| gtcacacgta | ctctgttcca | ggatgaggaa | gatgatgaga | tggcggctca | cagcacatgc | 1740 |
| ggagacagcg | agtataacct | gcgcagccgt | actgtgctgt | gcggctcgtg | tggtcagccg | 1800 |

-continued

```
tccgacagga acagcagctg tgtttctgcc agctcaggag tgtccagcgc atctcgctcc    1860
ttcagcagtg gaggaggagg aggactcact gaagcttttg tgtcgccctc tcactttatt    1920
gtgagcaacg acaaacccag acaggctgga cccaaagtgg acaactgctc tattatgtag    1980
aggagctgaa agcaaaccct gaccatctgt gctttcacag aaaccaggcg gaactgatcc    2040
caaaactagt ttcttttcag tttttttatg tcttatca                            2078
```

<210> SEQ ID NO 15
<211> LENGTH: 659
<212> TYPE: PRT
<213> ORGANISM: Danio rerio

<400> SEQUENCE: 15

```
Met Glu Thr Pro Gly Gln Lys Arg Ser Ser Arg Gly Gly Val Thr Asn
 1               5                  10                  15

Val Leu Ser Pro Thr Arg Ile Ser Arg Leu Gln Glu Lys Glu Asp Leu
                20                  25                  30

Ser Asn Leu Asn Asp Arg Leu Ala Val Tyr Ile Asp Lys Val Arg Ser
            35                  40                  45

Leu Glu Val Glu Asn Ala Gly Leu Arg Met Arg Ile Thr Glu Ser Glu
        50                  55                  60

Thr Glu Ile Ser Arg Glu Leu Ser Gly Met Lys Ala Ala Tyr Glu Ala
65                  70                  75                  80

Glu Leu Ala Asp Ala Arg Lys Thr Leu Asp Ser Val Ala Lys Glu Arg
                85                  90                  95

Ala Arg Leu Gln Leu Glu Leu Ser Lys Val Arg Glu Asp Tyr Lys Glu
            100                 105                 110

Leu Lys Ala Arg Asn Gly Lys Lys Glu Ala Asp Leu Glu Ser Ala Leu
        115                 120                 125

Ala Arg Leu Lys Asp Leu Glu Ser Leu Asn Ser Lys Asp Ala Ser
    130                 135                 140

Leu Ser Thr Ala Leu Gly Glu Lys Arg Thr Leu Glu Val Glu Val Arg
145                 150                 155                 160

Asp Leu Lys Ala Gln Leu Ala Lys Leu Glu Gly Ser Leu Asn Asp Ala
                165                 170                 175

Lys Lys Gln Leu Gln Asp Glu Met Leu Arg Arg Val Asp Ala Glu Asn
            180                 185                 190

Arg Ile Gln Thr Leu Lys Glu Glu Leu Glu Phe Gln Lys Asn Ile Tyr
        195                 200                 205

Ser Glu Glu Leu Arg Glu Ser Lys Arg Arg Tyr Glu Ser Arg Val Val
    210                 215                 220

Glu Ile Asp Ser Gly Arg Gln Gln Asp Tyr Glu Ser Lys Leu Ala Asp
225                 230                 235                 240

Ala Leu Thr Asp Leu Arg Asn Gln His Glu Glu Gln Leu Arg Ile Tyr
                245                 250                 255

Lys Glu Glu Ile Glu Lys Thr Tyr Asn Ser Lys Leu Glu Asn Ala Arg
            260                 265                 270

Ser Ser Ala Glu Arg Asn Ser His Leu Val Gly Ala Ala His Glu Glu
        275                 280                 285

Leu Gln Gln Thr Arg Val Arg Met Glu Gly Val Ser Ser Gln Leu Ser
    290                 295                 300

Gln Leu Gln Lys Gln Leu Ala Ala Arg Glu Ala Lys Ile Arg Glu Leu
305                 310                 315                 320

Glu Glu Ala Leu Ser Arg Glu Arg Asp Ile Leu Arg Arg Arg Leu Glu
```

```
                    325                 330                 335
Asp Lys Glu Lys Glu Met Ala Glu Met Arg Gln Arg Met Gln Gln Gln
                340                 345                 350
Leu Asp Glu Tyr Gln Glu Leu Leu Asp Ile Lys Leu Ala Leu Asp Met
            355                 360                 365
Glu Ile Ser Ala Tyr Arg Lys Leu Leu Glu Gly Glu Glu Arg Leu
        370                 375                 380
Arg Leu Ser Pro Ser Pro Pro Ala Arg Gly Val Thr Val Thr Arg
385                 390                 395                 400
Ser Ser Gly Ser Gly Ser His Thr Arg Val Val Gln Ser Ser Thr Ser
                405                 410                 415
Arg Thr Ser Ser Gly Ser Ala Lys Lys Arg Arg Leu Asn Asp Asn Asp
                420                 425                 430
Ser Asp Ala Ser Ser Val Val Gly Gly Thr Val Thr Arg Thr Arg Ile
                435                 440                 445
Phe Gln Gln Ala Ser Ala Ser Gly Arg Val Thr Val Asp Glu Val Asp
        450                 455                 460
Leu Glu Gly Lys Phe Val Arg Leu Asn Asn Lys Ser Asp Gln Asp Gln
465                 470                 475                 480
Ser Leu Gly His Trp Gln Val Lys Arg Gln Ile Gly Ser Gly Thr Pro
                485                 490                 495
Ile Val Tyr Lys Phe Pro Pro Lys Phe Asn Leu Lys Ala Gly Gln Thr
                500                 505                 510
Val Thr Ile Trp Ala Ala Gly Ala Gly Gly Thr His Ser Pro Pro Ser
                515                 520                 525
Asp Leu Val Trp Lys Thr Gln Asn Ser Trp Gly Ser Gly Asp Leu Phe
        530                 535                 540
Gln Thr Thr Leu Ile Ser Ser Ser Gly Glu Glu Met Ala Met Arg Lys
545                 550                 555                 560
Val Thr Arg Thr Leu Phe Gln Asp Glu Glu Asp Asp Glu Met Ala Ala
                565                 570                 575
His Ser Thr Cys Gly Asp Ser Glu Tyr Asn Leu Arg Ser Arg Thr Val
                580                 585                 590
Leu Cys Gly Ser Cys Gly Gln Pro Ser Asp Arg Asn Ser Ser Cys Val
            595                 600                 605
Ser Ala Ser Ser Gly Val Ser Ser Ala Ser Arg Ser Phe Ser Ser Gly
        610                 615                 620
Gly Gly Gly Gly Leu Thr Glu Ala Phe Val Ser Pro Ser His Phe Ile
625                 630                 635                 640
Val Ser Asn Asp Lys Pro Arg Gln Ala Gly Pro Lys Val Asp Asn Cys
                645                 650                 655
Ser Ile Met

<210> SEQ ID NO 16
<211> LENGTH: 15
<212> TYPE: PRT
<213> ORGANISM: Mus musculus

<400> SEQUENCE: 16

Leu Leu Gly Asn Ser Ser Pro Arg Ser Gln Ser Ser Gln Asn Cys
1               5                   10                  15

<210> SEQ ID NO 17
<211> LENGTH: 17
<212> TYPE: PRT
<213> ORGANISM: Gallus gallus
```

-continued

```
<400> SEQUENCE: 17

Val Leu Gly Gly Ala Gly Pro Arg Arg Gln Ala Pro Ala Pro Gln Gly
1               5                   10                  15

Cys

<210> SEQ ID NO 18
<211> LENGTH: 15
<212> TYPE: PRT
<213> ORGANISM: Xenopus laevis

<400> SEQUENCE: 18

Ile Val Gly Asn Gly Gln Arg Ala Gln Val Ala Pro Gln Asn Cys
1               5                   10                  15

<210> SEQ ID NO 19
<211> LENGTH: 20
<212> TYPE: PRT
<213> ORGANISM: Danio rerio

<400> SEQUENCE: 19

Ile Val Ser Asn Asp Lys Pro Arg Gln Ala Gly Pro Lys Val Asp Asn
1               5                   10                  15

Cys Ser Ile Met
            20

<210> SEQ ID NO 20
<211> LENGTH: 18
<212> TYPE: PRT
<213> ORGANISM: Homo sapiens

<400> SEQUENCE: 20

Leu Leu Gly Asn Ser Ser Pro Arg Thr Gln Ser Pro Gln Asn Cys Ser
1               5                   10                  15

Ile Met

<210> SEQ ID NO 21
<211> LENGTH: 18
<212> TYPE: PRT
<213> ORGANISM: Mus musculus

<400> SEQUENCE: 21

Leu Leu Gly Asn Ser Ser Pro Arg Ser Gln Ser Ser Gln Asn Cys Ser
1               5                   10                  15

Ile Met

<210> SEQ ID NO 22
<211> LENGTH: 20
<212> TYPE: PRT
<213> ORGANISM: Gallus gallus

<400> SEQUENCE: 22

Val Leu Gly Gly Ala Gly Pro Arg Arg Gln Ala Pro Ala Pro Gln Gly
1               5                   10                  15

Cys Ser Ile Met
            20

<210> SEQ ID NO 23
<211> LENGTH: 18
<212> TYPE: PRT
<213> ORGANISM: Xenopus laevis

<400> SEQUENCE: 23
```

```
Ile Val Gly Asn Gly Gln Arg Ala Gln Val Ala Pro Gln Asn Cys Ser
1               5                   10                  15

Ile Met

<210> SEQ ID NO 24
<211> LENGTH: 20
<212> TYPE: PRT
<213> ORGANISM: Danio rerio

<400> SEQUENCE: 24

Ile Val Ser Asn Asp Lys Pro Arg Gln Ala Gly Pro Lys Val Asp Asn
1               5                   10                  15

Cys Ser Ile Met
            20
```